(12) United States Patent
Helmick et al.

(10) Patent No.: US 10,857,013 B2
(45) Date of Patent: Dec. 8, 2020

(54) SCAFFOLD LOADING AND DELIVERY SYSTEMS

(71) Applicant: Lyra Therapeutics, Inc., Watertown, MA (US)

(72) Inventors: Marc Helmick, Newton, MA (US); Jonathan Merlo, Boston, MA (US); Lee Core, Needham, MA (US); Quyhn Pham, Methuen, MA (US); Anthony Prostrollo, Rosemount, MN (US); Ross Paulson, Ramsey, MN (US); Danielle Peterson, Crystal, MN (US); Garrett Prahl, Brooklyn Park, MN (US); Randall Beyreis, Corcoran, MN (US); Michele Chouinard, Maple Grove, MN (US)

(73) Assignee: Lyra Therapeutics, Inc., Watertown, MA (US)

(*) Notice: Subject to any disclaimer, the term of this patent is extended or adjusted under 35 U.S.C. 154(b) by 176 days.

(21) Appl. No.: 16/180,452

(22) Filed: Nov. 5, 2018

(65) Prior Publication Data

US 2019/0070029 A1 Mar. 7, 2019

Related U.S. Application Data

(62) Division of application No. 15/197,089, filed on Jun. 29, 2016, now Pat. No. 10,159,586.

(60) Provisional application No. 62/186,311, filed on Jun. 29, 2015, provisional application No. 62/236,886, filed on Oct. 3, 2015, provisional application No. 62/314,239, filed on Mar. 28, 2016.

(51) Int. Cl.
*A61F 2/95* (2013.01)
*A61F 2/18* (2006.01)
*A61F 2/958* (2013.01)
*A61F 2/966* (2013.01)
*A61F 2/90* (2013.01)

(52) U.S. Cl.
CPC ................ *A61F 2/95* (2013.01); *A61F 2/186* (2013.01); *A61F 2/958* (2013.01); *A61F 2/966* (2013.01); *A61F 2/90* (2013.01); *A61F 2/9522* (2020.05); *A61F 2002/9665* (2013.01)

(58) Field of Classification Search
CPC .. A61F 2/95; A61F 2/958; A61F 2/966; A61F 2/186; A61F 2/9522; A61F 2002/9665; A61F 2/90; A61F 2002/9522; A61F 2002/9517
See application file for complete search history.

(56) References Cited

U.S. PATENT DOCUMENTS

| | | |
|---|---|---|
| 4,886,062 A | 12/1989 | Wiktor |
| 5,133,732 A | 7/1992 | Wiktor |
| 5,170,802 A | 12/1992 | Mehra |
| 5,224,491 A | 7/1993 | Mehra |
| 5,265,601 A | 11/1993 | Mehra |

(Continued)

FOREIGN PATENT DOCUMENTS

WO WO/2017/004209 1/2017

*Primary Examiner* — Amy R Weisberg
(74) *Attorney, Agent, or Firm* — Medlen & Carroll, LLP

(57) ABSTRACT

This disclosure describes, inter alia, materials, devices, kits and methods that may be used for loading scaffolds into delivery devices and delivery of scaffolds into the body of a patient, including delivery of scaffolds to the sinuses for the treatment of chronic sinusitis, among other purposes.

13 Claims, 33 Drawing Sheets

(56) References Cited

U.S. PATENT DOCUMENTS

| | | | |
|---|---|---|---|
| 5,336,163 A | 8/1994 | DeMane et al. |
| 5,591,198 A | 1/1997 | Bovie et al. |
| 5,613,981 A | 3/1997 | Bovie et al. |
| 5,626,604 A | 5/1997 | Cottone, Jr. |
| 5,653,727 A | 8/1997 | Wiktor |
| 5,733,325 A | 3/1998 | Robinson |
| 5,810,873 A | 9/1998 | Morales |
| 5,897,521 A | 4/1999 | Lavigne |
| 5,899,934 A | 5/1999 | Amundson et al. |
| 5,913,896 A | 6/1999 | Bovie et al. |
| 5,931,851 A | 8/1999 | Morales |
| 6,018,857 A | 2/2000 | Duffy |
| 6,047,431 A | 4/2000 | Canonica |
| 6,132,458 A * | 10/2000 | Staehle ............ A61F 2/95 623/1.11 |
| 6,149,680 A | 11/2000 | Shelso |
| 6,161,029 A | 12/2000 | Spreigl et al. |
| 6,301,507 B1 | 10/2001 | Bakels et al. |
| 6,330,481 B1 | 12/2001 | Van Wiik et al. |
| 6,346,116 B1 | 2/2002 | Brooks et al. |
| 6,385,491 B1 | 5/2002 | Lindemans et al. |
| 6,449,507 B1 | 9/2002 | Hill et al. |
| 6,487,446 B1 | 11/2002 | Hill et al. |
| 6,532,388 B1 | 3/2003 | Hill et al. |
| 6,543,452 B1 | 4/2003 | Lavigne |
| 6,628,987 B1 | 9/2003 | Hill et al. |
| 6,718,208 B2 | 4/2004 | Hill et al. |
| 6,770,080 B2 | 8/2004 | Kaolan et al. |
| 6,863,684 B2 | 3/2005 | Kim et al. |
| 6,904,318 B2 | 6/2005 | Hill et al. |
| 6,909,920 B2 | 6/2005 | Lokhoff et al. |
| 6,923,828 B1 | 8/2005 | Wiktor |
| 6,945,992 B2 | 9/2005 | Goodson, IV et al. |
| 7,184,828 B2 | 2/2007 | Hill et al. |
| 7,184,829 B2 | 2/2007 | Hill et al. |
| 7,323,008 B2 | 1/2008 | Kantor et al. |
| 7,356,903 B2 | 4/2008 | Krivoruchko et al. |
| 7,361,168 B2 | 4/2008 | Makower et al. |
| 7,386,351 B2 | 6/2008 | Hine et al. |
| 7,410,480 B2 | 8/2008 | Muni et al. |
| 7,419,497 B2 | 9/2008 | Muni et al. |
| 7,462,175 B2 | 12/2008 | Chang et al. |
| 7,500,971 B2 | 3/2009 | Chang et al. |
| 7,520,876 B2 | 4/2009 | Ressemann et al. |
| 7,544,192 B2 | 6/2009 | Eaton et al. |
| 7,547,323 B2 | 6/2009 | Lavigne |
| 7,559,925 B2 | 7/2009 | Goldfarb et al. |
| 7,578,899 B2 | 8/2009 | Edwin et al. |
| 7,615,072 B2 | 11/2009 | Rust et al. |
| 7,641,644 B2 | 1/2010 | Chang et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,662,141 B2 | 2/2010 | Eaton et al. |
| 7,662,142 B2 | 2/2010 | Eaton et al. |
| 7,678,099 B2 | 3/2010 | Ressemann et al. |
| 7,686,798 B2 | 3/2010 | Eaton et al. |
| 7,691,094 B2 | 4/2010 | Eaton et al. |
| 7,697,972 B2 | 4/2010 | Verard et al. |
| 7,704,259 B2 | 4/2010 | Kaplan et al. |
| 7,713,255 B2 | 5/2010 | Eaton et al. |
| 7,717,933 B2 | 5/2010 | Becker |
| 7,717,955 B2 | 5/2010 | Lane et al. |
| 7,720,521 B2 | 5/2010 | Chang et al. |
| 7,727,186 B2 | 6/2010 | Makower et al. |
| 7,727,226 B2 | 6/2010 | Chang et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,803,150 B2 | 9/2010 | Chang et al. |
| 7,806,919 B2 | 10/2010 | Bloom et al. |
| 7,815,673 B2 | 10/2010 | Bloom et al. |
| 7,842,062 B2 | 11/2010 | Keith et al. |
| 7,854,744 B2 | 12/2010 | Becker |
| 7,951,131 B2 | 1/2011 | Eaton et al. |
| 7,879,061 B2 | 2/2011 | Keith et al. |
| 7,914,639 B2 | 3/2011 | Layne et al. |
| 7,951,130 B2 | 3/2011 | Eaton et al. |
| 7,918,871 B2 | 4/2011 | Truitt et al. |
| 7,951,132 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 7,955,346 B2 | 6/2011 | Mauch et al. |
| 7,967,807 B2 | 6/2011 | Murray |
| 7,967,857 B2 | 6/2011 | Lane |
| 7,972,378 B2 | 7/2011 | Tabor et al. |
| 7,993,350 B2 | 8/2011 | Ventura et al. |
| 7,993,675 B2 | 8/2011 | Oliver et al. |
| 8,025,635 B2 | 9/2011 | Eaton et al. |
| 8,034,099 B2 | 10/2011 | Pellegrini |
| 8,046,052 B2 | 10/2011 | Verard et al. |
| 8,052,693 B2 | 11/2011 | Shahoian |
| 8,052,750 B2 | 11/2011 | Tuval et al. |
| 8,088,101 B2 | 1/2012 | Chang et al. |
| 8,100,933 B2 | 1/2012 | Becker |
| 8,109,918 B2 | 2/2012 | Eaton et al. |
| 8,114,062 B2 | 2/2012 | Muni et al. |
| 8,114,113 B2 | 2/2012 | Becker |
| 8,118,757 B2 | 2/2012 | Morriss |
| 8,123,722 B2 | 2/2012 | Chang et al. |
| 8,126,549 B2 | 2/2012 | Sigg et al. |
| 8,142,422 B2 | 3/2012 | Makower et al. |
| 8,146,400 B2 | 4/2012 | Goldfarb et al. |
| 8,152,842 B2 | 4/2012 | Schlun |
| 8,157,940 B2 | 4/2012 | Edwin et al. |
| 8,172,828 B2 | 5/2012 | Chang et al. |
| 8,182,432 B2 | 5/2012 | Kim et al. |
| 8,190,389 B2 | 5/2012 | Kim et al. |
| 8,192,420 B2 | 6/2012 | Morriss et al. |
| 8,206,349 B2 | 6/2012 | Slenker et al. |
| 8,211,169 B2 | 7/2012 | Lane et al. |
| 8,241,266 B2 | 8/2012 | Keith et al. |
| 8,249,700 B2 | 8/2012 | Clifford et al. |
| 8,273,253 B2 | 9/2012 | Curran |
| 8,277,503 B2 | 10/2012 | Lavigne |
| 8,277,504 B2 | 10/2012 | Lavigne |
| 8,282,667 B2 | 10/2012 | Drontle et al. |
| 8,313,762 B2 | 11/2012 | Oliver et al. |
| 8,317,816 B2 | 11/2012 | Becker |
| 8,328,865 B2 | 12/2012 | Bales, Jr. et al. |
| 8,328,867 B2 | 12/2012 | Dolan et al. |
| 8,333,799 B2 | 12/2012 | Bales, Jr. et al. |
| 8,333,800 B2 | 12/2012 | Bruszewski et al. |
| 8,337,454 B2 | 12/2012 | Eaton et al. |
| 8,337,650 B2 | 12/2012 | Edwin et al. |
| 8,348,969 B2 | 1/2013 | Keith et al. |
| 8,348,995 B2 | 1/2013 | Tuval et al. |
| 8,348,996 B2 | 1/2013 | Tuval et al. |
| 8,353,952 B2 | 1/2013 | Thompson et al. |
| 8,377,083 B2 | 2/2013 | Mauch et al. |
| 8,414,473 B2 | 4/2013 | Jenkins et al. |
| 8,414,643 B2 | 4/2013 | Tuval et al. |
| 8,425,457 B2 | 4/2013 | John et al. |
| 8,425,488 B2 | 4/2013 | Clifford et al. |
| 8,435,261 B2 | 5/2013 | Arcand et al. |
| 8,435,290 B2 | 5/2013 | Clifford et al. |
| 8,439,687 B1 | 5/2013 | Morriss et al. |
| 8,452,392 B2 | 5/2013 | Morriss et al. |
| 8,460,323 B2 | 6/2013 | Mauch et al. |
| 8,468,667 B2 * | 6/2013 | Straubinger ............ A61F 2/95 29/237 |
| 8,485,199 B2 | 7/2013 | Morriss |
| 8,500,793 B2 | 8/2013 | Zipse et al. |
| 8,500,801 B2 | 8/2013 | Eberhardt et al. |
| 8,529,548 B2 | 9/2013 | Blott et al. |
| 8,529,941 B2 | 9/2013 | Hakimimehr et al. |
| 8,535,707 B2 | 9/2013 | Arensdorf et al. |
| 8,540,694 B2 | 9/2013 | Flaherty et al. |
| 8,551,156 B2 | 10/2013 | Wack et al. |
| 8,562,672 B2 | 10/2013 | Bonhoeffer et al. |
| 8,563,510 B2 | 10/2013 | Hakimimehr et al. |
| 8,568,439 B2 | 10/2013 | Keith et al. |

(56) References Cited

U.S. PATENT DOCUMENTS

| | | | |
|---|---|---|---|
| 8,585,728 B2 | 11/2013 | Keith et al. |
| 8,585,729 B2 | 11/2013 | Keith et al. |
| 8,585,730 B2 | 11/2013 | Eaton et al. |
| 8,585,731 B2 | 11/2013 | Abbate et al. |
| 8,617,337 B2 | 12/2013 | Layne et al. |
| 8,623,043 B1 | 1/2014 | Keith et al. |
| 8,647,379 B2 | 2/2014 | McDermott et al. |
| 8,647,458 B2 | 2/2014 | Banas et al. |
| 8,657,846 B2 | 2/2014 | Keith et al. |
| 8,657,867 B2 | 2/2014 | Dorn et al. |
| 8,663,192 B2 | 3/2014 | Hester et al. |
| 8,673,000 B2 | 3/2014 | Tabor et al. |
| 8,673,099 B2 | 3/2014 | Bogert |
| 8,691,288 B2 | 4/2014 | Myntti |
| 8,702,626 B1 | 4/2014 | Kim et al. |
| 8,702,702 B1 | 4/2014 | Edwards et al. |
| 8,715,169 B2 | 5/2014 | Chang et al. |
| 8,721,591 B2 | 5/2014 | Chang et al. |
| 8,740,839 B2 | 6/2014 | Eaton et al. |
| 8,740,929 B2 | 6/2014 | Gopferich et al. |
| 8,747,297 B2 | 6/2014 | Miyoshi et al. |
| 8,747,389 B2 | 6/2014 | Goldfarb et al. |
| 8,747,460 B2 | 6/2014 | Tuval et al. |
| 8,758,420 B2 | 6/2014 | Dorn et al. |
| 8,763,222 B2 | 7/2014 | Abbate et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,764,786 B2 | 7/2014 | Becker |
| 8,765,715 B2 | 7/2014 | Oliver et al. |
| 8,777,017 B2 | 7/2014 | Curran |
| 8,777,911 B2 | 7/2014 | Heagle et al. |
| 8,777,926 B2 | 7/2014 | Chang et al. |
| 8,795,713 B2 | 8/2014 | Makower et al. |
| 8,801,670 B2 | 8/2014 | Drontle et al. |
| 8,801,775 B2 | 8/2014 | Griswold |
| 8,801,776 B2 | 8/2014 | House et al. |
| 8,802,131 B2 | 8/2014 | Arensdorf et al. |
| 8,828,041 B2 | 9/2014 | Chang et al. |
| 8,834,513 B2 | 9/2014 | Hanson et al. |
| 8,834,564 B2 | 9/2014 | Tuval et al. |
| 8,840,602 B2 | 9/2014 | Morris et al. |
| 8,845,619 B2 | 9/2014 | Blott et al. |
| 8,852,143 B2 | 10/2014 | Chang et al. |
| 8,858,586 B2 | 10/2014 | Chang et al. |
| 8,858,974 B2 | 10/2014 | Eaton et al. |
| 8,864,774 B2 | 10/2014 | Liu et al. |
| 8,864,787 B2 | 10/2014 | Muni et al. |
| 8,870,893 B2 | 10/2014 | Makower et al. |
| 8,876,894 B2 | 11/2014 | Tuval et al. |
| 8,876,895 B2 | 11/2014 | Tuval et al. |
| 8,888,686 B2 | 11/2014 | Drontle et al. |
| 8,894,614 B2 | 11/2014 | Muni et al. |
| 8,905,922 B2 | 12/2014 | Makower et al. |
| 8,920,419 B2 | 12/2014 | Edwards et al. |
| 8,926,689 B2 | 1/2015 | Bogert |
| 8,932,276 B1 | 1/2015 | Morriss et al. |
| 8,945,088 B2 | 2/2015 | Chang et al. |
| 8,951,225 B2 | 2/2015 | Evard et al. |
| 8,968,269 B2 | 3/2015 | Becker |
| 8,979,888 B2 | 3/2015 | Morriss et al. |
| 8,986,341 B2 | 3/2015 | Abbate et al. |
| 8,997,998 B2 | 4/2015 | Curran et al. |
| 9,005,284 B2 | 4/2015 | Ressemann |
| 9,011,363 B2 | 4/2015 | Clopp et al. |
| 9,192,692 B2 | 4/2015 | Medina et al. |
| 9,022,967 B2 | 5/2015 | Oliver et al. |
| 9,039,657 B2 | 5/2015 | Makower et al. |
| 9,039,680 B2 | 5/2015 | Makower et al. |
| 9,050,440 B2 | 6/2015 | Becker |
| 9,055,965 B2 | 6/2015 | Chang et al. |
| 9,072,619 B2 | 7/2015 | Lam et al. |
| 9,072,681 B2 | 7/2015 | Hakimimehr et al. |
| 9,078,783 B2 | 7/2015 | Morriss et al. |
| 9,084,691 B2 | 7/2015 | Wack et al. |
| 9,084,876 B2 | 7/2015 | Makower et al. |
| 9,089,258 B2 | 7/2015 | Goldfarb et al. |
| 9,095,364 B2 | 8/2015 | Muni et al. |
| 9,095,646 B2 | 8/2015 | Chow et al. |
| 9,101,384 B2 | 8/2015 | Makower et al. |
| 9,101,739 B2 | 8/2015 | Lesch, Jr. et al. |
| 9,114,040 B2 | 8/2015 | Dorn et al. |
| 9,138,569 B2 | 9/2015 | Edgren et al. |
| 9,144,663 B2 | 9/2015 | Ahlberg et al. |
| 9,192,751 B2 | 11/2015 | Macaulay et al. |
| 9,220,879 B2 | 12/2015 | Chang et al. |
| 9,238,125 B2 | 1/2016 | Vaccaro et al. |
| 9,241,834 B2 | 1/2016 | Chang et al. |
| 9,271,925 B2 | 3/2016 | Hammerick |
| 9,295,547 B2 | 3/2016 | Costello et al. |
| 9,308,346 B2 | 4/2016 | Soundararajan |
| 9,308,358 B2 | 4/2016 | Oliver et al. |
| 9,308,361 B2 | 4/2016 | Muni et al. |
| 9,320,876 B2 | 4/2016 | Ressemann et al. |
| 9,333,220 B2 | 5/2016 | Tijsma et al. |
| 9,333,365 B2 | 5/2016 | Zhao |
| 9,351,750 B2 | 5/2016 | Muni et al. |
| 9,393,137 B2 * | 7/2016 | Rusk .................. A61F 2/89 |
| 9,398,966 B2 | 7/2016 | Thompson |
| 9,402,719 B2 | 8/2016 | Lane |
| 9,427,343 B2 | 8/2016 | Bogert |
| 9,456,897 B2 | 10/2016 | Krivoruchko et al. |
| 9,498,239 B2 | 11/2016 | Schreck et al. |
| 9,504,556 B2 | 11/2016 | Bebb |
| 9,504,812 B2 | 11/2016 | Edgren et al. |
| 9,561,119 B2 | 2/2017 | Eberhardt et al. |
| 9,597,485 B2 | 3/2017 | Edgren et al. |
| 9,622,850 B2 | 4/2017 | Bebb et al. |
| 9,622,895 B2 | 4/2017 | Cohen |
| 9,629,644 B2 | 4/2017 | Schreck et al. |
| 9,629,704 B2 | 4/2017 | Melsheimer |
| 9,649,477 B2 | 5/2017 | Muni et al. |
| 9,662,168 B2 | 5/2017 | Edwards et al. |
| 9,675,451 B2 | 6/2017 | Garde et al. |
| 9,681,914 B2 | 6/2017 | Edwards et al. |
| 9,700,326 B2 | 7/2017 | Morriss et al. |
| 9,707,110 B2 | 7/2017 | McDermott et al. |
| 9,717,612 B2 | 8/2017 | Dorn et al. |
| 9,724,222 B2 | 8/2017 | Lim |
| 9,833,349 B2 | 12/2017 | Dorn |
| 2003/0083730 A1 | 5/2003 | Stinson |
| 2003/0114910 A1 | 6/2003 | Juhani Laakso |
| 2003/0135970 A1 | 7/2003 | Thornton |
| 2003/0225445 A1 | 12/2003 | Derus |
| 2004/0199239 A1 | 10/2004 | Austin |
| 2006/0184226 A1 | 8/2006 | Austin |
| 2006/0230592 A1 | 10/2006 | Heaney |
| 2007/0079494 A1 | 4/2007 | Serrano |
| 2007/0173927 A1 * | 7/2007 | Shin .................. A61F 2/90 623/1.18 |
| 2007/0208252 A1 | 9/2007 | Makower |
| 2007/0239271 A1 * | 10/2007 | Nguyen .............. A61F 2/2436 623/2.11 |
| 2007/0270931 A1 | 11/2007 | Leanna |
| 2007/0270932 A1 | 11/2007 | Headley |
| 2007/0270937 A1 | 11/2007 | Leanna |
| 2007/0288034 A1 | 12/2007 | MacCollum |
| 2007/0288080 A1 | 12/2007 | Maccollum |
| 2008/0027528 A1 | 1/2008 | Jagger |
| 2008/0243140 A1 | 10/2008 | Gopferich et al. |
| 2008/0262592 A1 | 10/2008 | Jordan |
| 2009/0030499 A1 | 1/2009 | Bebb et al. |
| 2009/0054976 A1 * | 2/2009 | Tuval ................. A61F 2/0095 623/2.11 |
| 2009/0082840 A1 | 3/2009 | Rusk |
| 2009/0171434 A1 | 7/2009 | Rusk |
| 2009/0182407 A1 | 7/2009 | Leanna |
| 2009/0192518 A1 | 7/2009 | Golden |
| 2009/0192601 A1 * | 7/2009 | Rafiee ................ A61F 2/2436 623/2.11 |
| 2009/0198315 A1 * | 8/2009 | Boudjemline .......... D04C 3/48 623/1.2 |
| 2009/0270965 A1 | 10/2009 | Sinha et al. |
| 2009/0299449 A1 | 12/2009 | Styrc |

(56) References Cited

U.S. PATENT DOCUMENTS

| | | |
|---|---|---|
| 2009/0299451 A1 | 12/2009 | Ellsworth |
| 2010/0016946 A1 | 1/2010 | McDermott |
| 2010/0049297 A1 | 2/2010 | Dorn |
| 2010/0057182 A1 | 3/2010 | Pilz |
| 2010/0057185 A1 | 3/2010 | Melsheimer |
| 2010/0131049 A1 | 5/2010 | Perkins et al. |
| 2010/0168835 A1 | 7/2010 | Dorn |
| 2010/0204770 A1 | 8/2010 | Mas et al. |
| 2010/0292780 A1 | 11/2010 | Straubinger |
| 2010/0331619 A1 | 12/2010 | Miyoshi et al. |
| 2011/0009951 A1 | 1/2011 | Bogert |
| 2011/0015612 A1 | 1/2011 | Arcand et al. |
| 2011/0046712 A1 | 2/2011 | Melsheimer |
| 2011/0054552 A1 | 3/2011 | Takayama et al. |
| 2011/0060214 A1 | 3/2011 | Makower |
| 2011/0060397 A1 | 3/2011 | Dorn |
| 2011/0118802 A1 | 5/2011 | Usui |
| 2011/0155149 A1 | 6/2011 | Mauch |
| 2011/0208296 A1 | 8/2011 | Duffy |
| 2011/0257720 A1* | 10/2011 | Peterson .................. A61F 2/95 623/1.11 |
| 2011/0264191 A1 | 10/2011 | Rothstein |
| 2011/0270379 A1 | 11/2011 | Bruszewski |
| 2012/0035677 A1 | 2/2012 | Imabayashi et al. |
| 2012/0059454 A1 | 3/2012 | Millwee |
| 2012/0071824 A1 | 3/2012 | Chang et al. |
| 2013/0006055 A1 | 1/2013 | Goldfarb et al. |
| 2013/0023919 A1 | 1/2013 | Olivera |
| 2013/0030418 A1 | 1/2013 | Taft |
| 2013/0035739 A1 | 2/2013 | Goto |
| 2013/0090624 A1 | 4/2013 | Munsinger |
| 2013/0116770 A1 | 5/2013 | Robinson |
| 2013/0165873 A1 | 6/2013 | Morriss et al. |
| 2013/0231529 A1 | 9/2013 | Chang et al. |
| 2013/0253564 A1 | 9/2013 | Edgren et al. |
| 2013/0261388 A1 | 10/2013 | Jenkins et al. |
| 2013/0282113 A1 | 10/2013 | Punga et al. |
| 2013/0304196 A1 | 11/2013 | Kelly |
| 2013/0310780 A1 | 11/2013 | Phillips |
| 2013/0310781 A1 | 11/2013 | Phillips et al. |
| 2013/0324970 A1 | 12/2013 | Arcand et al. |
| 2014/0012075 A1 | 1/2014 | Konstorum |
| 2014/0031852 A1 | 1/2014 | Edgren et al. |
| 2014/0031917 A1 | 1/2014 | Thompson |
| 2014/0074140 A1 | 3/2014 | Johnson et al. |
| 2014/0074141 A1 | 3/2014 | Johnson et al. |
| 2014/0079755 A1 | 3/2014 | Eaton et al. |
| 2014/0107763 A1 | 4/2014 | Layne et al. |
| 2014/0107766 A1 | 4/2014 | Banas et al. |
| 2014/0144000 A1* | 5/2014 | Creaven .................. B23P 19/04 29/505 |
| 2014/0154236 A1 | 6/2014 | Hester et al. |
| 2014/0180384 A1 | 6/2014 | LeBlanc |
| 2014/0200444 A1 | 7/2014 | Kim et al. |
| 2014/0222144 A1 | 8/2014 | Eberhardt et al. |
| 2014/0276408 A1 | 9/2014 | Abbate |
| 2014/0276654 A1 | 9/2014 | Jenkins |
| 2014/0296898 A1 | 10/2014 | Chang et al. |
| 2014/0330372 A1 | 11/2014 | Weston et al. |
| 2014/0331475 A1 | 11/2014 | Duffy |
| 2014/0336693 A1 | 11/2014 | Goldfarb et al. |
| 2014/0336694 A1 | 11/2014 | Becker |
| 2015/0105849 A1 | 4/2015 | Cohen |
| 2015/0119974 A1 | 4/2015 | Rothstein |
| 2015/0196735 A1 | 7/2015 | Olig et al. |
| 2016/0278955 A1 | 9/2016 | Liu |
| 2016/0296352 A1 | 10/2016 | Ryan |
| 2017/0105854 A1* | 4/2017 | Treacy ..................... A61F 2/90 |
| 2017/0181853 A1 | 6/2017 | Rothstein |
| 2017/0290692 A1 | 10/2017 | Toner |
| 2018/0014957 A1 | 1/2018 | Harris |
| 2018/0185183 A1 | 7/2018 | Christakis |
| 2018/0214290 A1 | 8/2018 | Headley, Jr. |

* cited by examiner

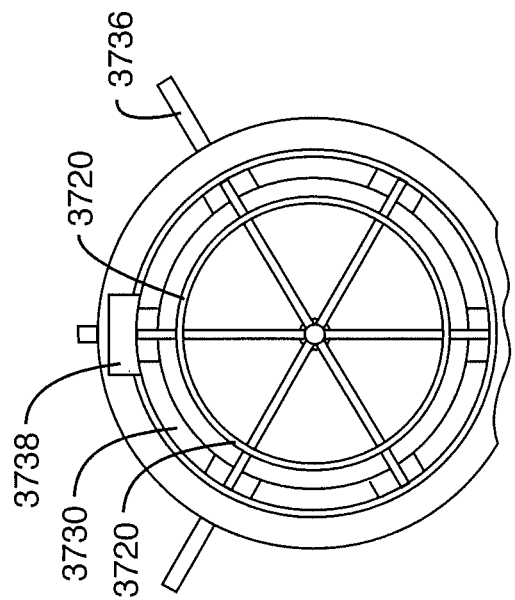
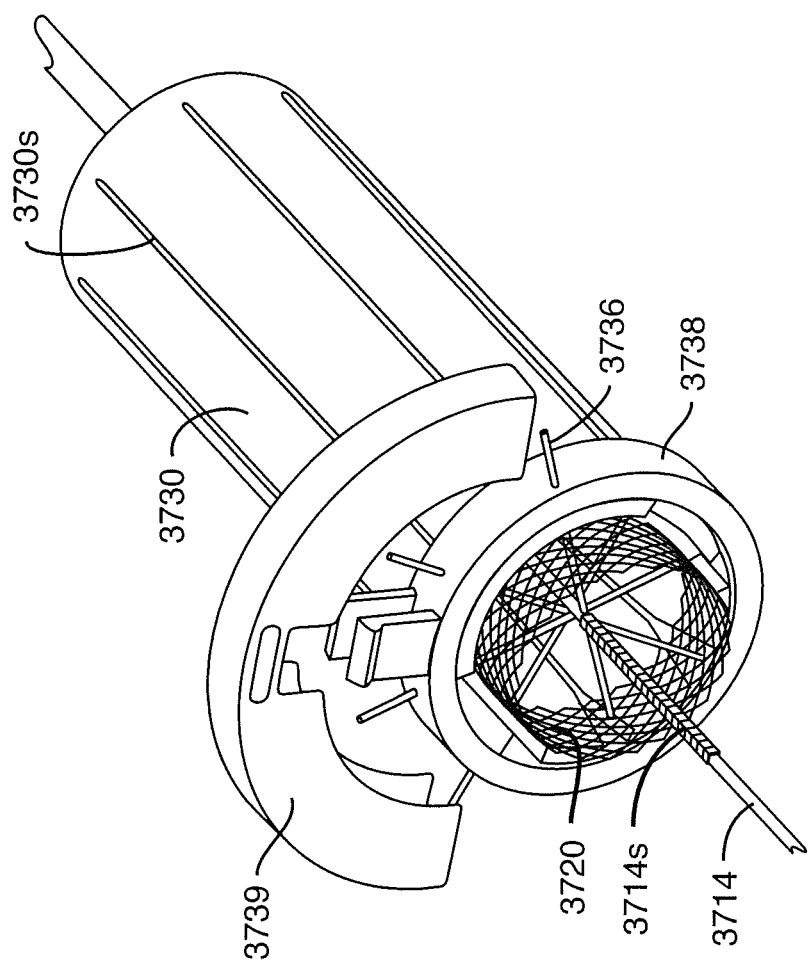
FIG. 37C
FIG. 37B

SCAFFOLD LOADING AND DELIVERY SYSTEMS

CROSS-REFERENCE TO RELATED APPLICATIONS

This application claims the benefit of U.S. Provisional Application Ser. No. 62/186,311 filed Jun. 29, 2015 and entitled SINUS SCAFFOLD DELIVERY SYSTEMS, U.S. Provisional Application Ser. No. 62/236,886 filed Oct. 3, 2015 and entitled SINUS SCAFFOLD DELIVERY SYSTEMS, and U.S. Provisional Application Ser. No. 62/314,239 filed Mar. 28, 2016 and entitled SINUS SCAFFOLD DELIVERY SYSTEMS, each of which is hereby incorporated by reference in its entirety.

FIELD OF THE DISCLOSURE

This disclosure describes, inter alia, materials, devices, kits and methods that may be used for loading scaffolds into delivery devices and for the delivery of scaffolds into the body of a patient, including delivery of scaffolds to the sinuses for the treatment of chronic sinusitis, among other purposes.

BACKGROUND

Chronic rhinosinusitis (CRS) is a common condition defined by symptomatic inflammation of the paranasal sinuses lasting longer than 12 weeks. Up to 16% of the population is affected by this condition. Cavities associated with CRS include the maxillary, frontal, ethmoid, ostiomeatal complex, ethmoid infundibulum and sphenoid sinuses as well as the middle meatus location, or a combination thereof. Common symptoms of CRS include impaired nasal obstruction, facial pressure or fullness, nasal discharge, and olfactory loss; these symptoms likely arise due to mucosal inflammation, local infection, and/or impairment of mucociliary function.

While there is no approved therapy for the treatment of CRS, evidence-based medical management supports the use of a host of oral or topical corticosteroid therapies for the disease. High-volume, daily saline irrigation with adjunct application of a topical corticosteroid via nasal sprays is common as a first-line therapy. Second line agents for flare-ups and worsening disease include a short course of oral corticosteroids, although this approach can lead to unintended systemic side effects including glaucoma, osteoporosis and avascular necrosis of the hip and shoulder. It is estimated that up to 12-50% of CRS patients do not respond positively to this recommended medical regimen and are often candidates for Functional Endoscopic Sinus Surgery (FESS) and/or balloon sinuplasty dilation.

Avoidance of surgical interventions in the treatment of CRS would be ideal for patients since these procedures carry surgery-associated risks, cause post-operative pain and discomfort, and require burdensome and costly post-operative cleaning. Clinical data has demonstrated that topical corticosteroids are effective in reducing inflammation associated with CRS and thus, are a rational choice for the management of this condition.

An ideal treatment for CRS would provide local and sustained anti-inflammatory drug delivery in the sinuses of patients as an alternative treatment option to sinus surgery. Such a therapy would ideally establish safe and effective sustained drug delivery localized to the inflamed tissue and in some cases could prevent the need for surgery.

In this regards, FESS involves removal of bone and tissue to enlarge sinus outflow tracts, widen sinus openings or ostia and allow for ventilation of previously obstructed sinus cavities and restoration of mucociliary clearance. Currently, there are approximately 500,000 procedures performed annually in the United States.

By removing small pieces of bone, polyps, and/or debridement of tissue within the sinus cavities, FESS has proven to be an effective way to improve the drainage pathway of the sinuses. However, a significant number of postoperative complications such as inflammation, swelling, disease recurrence, need for repeat procedures and synechiae are often observed. Postoperative care is therefore an important component of FESS. Approximately 10-20% of FESS patients become refractory, do not respond to treatment, and may require additional surgical intervention or lifelong medical therapy.

Some form of sinus packing is generally conducted postoperatively to FESS. Examples of packing materials include simple dressings moistened with saline, foam dressings based on polysaccharide gel, PEG-based materials, and middle meatal spacers. Implantable sinus stents have also been devised and these scaffolds are intended to stabilize the sinus openings and the turbinates, reduce edema, and/or prevent obstruction by tissue adhesion. They also have the capability of being integrated with therapeutic agent(s) that may be delivered topically over time. This local delivery of therapeutic agent(s) may be superior to topical application in the postoperative setting. In this regard, the USFDA-approved PROPEL™ system (Intersect ENT, Menlo Park, Calif., USA) is a self-expanding, bioresorbable, steroid-eluting stent that is intended for use in the ethmoid sinus post-FESS.

There is an ongoing need for improved devices and methods for loading and delivering scaffolds to the sinuses.

SUMMARY

In accordance with various aspects of the present disclosure, scaffold delivery systems are provided, which are useful for the loading and/or delivery of self-expanding scaffolds that comprise a scaffold wall and have a scaffold lumen, a proximal scaffold end, a distal scaffold end, an inner luminal surface, and an outer abluminal surface.

In some aspects, the delivery systems may comprise a first assembly and a second assembly, wherein (a) the first assembly comprises (i) a loading member that comprises a tapered loading lumen having a proximal loading lumen end and a distal loading lumen end, wherein the proximal loading lumen end has a first diameter and the distal loading lumen end has a second diameter that is smaller than the first diameter and (ii) a delivery sheath having a delivery sheath lumen that is connected to the loading lumen and (b) the second assembly comprises (i) the self-expanding scaffold, (ii) an elongate advancement member having a proximal end and a distal end, (iii) at least one filament linking an end of the elongate advancement member to the scaffold, and (iv) an elongate inner member having a proximal end and a distal end, wherein the elongate advancement member and elongate inner member may be the same or different. The second assembly is configured to be inserted into the proximal loading lumen end of the loading member and advanced at least partially through the first assembly, such that the scaffold is moved through the loading lumen in a proximal-to-distal direction.

In additional aspects, the delivery systems may comprise (a) a loading member that comprises a loading lumen having a lumen axis and a luminal surface, a plurality of longitudinal pathways being formed in the luminal surface of the loading member adjacent to the loading lumen, said loading lumen comprising a tapered lumen region having a proximal tapered lumen end with a first diameter and a distal tapered lumen end with a second diameter that is smaller than the first diameter, (b) the self-expanding scaffold disposed within the loading lumen, said scaffold comprising a scaffold wall and having a scaffold lumen, a proximal scaffold end, a distal scaffold end, an inner luminal surface, an outer abluminal surface, (c) an engagement device comprising an engagement device axis and a plurality of elongate members, which taper radially outward from the engagement device axis, which have a shape memory that allows the elongate members to be radially compressed and to self-expand after upon removal of radial compression, and which terminate in an engagement feature, wherein the engagement device is at least partially positioned within the scaffold lumen and loading lumen such that each engagement feature extends through the scaffold wall and into one of the longitudinal pathways and such that longitudinal movement of the engagement device is accompanied by longitudinal movement of the scaffold within the loading lumen. In various embodiments, the delivery systems further comprise (a) a delivery sheath comprising a delivery lumen in communication with the loading lumen and (b) an elongate inner member, wherein the elongate inner member and engagement device are configured such that elongate inner member engages and pushes the engagement device through the loading lumen and at least a portion of the delivery sheath.

In further aspects, scaffold delivery systems are provided for the delivery of self-expanding scaffolds that comprise a scaffold wall have a scaffold lumen, a proximal scaffold end, a distal scaffold end, an inner luminal surface, and an outer abluminal surface. The scaffold delivery systems may comprise (a) an elongate inner member, (b) a loading member that comprises a loading lumen having a loading lumen axis and a plurality of longitudinal pathways adjacent to the loading lumen, said loading lumen comprising a tapered lumen region having a proximal tapered lumen end with a first diameter and a distal tapered lumen end with a second diameter that is smaller than the first diameter, (c) the self-expanding scaffold disposed around the elongate inner member within the loading lumen and (d) a plurality of loading pins configured for engagement with the scaffold wall and for longitudinal movement along the longitudinal pathways, such that longitudinal movement of the loading pins along the longitudinal pathways is accompanied by longitudinal movement of the scaffold. In various embodiments, the delivery systems may further comprise a delivery sheath comprising a delivery lumen in communication with the loading lumen.

The above and numerous additional aspects of the present disclosure are enumerated in the following paragraphs:

Aspect 1. A crimping device configured to exert an inward radial force on a radially self-expandable scaffold and configured for detachable attachment to a distal end of a delivery sheath that comprises a delivery lumen, wherein the crimping device reduces an outer diameter of the radially self-expandable scaffold to a reduced outer diameter that is less than or equal to a diameter of the delivery lumen.

Aspect 2. The crimping device of aspect 1, wherein the crimping device comprises a collar band and a reducing mechanism that is configured to reduce the circumference of the collar band.

Aspect 3. The crimping device of aspect 2, wherein the collar-band-diameter reducing mechanism is a crank mechanism.

Aspect 4. The crimping device of any of aspect 1, wherein the crimping device comprises an inner lumen at least partially surrounded by an air bladder that is configured to be inflated to decrease a diameter of the inner lumen.

Aspect 5. A crimping system comprising (a) the crimping device of any of aspects 1-4 and (b) an elongate inner member having a shaft with an enlarged distal end or an elongate pusher member.

Aspect 6. A delivery system comprising (a) delivery sheath comprising a delivery lumen having a delivery lumen diameter and (b) a flexible tapered loading member comprising a first end which is larger than the delivery lumen diameter and which is configured to receive a radially self-expandable scaffold and a second end which is smaller than the delivery lumen diameter, wherein the flexible tapered loading member is configured to be inserted into the delivery lumen accompanied by a collapse of the flexible tapered loading member.

Aspect 7. The delivery system of aspect 6, wherein the flexible tapered loading member is a collapsible and expandable mesh.

Aspect 8. The delivery system of aspect 6, wherein the flexible tapered loading member is a funnel-shaped member.

Aspect 9. The delivery system of aspect 6, wherein the flexible tapered loading member is formed by cinching a filament at a distal end of a cylindrical member.

Aspect 10. A delivery system comprising (a) a delivery sheath comprising a delivery lumen, (b) a detachable funnel having a tapered lumen that is disposable at a distal end of the delivery sheath such that the tapered funnel lumen is in communication with the delivery lumen (c) a radially self-expandable scaffold and (d) an elongate loading member configured to transport the radially self-expandable scaffold through the funnel lumen and into the delivery lumen.

Aspect 11. The delivery system of aspect 10, wherein the elongate loading member is a flexible elongate member attached to an end of the radially self-expandable scaffold configured for pulling the radially self-expandable scaffold through the funnel and into the delivery lumen.

Aspect 12. The delivery system of aspect 10, further comprising a flexible braided mesh, wherein the braided mesh is configured to receive the radially self-expandable scaffold and to be transported through the funnel and into the delivery lumen.

Aspect 13. The delivery system of aspect 12, further comprising a flexible elongate member attached to an end of the flexible braided mesh configured for pulling the braided mesh and radially self-expandable scaffold through the funnel and into the delivery lumen.

Aspect 14. The delivery system of any of aspects 12-13, wherein the flexible braided mesh is a double-layered mesh.

Aspect 15. A delivery system comprising (a) a scaffold, (b) a delivery sheath comprising a delivery lumen, (c) an engagement device comprising a plurality of radially contractible members, each comprising an engagement feature at its distal end, wherein the engagement features are adapted to engage a proximal end of the scaffold and reduce an outer diameter of the proximal end of the scaffold as the engagement device is transported into the delivery lumen due to radial contraction of the radially contractible members.

Aspect 16. The delivery system of aspect 15 further comprising a detachable funnel disposable at a distal end of the delivery sheath.

Aspect 17. A catheter configured for access to a sinus of a patient, wherein the catheter comprises a sheath having a lumen and a shape-memorized section that displays a curvature when the sheath is in an unconstrained state.

Aspect 18. The catheter of aspect 17, wherein the shape-memorized section has a curvature that ranges, for example, from 0 to 135 degrees.

Aspect 19. The catheter of any of aspects 17-18, wherein the shape-memorized section has a curvature that ranges from 1 to 50 mm in length.

Aspect 20. The catheter of any of aspects 17-19, further comprising a linear elongate member configured for insertion into and removal from the lumen, wherein the linear elongate member is of sufficient stiffness such that said insertion results in the substantial elimination of said curvature.

Aspect 21. The catheter of any of aspects 17-20, (a) wherein the catheter is a delivery catheter and the sheath is a delivery sheath comprising a delivery lumen that is configured to deliver a radially self-expandable scaffold or (b) wherein the catheter is a guide catheter and the sheath is a guide catheter sheath comprising a guide lumen that is configured to receive a delivery catheter.

Aspect 22. A system comprising the delivery catheter of aspect 21 and a scaffold, wherein the scaffold is configured to be delivered from the delivery lumen and into a sinus ostia.

Aspect 23. A system comprising (b) a delivery catheter configured for access to a sinus of a patient, wherein the delivery catheter comprises a delivery lumen configured for delivery of a scaffold and (b) an elongate member comprising a shape-memorized section that has a curvature when the elongate member is in an unconstrained state, wherein the elongate member is of sufficient stiffness such that insertion of the elongate member results in curvature of the delivery catheter.

Aspect 24. The system of aspect 23, wherein the elongate member is configured to be custom bent, depending on user preference.

Aspect 25. A delivery catheter configured for access to a sinus of a patient, wherein the delivery catheter comprises a delivery sheath having a delivery lumen and wherein the delivery catheter has a stiffness gradient wherein stiffness decreases in a proximal-to-distal direction or wherein stiffness increases in a proximal-to-distal direction.

Aspect 26. A catheter configured for access to a sinus of a patient, wherein the catheter comprises (a) a sheath having a curvature and a lumen and (b) a handle comprising a mechanism whereby the sheath may be rotated relative to the handle.

Aspect 27. The catheter of aspect 26, wherein the catheter is a delivery catheter and the sheath is a delivery sheath, or wherein the catheter is a guide catheter and wherein the sheath is a guide sheath.

Aspect 28. A delivery catheter comprising an elongate inner member and a flexible outer sheath, wherein a distal end of the outer sheath is folded into itself forming a region of double outer sheath thickness at a distal end of the delivery system that comprises an inner layer and an outer layer, wherein the inner layer is connected to a distal end of the elongate inner member, wherein the region of double outer sheath thickness forms a delivery lumen that is dimensioned to receive a radially self-expandable scaffold, and wherein proximal movement of the outer sheath relative to the elongate inner member shortens the region of double thickness and the delivery lumen formed thereby.

Aspect 29. A system comprising a delivery device, a radially compressible scaffold and a filament holding the scaffold in a radially compressed state.

Aspect 30. The system of aspect 29, wherein the filament is used to secure an outer sheath at a distal end of the delivery device, said outer sheath containing said scaffold, and wherein pulling the filament in a proximal direction releases the portion of the outer sheath secured by the filament allowing the scaffold to expand.

Aspect 31. The system of aspect 29, wherein the filament is in the form of a knit that secures and maintains the scaffold in a compressed state at a distal end of the delivery system and wherein pulling the filament in a proximal direction releases the scaffold.

Aspect 32. The system of any of aspects 29-31, wherein the filament secures the scaffold in a radially contracted state on an elongate inner member which is optionally disposed within a lumen of an outer sheath.

Aspect 33. A system comprising a delivery device comprising a delivery lumen, a radially self-expandable scaffold and a loading member, wherein the scaffold is configured to be flattened and wrapped around the loading member and inserted into a delivery lumen of the delivery device, after which the loading member is disengaged from the scaffold.

Aspect 34. The system of aspect 33, wherein the loading member comprises a pair of tines.

Aspect 35. A delivery system comprising (a) a spiral scaffold having a distal end and a proximal end and (b) delivery catheter comprising (i) an outer member having a distal end and an outer member attachment feature proximate the outer member distal end and (ii) an inner member having a distal end and an inner member attachment feature proximate the inner member distal end, wherein the inner member attachment feature is adapted to become attached to the scaffold distal end and the outer member attachment feature is adapted to become attached to the scaffold proximal end and wherein, upon attachment of the inner member attachment feature to the scaffold distal end and attachment of the outer member attachment feature to the scaffold proximal end, rotation of the outer member relative to the inner member in a first direction results in contraction of the spiral scaffold and rotation of the outer member relative to the inner member in a second opposing direction results in expansion of the spiral scaffold.

Aspect 36. The delivery system of aspect 35, wherein the inner member attachment feature and the outer member attachment feature each comprise hooks.

Aspect 37. An anchoring device comprising a distal inflation balloon which is configured for inflation in a sinus cavity and a proximal flexible tracking member that is configured such that a loaded delivery system comprising a delivery catheter and a scaffold may be routed over the flexible tracking member.

Aspect 38. A delivery system comprising (a) a catheter configured for access to a sinus of a patient, wherein the catheter comprises a sheath having a first lumen, (b) an elongate pusher member having a second lumen, said elongate pusher member being configured for insertion into the first lumen, and (c) an elongate inner support member configured for insertion through the second lumen and running through the length of the system.

Aspect 39. The delivery system of aspect 38, wherein said sheath comprises a shape-memorized section that displays a curvature when the sheath is in an unconstrained state.

Aspect 40. The delivery system of any of aspects 38-39, wherein the elongate pusher member is formed from a single material or wherein the elongate pusher member is formed of multiple materials thereby varying in stiffness between its distal and proximal end.

Aspect 41. The delivery system of any of aspects 38-39, wherein the support member is formed from a single material or wherein the support member is formed of multiple materials thereby varying in flexibility between its distal and proximal end.

Aspect 42. The delivery system of any of aspects 38-41, wherein support member comprises a third lumen dimensioned to receive a guide wire.

Aspect 43. A crimping assembly configured to exert an inward radial force on a radially self-expandable scaffold comprising (a) a loading member comprising a first end having a first inside diameter, a second end having a second inside diameter that is smaller than said first diameter, and a tapered region between the first end and the second end providing a transition between the first and second inside diameters (b) and a pusher member comprising a hollow cylindrical end having an unconstrained outside diameter that is substantially equal to the first inside diameter such that the pusher member can be inserted into the first end of the loading member, said pusher member having a plurality of slots forming a plurality of projections at the hollow cylindrical end and being configured such that the outside diameter of the hollow cylindrical end can be reduced from said unconstrained outside diameter to an outside diameter that is substantially equal to the second inside diameter when the cylindrical end is advanced from the first end to the second end through the tapered region.

Aspect 44. A delivery device comprising (a) an elongate delivery member having proximal end and a distal end that comprises a pocket having an inner width and configured to receive a scaffold in a contracted state, (b) an expulsion member having an outer width that is substantially equal to the inner width of the pocket and configured to be positioned in the pocket proximal to the scaffold when the scaffold is positioned in the pocket in the contracted state and (c) at least one filament having a first end and a second end, the at least one filament attached to the expulsion member at the first end and being routed out of pocket at the distal end of the elongate delivery member and proximally along or within the elongate delivery member such that proximally pulling the second end of the at least one filament causes the expulsion member to move distally in the pocket, leading to the distal expulsion of said scaffold when said scaffold is positioned in the pocket in the contracted state.

Aspect 45 A delivery system comprising (a) a braided scaffold having a distal end and a proximal end and (b) delivery device comprising (i) an elongate outer member having proximal end and a distal end and an outer member attachment feature proximate the elongate outer member distal end and (ii) an elongate inner member having a proximal end and a distal end and an inner member attachment feature proximate the elongate inner member distal end, wherein the inner member attachment feature is adapted to become attached to the distal end of the scaffold and the outer member attachment feature is adapted to become attached to the proximal end of the scaffold and wherein, upon attachment of the inner member attachment feature to the distal end of the scaffold and attachment of the outer member attachment feature to the proximal end of the scaffold, distally advancing the inner member relative to the outer member results in contraction of the scaffold while proximally retracting the inner member relative to the outer member results in expansion of the scaffold.

Aspect 46. The delivery system of aspect 45, wherein the inner and outer attachment features comprise hooks.

Aspect 47. A delivery system comprising (a) a delivery device comprising (i) an elongate outer member having a proximal end and a distal end and (ii) an elongate inner member disposed within the elongate outer member, said elongate inner member having a proximal end and a distal end and having a scaffold support segment positioned at or near the distal end of the elongate inner member and (b) a self-expanding scaffold disposed between the elongate outer member and the scaffold support segment, said elongate outer member maintaining the scaffold in a compressed state on said scaffold support segment, wherein a first force of friction between contacting materials of the scaffold and the inner support segment is greater than a second force of friction between contacting materials of the scaffold and the elongate outer member, such that distally advancing the elongate inner member relative to the elongate outer member leads to expulsion of the scaffold from a distal end of the elongate outer member and, optionally, such that proximally retracting the elongate inner member relative to the elongate outer member when the stent is partially deployed leads to withdrawal of the scaffold into the distal end of the elongate outer member.

Aspect 48. The delivery system of aspect 47, further comprising a guide catheter having a lumen through which the delivery catheter can be advanced to a target site in a subject.

Aspect 49. A delivery system comprising an elongate delivery member having a proximal end and a distal end, a scaffold disposed over the elongate delivery member at or near the distal end of the elongate delivery member, and a an elongate containment member having a proximal end and a distal end that at least partially extends around a circumference of the elongate delivery member, said elongate containment member disposed over the scaffold thereby maintaining the scaffold in a compressed state.

Aspect 50. The delivery system of aspect 49, wherein the elongate containment member is an elongate outer member that fully extends around a circumference of the elongate delivery member.

Aspect 51. The delivery system of aspect 49, wherein the elongate containment member is an elongate containment sheath that does not fully extend around a circumference of the elongate delivery member.

Aspect 52. The delivery system of aspect 51, wherein the elongate containment sheath comprises a pull tab at or near the proximal end of the containment sheath.

Aspect 53. The delivery system of any of aspects 49-52, wherein the elongate delivery member comprises a distal tip and a region of reduced diameter forming a recess immediately proximal to the enlarged distal tip, and wherein the scaffold is disposed within said recess.

Aspect 54. The delivery system of aspect 49, wherein the elongate delivery member is a balloon catheter comprising an elongate catheter shaft and a balloon.

Aspect 55. The delivery system of any of aspects 49-54, further comprising an elongate inner member, wherein the elongate delivery member and elongate containment member are configured to be advanced over the elongate inner member to a targeted delivery site.

Aspect 56. The delivery system of aspect 55, wherein the elongate inner member is configured to provide access to a sinus cavity.

Aspect 57. The delivery system of any of aspects 55-56, wherein the elongate delivery member is a balloon catheter comprising an elongate catheter shaft and a balloon.

Aspect 58. The delivery system of aspect 57, wherein the scaffold is disposed over the balloon.

Aspect 59 The delivery system of aspect 57, wherein the scaffold is positioned distal to the balloon and wherein the elongate containment member is configured to allow inflation of the balloon while maintaining the elongate containment member over the scaffold in a compressed state.

Aspect 60. A delivery system comprising (a) an elongate inner member having a distal end and configured to provide access to a sinus cavity and (b) a balloon catheter assembly comprising (i) an elongate catheter shaft, (ii) a balloon in the form of a hollow annulus having a proximal end, a distal end, and a central balloon lumen, (iii) an inner ring having a central ring lumen disposed in a proximal portion of the central balloon lumen, and (iv) a self-expanding scaffold disposed in the central balloon lumen at a position distal to the ring, wherein the balloon catheter is configured to be advanced over the elongate inner member to a target position, to inflate and deflate the balloon at the target position, and to release the scaffold at the target position.

Aspect 61. A delivery system comprising (a) a delivery member comprises an elongate inner member, a surrounding portion, and a distal tip, wherein the elongate inner member and the surrounding portion form an annular cavity having proximal and distal ends, (b) an elongate intermediate member disposed over at least a portion of the elongate inner member, a distal end of the elongate intermediate member disposed within the annular cavity and (c) a self-expanding scaffold disposed within the annular cavity between an outer surface of the elongate intermediate member and radially-inward-facing surface of the annular cavity of the surrounding portion, wherein proximally retracting the elongate intermediate member relative to the delivery member leads to delivery of the scaffold through the proximal end of the annular cavity.

Aspect 62. The delivery system of aspect 61, wherein the surrounding portion maintains the scaffold in a compressed state on the elongate intermediate member and wherein, as a result of a first force of friction between contacting materials of the scaffold and the elongate intermediate member being greater than a second force of friction between contacting materials of the scaffold and the surrounding portion, proximally retracting the elongate intermediate member relative to the delivery member leads to delivery of the scaffold from the proximal end of the annular cavity and, optionally, distally advancing the elongate intermediate member relative to the delivery member when the scaffold is partially deployed leads to the withdrawal of the scaffold into the proximal end of the annular cavity.

Aspect 63. The delivery system of aspect 61, wherein the scaffold is attached to the elongate intermediate member by at least one temporary attachment feature such that that proximally retracting the elongate intermediate member relative to the surrounding portion leads to the expulsion of the scaffold from the proximal end of the surrounding portion.

Aspect 64. The delivery system of any of aspects 61-63, further comprising a delivery sheath having a distal end, wherein the elongate inner member and the elongate intermediate member extend proximally into a lumen of the delivery sheath.

Aspect 65. The delivery system of aspect 64, wherein retraction of the elongate inner member relative to the delivery sheath results in a proximal end of the surrounding portion abutting the distal end of the delivery sheath, and wherein advancement of the elongate inner member relative to the delivery sheath results in a gap between the proximal end of the surrounding portion and the distal end of the delivery sheath through which the scaffold is expanded and released.

Aspect 66. The delivery system of aspect 64, wherein the surrounding portion is in the shape of a hollow cylinder.

Aspect 67. A delivery system comprising (a) an elongate inner member, (b) a loading member that comprises a loading lumen having a loading lumen axis and a plurality of longitudinal pathways adjacent to the loading lumen, said loading lumen comprising a tapered lumen region having a proximal tapered lumen end with a first diameter and a distal tapered lumen end with a second diameter that is smaller than the first diameter, (c) a self-expanding scaffold disposed around the elongate inner member within the loading lumen, said scaffold comprising a scaffold wall and having a proximal scaffold end, a distal scaffold end, an inner luminal surface, an outer abluminal surface, (d) a plurality of loading pins configured for engagement with the scaffold wall and for longitudinal movement along the longitudinal pathways, such that longitudinal movement of the loading pins along the longitudinal pathways is accompanied by longitudinal movement of the scaffold, and (e) optionally, a delivery sheath comprising a delivery lumen in communication with the loading lumen, said delivery lumen having a delivery lumen diameter.

Aspect 68. The delivery system of aspect 67, wherein the first diameter is greater than or equal to an unconstrained diameter of the scaffold and wherein the second diameter is less than or equal to the delivery lumen diameter.

Aspect 69. The delivery system of any of aspects 67-68, wherein the longitudinal pathways comprise slots.

Aspect 70. The delivery system of any of aspects aspect 67-69, wherein the plurality of loading pins extend through the scaffold wall and into the elongate inner member, and wherein the delivery system is configured such that the longitudinal movement of the loading pins along the longitudinal pathways results in longitudinal movement of the elongate inner member and the scaffold.

Aspect 71. The delivery system of aspect 70, wherein the plurality of loading pins extend through a first aperture in the scaffold wall, through the elongate inner member and through a second aperture in the scaffold wall opposite the first aperture the scaffold wall.

Aspect 72. The delivery system of any of aspects 67-71, further comprising a removable packaging feature that engages the loading pins and the loading member such that the loading pins are held in place within the loading member.

Aspect 73. The delivery system of any of aspects 67-72, further comprising an inner member engagement member that is configured to reversibly engage and distally advance the elongate inner member.

Aspect 74. The delivery system of aspect 73, wherein the inner member engagement member at least partially surrounds the elongate inner member and wherein the engagement member is longitudinally moveable along a portion of the elongate inner member length.

Aspect 75. The delivery system of any of aspects 73-74, and wherein the elongate inner member comprises a stop that limits axial movement of the inner member engagement member relative to the elongate inner member.

Aspect 76. The delivery system of any of aspects 67-75, wherein the delivery system comprises a loading pin engagement member that is configured to reversibly engage and distally advance the loading pins.

Aspect 77. The delivery system of aspect 76, wherein the loading pin engagement member is a ring-shaped member.

Aspect 78. The delivery system of aspect 77, further comprising a removable packaging feature that engages the loading pins and the loading pin engagement member such that the loading pins are held in place within the loading member.

Aspect 79. The delivery system of any of aspects 67-75, wherein the loading pins maintain a constant radial distance from the loading lumen axis when moved distally over a first portion of the longitudinal pathways and wherein the loading pins increase in radial distance from the loading lumen axis when moved distally over a second portion of the longitudinal pathways that is distal to the first portion of the longitudinal pathways, such that the loading pins become disengaged from the scaffold.

Aspect 80. The delivery system of aspect 79, wherein the passageways comprise slots that engage the loading pins and disengage the loading pins from the scaffold.

Aspect 81. The delivery system of any of aspects 67-75, wherein the loading pins are configured to be disengaged manually from the scaffold.

Aspect 82. The delivery system of any of aspects 67-81, comprising a finger-operated slide or wheel that distally advances the loading pins, the elongate inner member or both.

Aspect 83. A delivery system comprising, (a) a loading member that comprises a loading lumen having a lumen axis and a luminal surface, a plurality of longitudinal pathways being formed in the luminal surface of the loading member adjacent to the loading lumen, said loading lumen comprising a tapered lumen region having a proximal tapered lumen end with a first diameter and a distal tapered lumen end with a second diameter that is smaller than the first diameter, (b) a self-expanding scaffold disposed within the loading lumen, said scaffold comprising a scaffold wall and having a scaffold lumen, a proximal scaffold end, a distal scaffold end, an inner luminal surface, an outer abluminal surface, (c) an engagement device comprising an engagement device axis and a plurality of elongate members, which taper radially outward from the engagement device axis, which have a shape memory that allows the elongate members to be radially compressed and to self-expand after upon removal of radial compression, and which terminate in an engagement feature, wherein the engagement device is at least partially positioned within the scaffold lumen and loading lumen such that each engagement feature extends through the scaffold wall and into one of the longitudinal pathways and such that longitudinal movement of the engagement device is accompanied by longitudinal movement of the scaffold within the loading lumen.

Aspect 84. The delivery system of aspect 83, wherein the longitudinal pathways comprise grooves.

Aspect 85. The delivery system of aspect 84, wherein the grooves have a depth that gradually diminishes as one approaches the distal tapered lumen end.

Aspect 86. The delivery system of any of aspects 83-85, further comprising a delivery sheath comprising a delivery lumen in communication with the loading lumen, said delivery lumen having a delivery lumen diameter.

Aspect 87. The delivery system of aspect 86, wherein the first diameter is greater than or equal to an unconstrained diameter of the scaffold and wherein the second diameter is less than or equal to the delivery lumen diameter.

Aspect 88. The delivery system of any of aspects 86-87, further comprising an elongate inner member, wherein the elongate inner member and engagement device are configured such that elongate inner member engages and advances the engagement device through the loading lumen and at least a portion of the delivery sheath.

Aspect 89. The delivery system of any of aspects 83-88, wherein the engagement device further comprises an elongate shaft and wherein the plurality of elongate members extend from and taper radially outward from an end of the elongate shaft.

Aspect 90. The delivery system of aspect 89, wherein the elongate shaft is an elongate tubular shaft having a proximal end, a distal end, and a tubular shaft lumen, and wherein the plurality of elongate members extend through at least a portion of the tubular shaft lumen and taper radially outward from the proximal end of the elongate tubular shaft.

Aspect 91. The delivery system of aspect 90, wherein the engagement device further comprises a cap that is disposed over the distal end of the elongate tubular shaft and wherein an end of each elongate member that is opposite the engagement feature is attached to the cap, such that disengaging and pulling the cap from the elongate tubular shaft allows the elongate members to be pulled through the elongate tubular shaft and removed from the delivery system.

Aspect 92. A delivery system comprising, (a) a first assembly comprising (i) a loading member that comprises a tapered loading lumen having a proximal loading lumen end and a distal loading lumen end, wherein the proximal loading lumen end has a first diameter and the distal loading lumen end has a second diameter that is smaller than the first diameter and (ii) a delivery sheath having a delivery sheath lumen that is connected to the loading lumen, and (b) a second assembly comprising (i) a self-expanding scaffold, said scaffold comprising a scaffold wall and having a scaffold lumen, a proximal scaffold end, a distal scaffold end, an inner luminal surface, and an outer abluminal surface, (ii) an elongate advancement member having a proximal end and a distal end, (iii) at least one filament linking an end of the elongate advancement member to the scaffold, and (iv) an elongate inner member having a proximal end and a distal end, wherein the elongate advancement member and elongate inner member may be the same or different, wherein the second assembly is configured to be inserted into the proximal loading lumen end of the loading member and advanced at least partially through the first assembly, such that the scaffold is moved through the loading lumen in a proximal-to-distal direction.

Aspect 93. The delivery system of aspect 92, wherein the first assembly further comprises a handle having a handle lumen disposed between the loading member and delivery sheath, and wherein the loading lumen is in communication with the delivery sheath lumen through the handle lumen.

Aspect 94. The delivery system of aspect 93, wherein the loading member is in the form of a funnel and wherein either the funnel is detachable from the handle or wherein the funnel and handle are integrated into a single article.

Aspect 95. The delivery system of any of aspects 92-94, wherein the elongate inner member and the elongate advancement member are the same, wherein the scaffold is held in position over the distal end of the inner member by the at least one filament, and wherein the second assembly is advanced at least partially through the first assembly by pushing the elongate inner member from a proximal end of the first assembly.

Aspect 96. The delivery system of aspect 95, wherein the second assembly further comprises a press member that can be pushed by an operator, and wherein the proximal end of the elongate inner member is inserted into the press member.

Aspect 97. The delivery system of any of aspects 95-96, wherein at least one filament is looped from the distal end of the elongate inner member, through at least one aperture in the scaffold wall, and back to the distal end of the elongate inner member.

Aspect 98. The delivery system of any of aspects 95-96, wherein the elongate inner member comprises a lumen that extends from a proximal end of the elongate inner member to a distal end of the elongate inner member.

Aspect 99. The delivery system of aspect 98, wherein at least one filament is looped into the elongate inner member lumen at a proximal position, through the elongate inner member lumen, out of the elongate inner member lumen at a distal position, through at least one aperture in the scaffold wall, back into the elongate inner member lumen at a distal position, through the elongate inner member lumen, and out of the elongate inner member lumen at a proximal position.

Aspect 100. The delivery system of aspect 98, wherein at least one filament is looped from a filament holder, into the elongate inner member lumen at a proximal position, through the elongate inner member lumen, out of the elongate inner member lumen at a distal position, through at least one aperture in the scaffold wall, and back into the elongate inner member lumen at a distal position, through the elongate inner member lumen, out of the elongate inner member lumen at a proximal position, and back to the filament holder.

Aspect 101. The delivery system of aspect 100, wherein the filament holder comprises first and second portions that are separable from one another, wherein a first end of the at least one filament is connected to the first portion, and wherein a second end of the at least one filament is connected to the second portion.

Aspect 102. The delivery system of aspect 92, wherein the elongate inner member and the elongate advancement member are different, wherein the elongate advancement member is positioned distal to the elongate inner member, wherein at least one filament links the scaffold to the elongate advancement member.

Aspect 103. The delivery system of aspect 102, wherein the second assembly is advanced at least partially through the first assembly by pulling the elongate advancement member from a distal end of the first assembly.

Aspect 104. The delivery system of aspect 103, wherein at least one filament further links a distal end of the elongate inner member to a proximal end of the elongate advancement member.

Aspect 105. The delivery system of aspect 103, wherein at least one filament is looped from the proximal end of the elongate advancement member, through at least one aperture in the scaffold wall, and back to the proximal end of the elongate advancement member.

Aspect 106. The delivery system of aspect 105, wherein at least one filament is further looped through the distal end of the elongate inner member.

Aspect 107. The delivery system of aspect 103, wherein the elongate advancement member comprises a lumen that extends from a distal end of the elongate advancement member to a proximal end of the elongate advancement member.

Aspect 108. The delivery system of aspect 107, wherein the at least one filament is looped into the elongate advancement member lumen at a distal position, through the elongate advancement member lumen, out of the elongate advancement member lumen at a proximal position, through at least one aperture in the scaffold wall, back into the elongate advancement member lumen at a proximal position, through the elongate advancement member lumen, and out of the elongate advancement member lumen at a distal position.

Aspect 109. The delivery system of any of aspects 102, wherein the second assembly is configured to be advanced at least partially through the first assembly by applying force to the proximal end of the elongate advancement member.

Aspect 110. The delivery system of aspect 109, wherein (a) the distal end of the elongate inner member is configured to engage the proximal end of the elongate advancement member or (b) the elongate inner member is hollow and has a lumen, and wherein the second assembly further comprises additional elongate member having a proximal end and a distal end that is configured to extend through the lumen of the inner elongate member and engage the proximal end of the elongate advancement member.

Aspect 111. The delivery system of aspect 110, wherein a receptacle is provided at a proximal end of the elongate advancement member that is configured to receive the distal end of the elongate inner member or to receive the distal end of the additional elongate member.

Aspect 112. The delivery system of any of aspects 109-111, wherein at least one filament is looped from the elongate advancement member, through at least one aperture in the scaffold wall, and back to the elongate advancement member.

Aspect 113. The delivery system of aspect 112, wherein both ends of the at least one filament are adhered to the elongate advancement member.

Aspect 114. The delivery system of aspect 113, wherein the elongate advancement member comprises a groove and wherein one end of the at least one filament is positioned in the groove so that the one end can be cut and severed from the elongate advancement member.

Aspect 115. The delivery system of aspect 112, wherein the elongate advancement member comprises two portions that are configured to be reversibly joined.

Aspect 116. The delivery system of aspect 115, wherein the two portions are joined together, wherein one end of the at least one filament is adhered to one of the two portions, and wherein an opposite end of the at least one filament is trapped between the two portions.

Aspect 117. The delivery system of any of aspects 92-116, further comprising a delivery catheter having a proximal end and a distal end and configured for insertion into a patient, wherein the distal end of the delivery sheath is configured for attachment to the proximal end of the delivery catheter subsequent to insertion of the delivery catheter into a patient.

These and other aspects, embodiments and benefits of the present disclosure will become immediately apparent to those of ordinary skill in the art upon review of the detailed description and claims to follow.

BRIEF DESCRIPTION OF THE FIGURES

FIG. 37B is a schematic perspective view of components of FIG. 37A. FIG. 37C is a schematic end view of components of FIG. 37A.

DESCRIPTION

Figure 1:
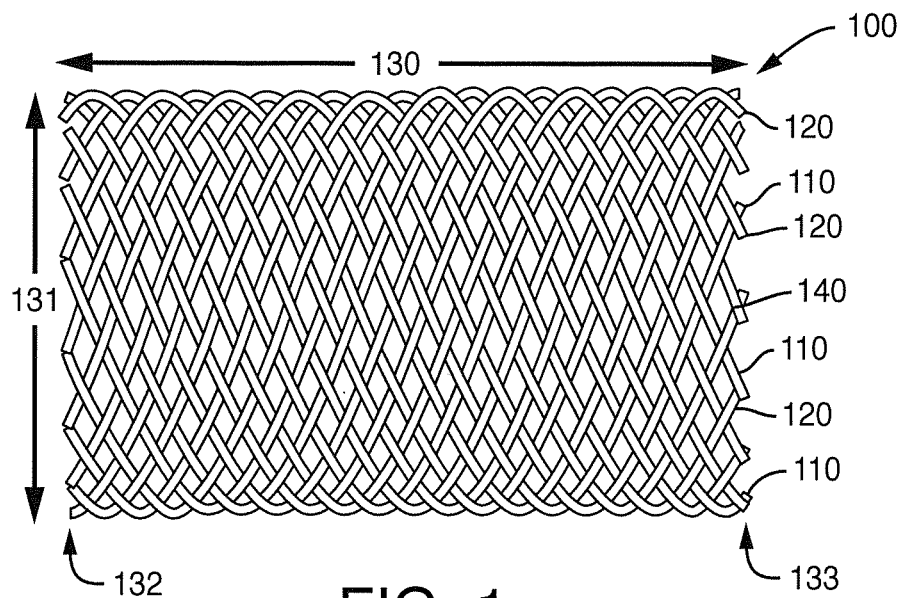
FIG. 1 is a schematic side view of an implantable scaffold, in accordance with an embodiment of the present disclosure.

The implantable medical devices delivered by the delivery devices of the present disclosure are generally tubular devices, which devices are self-expanding devices in various embodiments. As used herein, "device," "scaffold," "stent" and "implant" may be used synonymously. Also as used herein, "self-expanding" is intended to include devices that are crimped to a reduced delivery configuration for delivery into the body, and thereafter tend to expand to a larger suitable configuration once released from the delivery configuration. As used herein "strands" and "filaments" may be used interchangeably and include single fiber strands and filaments (also referred to as monofilaments) and multi-fiber strands and filaments. As used herein a "tube," "hollow member," "catheter" and "tubular member" may be used synonymously.

As used herein, terms "sinus" and "sinus cavity" refer to both sinus cavities and nasal cavities, which include, for example, the maxillary, frontal and ethmoid sinuses, the ostiomeatal complex, the ethmoid infundibulum and the sphenoid sinuses as-well as the middle meatus (a sinus cavity).

Scaffolds for use in conjunction with the present disclosure are typically tubular devices which may be of various sizes, including a variety of diameters and lengths, and which may be used for a variety of medical applications including sinus applications. In the case of objects of non-circular cross-section, "diameter" denotes width. In certain beneficial embodiments, the as-manufactured (or unconstrained) diameter of the scaffold may range from 5 mm or less to 40 mm or more, for example, ranging from 5 mm to 10 mm to 15 mm to 20 mm to 25 mm to 30 mm to 35 mm to 40 mm (i.e., ranging between any two of the preceding numerical values), commonly ranging from 5 to 12 mm or from 15 to 30 mm. In certain beneficial embodiments, the as-manufactured (or unconstrained) length may range from 5 mm or less to 30 mm or more, for example, ranging from 5 mm to 10 mm to 15 mm to 20 mm to 25 mm or 30 mm (i.e., ranging between any two of the preceding numerical values), commonly ranging from 8 to 12 mm or from 15 mm to 30 mm. In various embodiments a drug or other therapeutic agent may be released from the scaffold for an extended period.

Various scaffold embodiments of the present disclosure are self-expanding in that they are manufactured at a first diameter, subsequently reduced or "crimped" to a second, reduced diameter for placement within a delivery catheter, and self-expand towards the first diameter when extruded from the delivery catheter at an implantation site. The first diameter may be at least 10% larger than the diameter of the bodily lumen into which it is implanted in some embodiments. The scaffold may be designed to recover at least about 70%, at least about 80%, at least about 90%, up to about 100% of its manufactured, first diameter, in some embodiments. Scaffolds in accordance with the present disclosure are provided with expansion and mechanical properties suitable to render the scaffolds effective for their intended purposes, including placement in the sinus cavities.

Scaffolds for use in the present disclosure may be formed from a variety of polymeric and non-polymeric materials. Scaffolds for use in the present disclosure may be biodegradable or non-biodegradable, or be a combination of both biodegradable and non-biodegradable materials. In various embodiments, the implantable scaffolds may comprise a generally tubular structure comprising scaffolding material. Scaffolds for use in the present disclosure may be fiber-based or non-fiber-based.

In various embodiments, the scaffolding material may be a biodegradable scaffolding material, typically, a biodegradable scaffolding material that comprises one or more biodegradable polymers. Non-limiting examples of biodegradable polymers for forming the biodegradable scaffolding material include biodegradable polyesters, polycarbonates, polyhydroxyalkanoates, polyanhydrides, and polyorthoesters. In various embodiments, the scaffolding material may be a non-biodegradable scaffolding material, typically a non-biodegradable scaffolding material that comprises one or more non-biodegradable polymers. Non-limiting examples of non-biodegradable polymers for forming the non-biodegradable scaffolding material include polyolefins, halogenated polyolefins, fluoropolymers, polyesters such as polyethylene terephthalate (PET), polyamides such as nylon, silicones, biostable polyurethanes (PU).

Scaffolds for use in the present disclosure may optionally comprise a coating formed of a coating material that at least partially coats the scaffolding material. Coatings may be applied for various purposes including mechanical property enhancement, degradation control, and therapeutic agent release and control.

In various embodiments, scaffolds for use in the present disclosure are braided scaffolds. For example, single-fiber strands and/or multi-fiber strands may be braided into a generally tubular structure. FIG. 1 illustrates an embodiment of a braided scaffold 100, which comprises at least one strand (e.g., a single-fiber or multi-fiber strand) woven to form a substantially tubular configuration having a length 130, a width 131, and first and second ends 132, 133 along the longitudinal dimension. For example, the tubular structure may comprise two sets of strands 110 and 120, with each set extending in an opposed helical configuration along the longitudinal dimension of the scaffold. In certain embodiments, the number of helical strands forming the scaffold may range, for example, from 8 to 48 strands, among other possibilities. The sets of strands 110 and 120 cross each other at a braid angle 140. The braid angle 140 may range, for example, from about 30 degrees or less to about 150 degrees or more, among other values.

The strands that form the braided scaffolds may vary widely in diameter, ranging, for example, from 10 to 1000 µm, among other possibilities.

In various other embodiments, scaffolds for use in the present disclosure may be in a spiral (e.g., helical) form. In some of these embodiments, a spiral form may be formed from a single strand (e.g., a single- or multi-fiber strand). In other of these embodiments, a spiral form may be formed from multi-stranded constructs. Examples of multi-stranded constructs include, for example, substantially two-dimensional structures (e.g., ribbon-shaped structures) which can be shaped into a spiral form.

Other examples of scaffolds include those described in "IMPLANTABLE SCAFFOLDS FOR TREATMENT OF SINUSITIS," Ser. No. 62/186,030, filed on Jun. 29, 2015, which is hereby incorporated by reference.

Scaffolds such as those described above, among others, may be loaded into a suitable delivery device for subsequent delivery to a patient by numerous methods, devices and systems as described in more detail below.

To facilitate low-profile aspects of the present disclosure (e.g., the delivery of the scaffolds into small diameter cavities, including small diameter sinus cavities), in certain beneficial embodiments, the strands used in forming scaffolds may have a diameter ranging from 100 to 500 µm, more beneficially ranging from 100 to 200 µm. The use of small diameter strands results in a scaffold with minimal wall thickness and the ability to collapse (i.e., to be crimped) within low diameter catheter delivery systems. In certain embodiments, the diameters of strands may be chosen so as to render the scaffold deliverable from a 18 French delivery catheter or smaller, from a 9 French delivery catheter or smaller, from a 6 French delivery catheter or smaller, or even from a from a 4 French delivery catheter or smaller, with a 6-9 French catheter being typical.

For instance, as one specific example, a scaffold ranging from 15 to 30 mm in expanded diameter, more typically 16 to 24 mm in expanded diameter, among other values, and 16 to 30 mm in length, among other values, may be implanted (e.g., using a 2-4 mm diameter delivery catheter, among other devices) into the vacated space that is formed during an ethmoidectomy. Where drug is released, in non-refractory patients the drug may be released over a period of 3 to 6 weeks, among other time periods, whereas in refractory patients the drug may be released over a period of 8 to 12 weeks, among other time periods.

As another specific example, a scaffold ranging from 6 to 20 mm in diameter, among other values, and 8 to 30 mm in length, among other values, may be implanted (e.g., using a 2-4 mm diameter delivery catheter, among other possible devices) into the middle meatus space. Where drug is released, it may be released over a period of 8 to 12 weeks, among other time periods.

As another specific example, a scaffold ranging from 6 to 10 mm in diameter, among other values, and 8 to 12 mm in length, among other values, may be implanted (e.g., using a 2-4 mm diameter delivery catheter, among other possible devices) into the sinus ostia (frontal, maxillary, or sphenoid) or the frontal sinus recess. Where drug is released, it may be released over a period of 6 to 12 weeks, among other time periods.

Thus, in various aspects, the present disclosure describes the use of delivery systems to provide access and positional placement of self-expanding scaffolds in the sinus space to treat patients. In various embodiments, this includes crimping and/or loading the scaffold in a suitable delivery device, accessing the appropriate location within the anatomy via the delivery device, and deploying the loaded scaffold from the delivery device into the target location. In this regard, the following categories will be discussed herein: (a) crimping and loading solutions for the scaffold, (b) delivery system design concepts, and (c) combination/adjunct delivery concepts.

It should be noted that, although many embodiments are described herein in conjunction with loading and delivery of scaffolds to the sinuses, the present disclosure is not so limited, with many embodiments described herein useful in conduction with delivery to other body cavities and lumens including the vasculature, urinary tract, gastrointestinal tract, and lungs, among other applications.

Figure 2A:
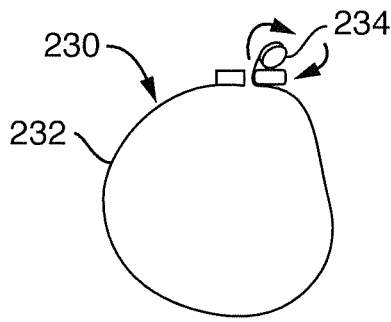
FIG. 2A is a schematic end view of a crimping device, in accordance with an embodiment of the present disclosure.
Figure 2B:
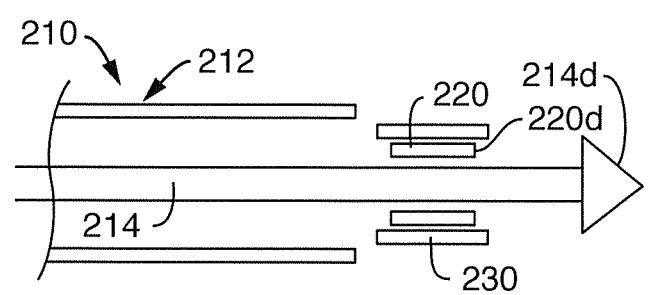
FIG. 2B is a schematic partial cross-sectional view of a system useful for crimping and loading a scaffold into a delivery catheter, in accordance with an embodiment of the present disclosure.

With regard to crimping and loading solutions for the scaffold, and with reference to FIGS. 2A-2B, in some embodiments, a crimping device 230 may be provided which is configured to exert an inward radial force on a radially self-expandable scaffold 220 and also configured for detachable attachment to a distal end of a delivery catheter 210 that comprises a delivery sheath having a delivery lumen. The crimping device reduces an outer diameter of the radially self-expandable scaffold 220 to a reduced outer diameter that is less than or equal to a diameter of the delivery lumen.

Turning in particular to FIG. 2A, the crimping device 230 may comprise a collar band 232 and a diameter reducing mechanism such as a crank 234 or other mechanism that is configured to reduce the circumference of the collar band 232.

In some embodiments, a system like that shown in FIG. 2B is provided, in which the delivery catheter 210 further comprises an elongate inner member 214 comprising a shaft with an enlarged distal end 214d, wherein the enlarged distal end 214d has an outer diameter that is less than or equal to the reduced outer diameter of the scaffold 220, while also being greater than an inner diameter of the scaffold 220 (so as to be able to engage the scaffold 220 without engaging the crimping device 230 upon retraction). In use, the enlarged distal end 214d of the inner member 214 is positioned distal to the crimping device 230, which may be attached (not shown) to the delivery sheath 212. When the inner member 214 of the delivery catheter 210 is retracted proximally, it engages a distal end 220d of the reduced diameter scaffold 220. Upon continued retraction of the inner member 214, the enlarged distal end 214d pulls the scaffold 220 proximally from the crimping device into the lumen of the delivery sheath 212.

Figure 3A:
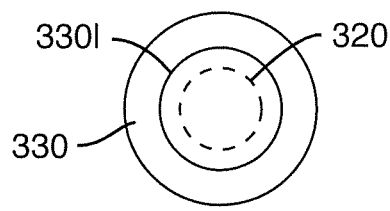
FIG. 3A and FIG. 3B area schematic end views of a crimping device and scaffold, in accordance with an embodiment of the present disclosure.
Figure 3B:
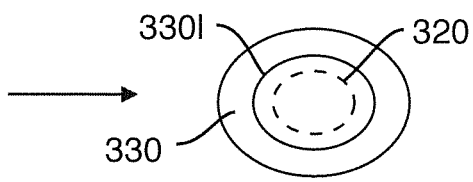

FIG. 3A illustrates an alternative embodiment, wherein the crimping device 330 comprises an inner lumen 330l at least partially surrounded by an air bladder that is configured to be inflated. Upon inflation of the air bladder as shown in FIG. 3B, the diameter of the inner lumen 330l decreases, thereby reducing an outer diameter of the radially self-expandable scaffold 320.

Figure 3C:
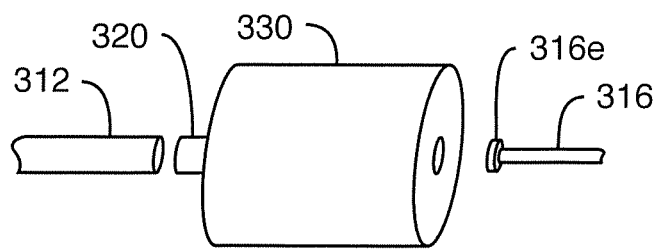
FIG. 3C is a schematic view of a system useful for crimping and loading a scaffold into a delivery sheath, in accordance with an embodiment of the present disclosure.

In some embodiments, a system like that shown in FIG. 3C is provided, which further comprises a push rod 316 having an end 316e, wherein the push rod end 316e has an outer diameter that is less than or equal to the reduced outer diameter or the scaffold 320, while also being greater than an inner diameter of the scaffold 320 (so as to be able to engage the scaffold 320 without engaging the crimping device 330 upon retraction). In use, the end 316e of the push rod 316 is positioned distal to the crimping device 330 and attached (not shown as attached) delivery sheath 312 and pushed proximally to engage a distal end of the reduced diameter scaffold 320. Upon continued pushing, the end 316e of the push rod 316 pushes the scaffold 320 proximally from the crimping device 330 and into the lumen of the delivery sheath 312. In other embodiments, rather than a push rod 316, the delivery catheter of FIG. 3C may be equipped with an inner member having a shaft with an enlarged distal end analogous to that shown in FIG. 2B.

Figure 4A:
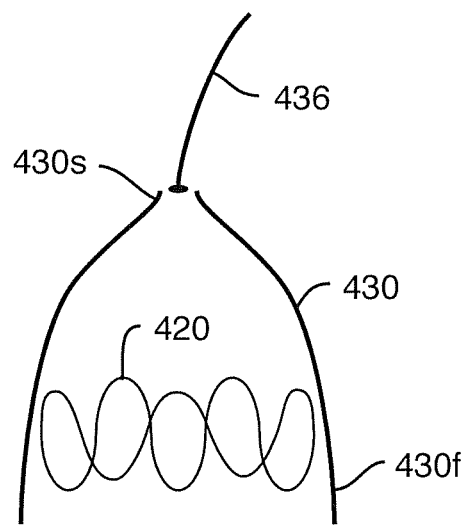
FIG. 4A is a schematic side view of a flexible tapered loading member and scaffold, in accordance with an embodiment of the present disclosure.
Figure 4B:
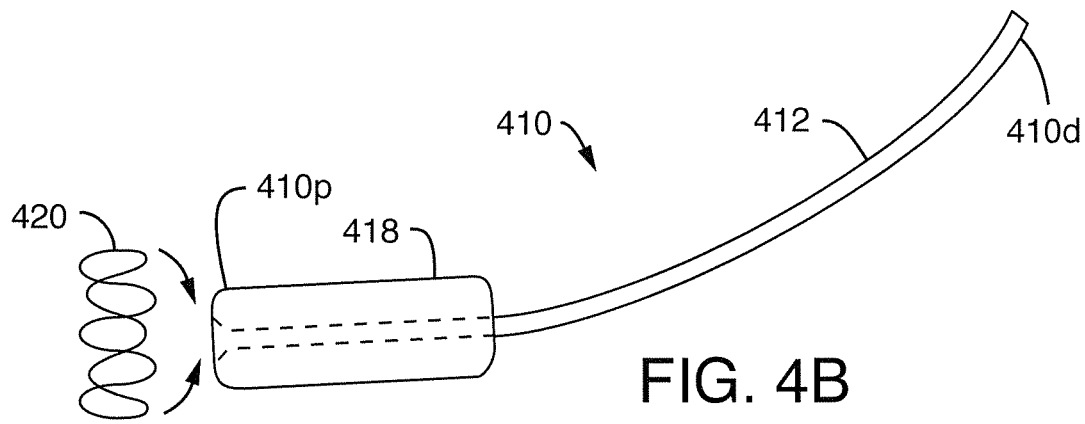
FIG. 4B is a schematic side view of a scaffold being loaded into a proximal handle of a delivery catheter, in accordance with an embodiment of the present disclosure.

In other embodiments, a scaffold may be crimped and loaded into a delivery device using a flexible tapered loading member. With reference to FIGS. 4A and 4B, a flexible tapered loading member 430 may be employed to load a scaffold 420 into a delivery catheter 410 comprising a handle 418 and a delivery sheath 412 having a delivery lumen with a defined delivery lumen diameter. The flexible tapered loading member 430 comprises a first end 430f, which is larger than the delivery lumen diameter and which is configured to receive a radially self-expandable scaffold 420, and a second end 430s, which is smaller than the delivery lumen diameter. When the second end of 430s of the flexible tapered loading member 430 is inserted into delivery lumen (either from the proximal end 410p or the distal end 410d of the delivery catheter 410) and the flexible tapered loading member 430 is advanced into the delivery lumen, the flexible tapered loading member 430 will collapse. As the flexible tapered loading member 430 collapses, a radially self-expandable scaffold 420 that is positioned within the flexible tapered loading member 430 will be compressed simultaneously and ultimately positioned within the delivery lumen. The lead-in taper of the loading member 430 facilitates compression of the loading member 430 (and scaffold 420).

In one embodiment, the flexible tapered loading member 430 is pulled into the delivery sheath 412 from a proximal end of the catheter 410 utilizing a flexible elongate component 436 (e.g., a filament such as a suture, string, thread or wire). Once the scaffold 420 is positioned in the handle 418, flexible tapered loading member 430 can be pulled out of the distal end 410d of the delivery catheter 410, leaving the scaffold 420 contained within the handle, to be delivered with an inner sheath or push rod (not shown) once the delivery sheath is placed into position for delivery within the sinus space. To maintain the position of the scaffold 420 during removal of the loading member 430, a tool may be employed either grasp the scaffold from the proximal end or act as a stop for the scaffold from the distal end.

In other embodiments the flexible tapered loading member 430 and scaffold 420 may be pushed into the proximal end 410p of the delivery catheter (rather than being pulled by an elongate flexible component). In still other embodiments the loading member 430 and scaffold 420 may be pushed or pulled into the distal end 410d of the delivery catheter 410. Once the scaffold 420 is positioned in the distal end 410d, the flexible tapered loading member 430 may be pulled out of the proximal end 410p of the delivery catheter 410, leaving the scaffold contained within the distal end 410d, to be delivered with an inner sheath or push rod.

In the embodiment shown the flexible tapered loading member 430 is funnel-shaped and may be formed from any suitable flexible material. In certain embodiments, the flexible tapered loading member 430 is in the form of an expandable and collapsible mesh (e.g., a braided mesh), which allows the flexible tapered loading member 430 to radially collapse without folding.

Figure 4C:
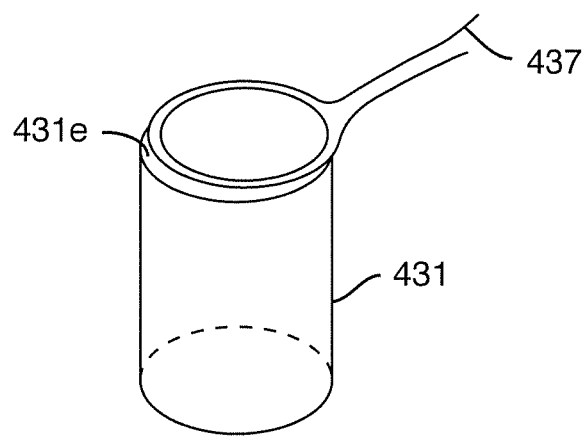
FIG. 4C is a schematic perspective view of a process of forming a flexible tapered loading member, in accordance with an embodiment of the present disclosure.

In another embodiment shown in FIG. 4C, the tapered receiving member 430 may be formed by cinching a filament 437 that is associated with one end 431e of a cylindrical member 431. In use, a scaffold 420 may be positioned in the cylindrical member 431, after which one or both ends of the filament 437 are pulled, closing the end 431e of the cylindrical member 431. At this point the now-formed and tapered receiving member 430 and scaffold 420 form an assembly which may be loaded into the delivery catheter as described above. In some embodiments, the filament 437 may be used to pull the assembly into the delivery catheter 410.

In other embodiments a detachable funnel is disposed at a distal end of a delivery catheter and a radially self-expandable scaffold is inserted (i.e., pushed or pulled) into the delivery catheter via the funnel.

Figure 5A:
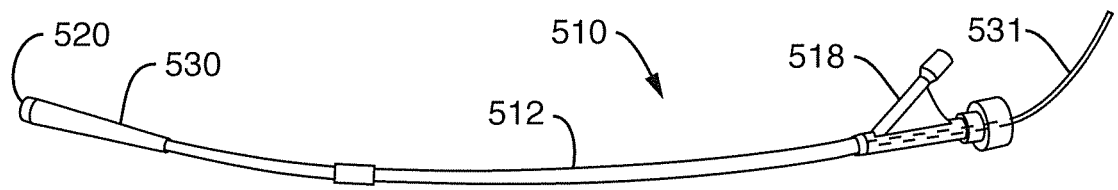
FIG. 5A is a side view of a delivery catheter in a process of being loaded with a scaffold, in accordance with an embodiment of the present disclosure.
Figure 5B:
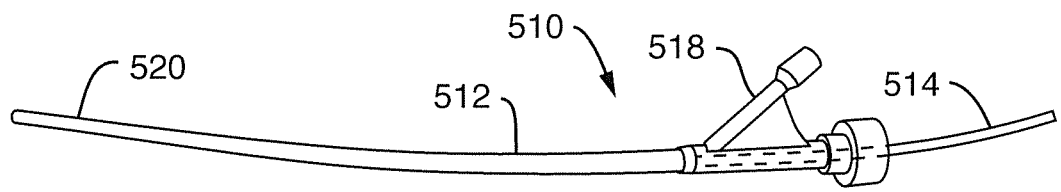
FIG. 5B and FIG. 5D are side views of delivery catheters that are with loaded scaffolds, in accordance with embodiments of the present disclosure.
Figure 5C:
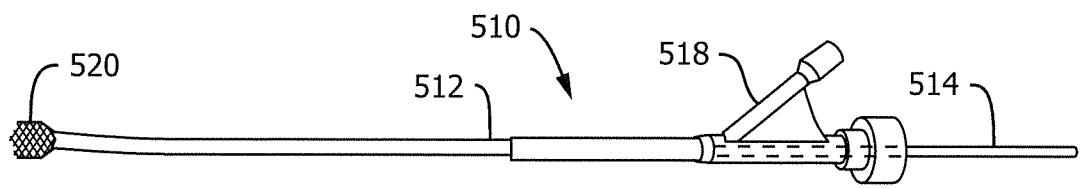
FIG. 5C is a side view of a delivery catheter and a partially deployed scaffold, in accordance with an embodiment of the present disclosure.

In one embodiment illustrated in FIGS. 5A-5C, a delivery system may include a detachable loading funnel 530 and a delivery catheter 510 comprising a handle (in particular, a hub 518), delivery sheath 512 and a pusher member 514. During loading, the loading funnel 530 is attached to the distal tip of the delivery sheath 512. One or more filaments 531. (e.g., strings, threads, sutures, wires, etc.) may be attached to a proximal end of the scaffold 520, and strung through the funnel 530 and out the proximal end of the delivery catheter 510. The scaffold 520 is drawn into the loading funnel 530 and ultimately transferred into the delivery sheath 512 by pulling on the filament(s) 531. Subsequently, the loading funnel 530 is removed from the distal tip of the delivery sheath 512, and the filament(s) 531 are removed from the scaffold 520 and delivery catheter 510. In one embodiment, a filament 531 in the form of a loop that is strung through the scaffold 520 may be employed whereby the loop is pulled to draw the scaffold 520 into the funnel 530, after which the loop is severed where it emerges from the proximal end of the delivery catheter 510, thereby forming two ends, one of which is pulled to remove the filament 531.

As illustrated in FIG. 5B, a pusher member 514 is then inserted through the proximal end of the delivery catheter 510, and advanced to the proximal end of the crimped scaffold 520. The pusher member 514 may be formed, for example, of a single material or, alternatively, may be formed of multiple materials to vary flexibility along its length.

The delivery system may also have an inner support member inserted through the pusher member, running through the length of the system. The support member may be formed, for example, of a single material or, alternatively, may be formed of multiple materials to vary flexibility along its length. The support member may also have a lumen to accommodate a guide wire or illumination system. The support member may go through the center of the scaffold and the scaffold may be crimped over the support member.

Figure 6A:
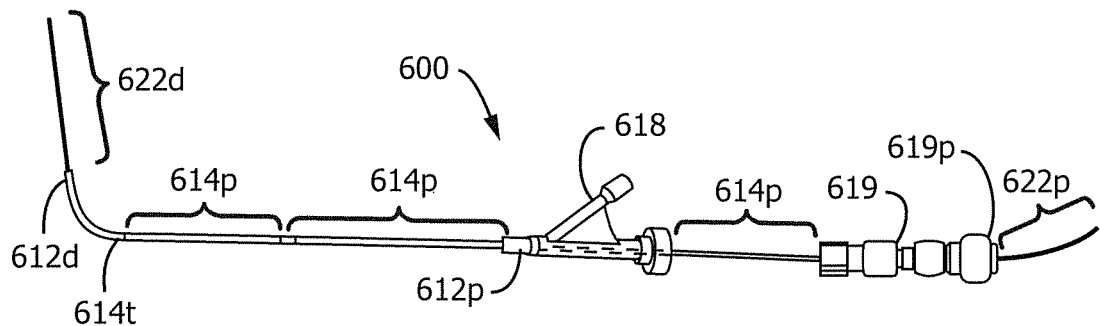
FIG. 6A is an illustration of a delivery system in accordance with an embodiment of the present disclosure.
Figure 6B:
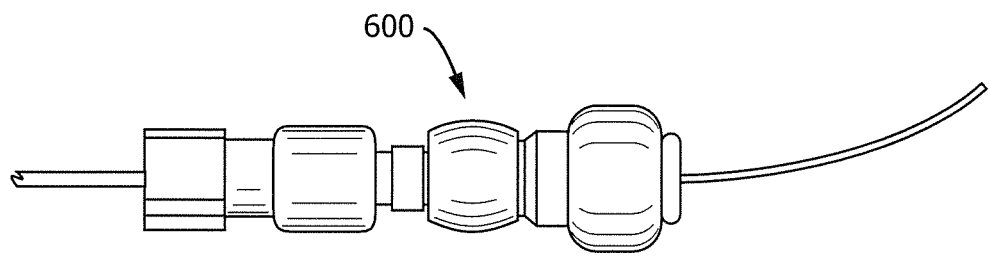
FIG. 6B and FIG. 6C correspond to enlarged views of FIG. 6A.
Figure 6C:
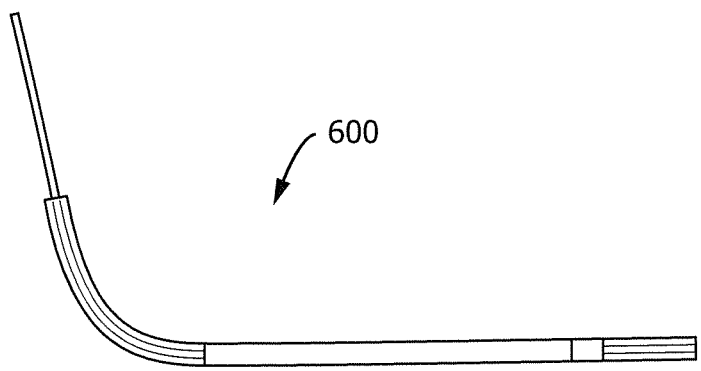

A specific embodiment of such a system 600 is illustrated in FIG. 6A wherein a delivery catheter comprising clear outer sheath having a distal end 612d and a proximal end 612p terminating at a handle/hub 618. Inserted into the delivery catheter is a pusher member having a handle assembly 619 and an elongate member having a proximal metallic portion 614p extending from the handle assembly 619, through the delivery catheter handle/hub 618 and into the outer sheath, at which point the elongate member transitions to a polymeric distal portion 614d, finally terminating at point 614t. Finally, the system includes a polymeric support member extending through the entire system, which includes a clear proximal portion 622p with a first durometer extending from a proximal end 619p of the pusher member handle 619 transitioning within the system to a pigmented distal portion 622d with a second durometer extending from a distal end of the outer sheath 612d. Enlarged views of the device of FIG. 6A are shown in FIGS. 6B and 6C.

The loaded delivery system may be tracked into the intended sinus space, for example, either directly or over a guide wire (in which case the pusher member 514 may be provided with a lumen to accommodate the guide wire) or through an external guide member or catheter. Deployment may be accomplished by holding the pusher member 514 stationary and pulling back on the delivery sheath 512, to unsheathe the scaffold 520 (shown partially unsheathed in FIG. 5C). Delivery may also be accomplished by pushing the pusher member or by a combination of pushing to initiate deployment, followed by pulling to maintain positional accuracy.

Figure 5D:
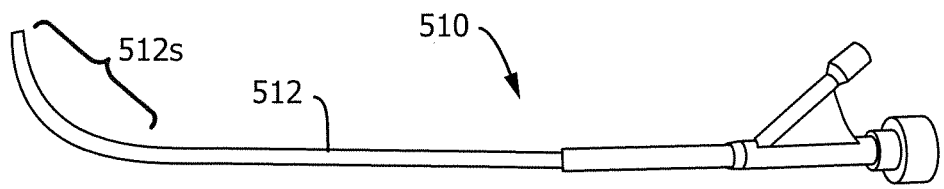
Figure 7:
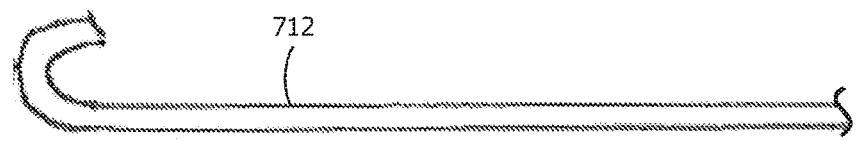
FIG. 7 is a schematic side view of a distal end of a delivery sheath, in accordance with an embodiment of the present disclosure.

While the delivery sheath 512 shown in FIGS. 5A-5C is linear, in other embodiments, the delivery sheath 512 may be provided with a curvature. For example, the delivery sheath 512 may have a pre-formed shape-memorized section 512s with a curvature that improves access to various ostia as shown in FIG. 5D. Such a configuration, wherein the angle of curvature of the delivery sheath 512 ranges from about 0° to about 45° may be useful, for example, to achieve sphenoid sinus access. In other configurations, the curvature of the delivery sheath 512 may range, for example, from about 45° to about 110° and may be useful to achieve frontal sinus access, for example. In other configurations, for example, such as that illustrated in FIG. 7, the curvature of the delivery sheath 712 may range from about 110° to about 170°. In such embodiments, the delivery sheath may provide may be useful, for example, to achieve maxillary sinus access.

Figure 8A:
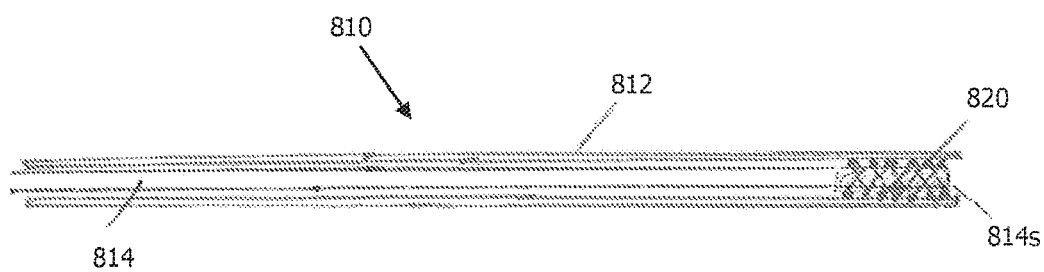
FIG. 8A is a schematic partial cross-sectional side view of a distal end of a delivery system, in accordance with an embodiment of the present disclosure.
Figure 8B:
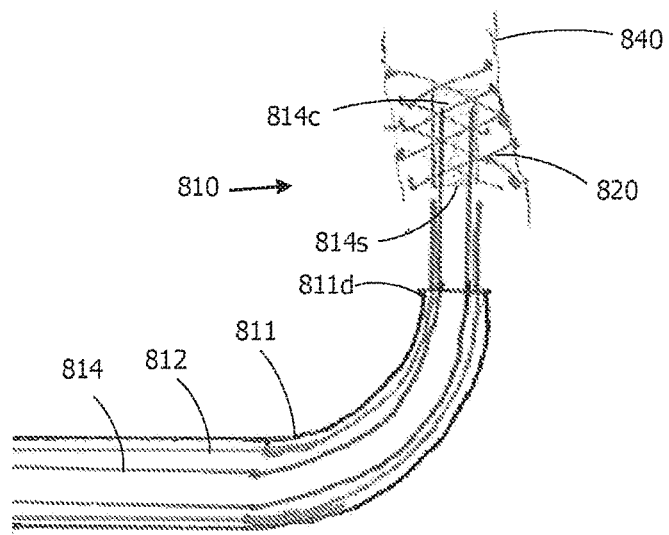
FIG. 8B is a schematic partial cross-sectional side view illustrating deployment of a scaffold using the system of FIG. 8A, in accordance with an embodiment of the present disclosure.

While the delivery systems described immediately above are based on the use of a pusher to deliver a scaffold from a delivery sheath, in other non-pusher embodiments, the scaffold may be retained by compressive friction created by compressing the scaffold onto an inner member. For example, turning now to FIG. 8A, a distal end of a delivery system 810 is shown that includes a scaffold 820, an outer sheath 812, and an elongate inner member 814 having an inner support segment 814s. The scaffold is compressed onto the inner support segment 814s by the outer sheath 812. Such a delivery catheter may be used independently or in conjunction with a guide catheter 811 as shown in FIG. 8B, through which the delivery catheter has been advanced to a target site in a sinus 840. The scaffold 820 has a higher force of friction when in contact with the material provided on the inner support segment 814s than it does when in contact with the material provided on the outer sheath 812, allowing the support segment 814s to pull the scaffold 820 along with the support segment 814s as the support segment 814s moves in either a proximal or a distal direction relative to the outer sheath 812, including allowing the inner support segment 814s to pull the scaffold out of the distal end of the outer sheath 812. Examples of materials for the outer surface of the inner support segment 814s include biocompatible polymers including but not limited to polyethylene, polyethylene terephthalate, ultra-high molecular weight polyethylene, polytetrafloroethylene, expanded polytetrafloroethylene, polypropylene, silicone rubber, polycarbonate urethane, polyurethane, polyamide, polyether block amide, polyoxymethylene, polyetheretherketone, and aliphatic or semi-aromatic polyamide. Examples of materials for the inner surface of the outer sheath 812 include, but are not limited to, biocompatible polymers including but not limited to polyethylene, polyethylene terephthalate, ultra-high molecular weight polyethylene, polytetrafloroethylene, expanded polytetrafloroethylene, polypropylene, silicone rubber, polycarbonate urethane, polyurethane, polyamide, polyether block amide, polyoxymethylene, polyetheretherketone, and aliphatic or semi-aromatic polyamide. Both the inner support segment 814s and the outer sheath 812 may be of a composite of materials, allowing for a variable stiffness and frictional properties at various points in their lengths. At the time of delivery, a distal end of the delivery system 810 is advanced through the guide catheter 811 and out of its distal end 811d. At the target position, due to the friction between the elongate inner member 814 and scaffold 820 that has been established by compression of the scaffold 820 onto the inner support segment 814s, the elongate inner member 814 and scaffold 820 are advanced relative to the outer sheath 812 (e.g., by advancing the elongate inner member 814 while maintaining the position of the outer sheath 812 and/or by retracting the outer sheath 812 while maintaining the position of the elongate inner member 814) to an extent such that the outer sheath 812 no longer confines the scaffold allowing the scaffold 820 to expand into contact with tissue 840 as shown. In other embodiments, movement of the scaffold 820 may be coordinated with movement of the elongate inner member 814, for example, by providing one or more retention features on the inner support segment 814s, allowing the support segment 814s to pull the scaffold 820 along with the support segment 814s as the support segment 814s moves in either a proximal or a distal direction relative to the outer sheath 812. Such retention features may include, for example, steps, bumps, hooks, barbs, or rings that engage at least a portion of the scaffold 820, among other possibilities.

Figure 9:
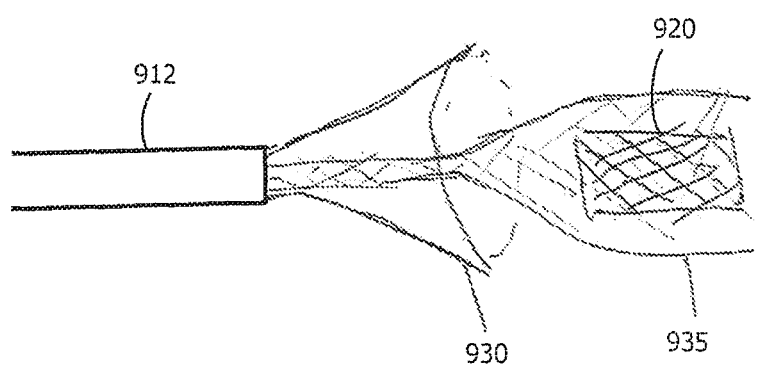
FIG. 9 is a schematic side view of a delivery sheath in a process of being loaded with a scaffold, in accordance with an embodiment of the present disclosure.

In another variation, and with reference to FIG. 9 the scaffold 920 may be inserted into a collapsible braided mesh 935, and the braided mesh 935 pulled into the loading funnel 930, resulting in the compression of the scaffold 920 that is pulled into the loading funnel 930 along with the mesh 935. One or more flexible elongate elements, for example, one or more filaments (e.g., threads, sutures, strings, wires, etc.), may be attached to the braided mesh 935 for this purpose.

Figure 10:
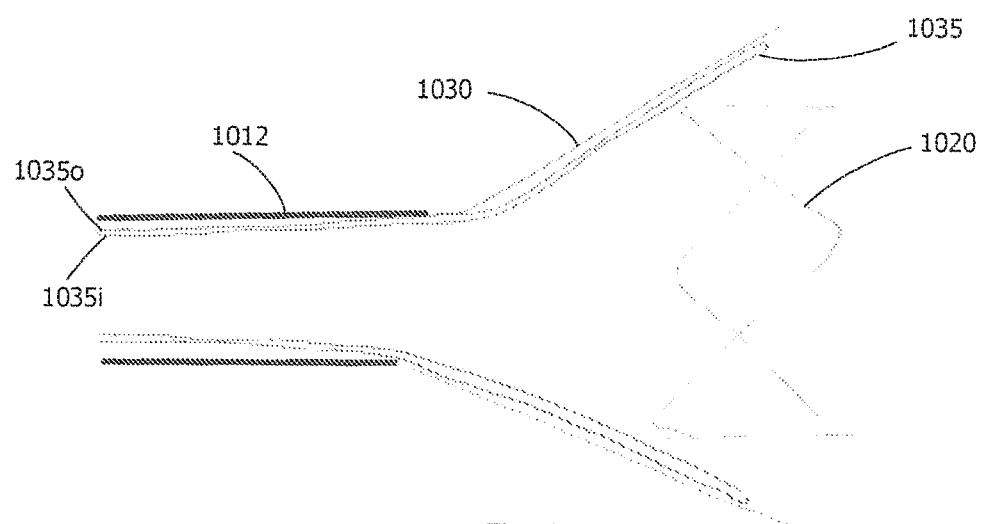
FIG. 10 is a schematic partial cross-sectional side view of a delivery sheath in a process of being loaded with a scaffold, in accordance with an embodiment of the present disclosure.

In still another variation, and with reference to FIG. 10 the scaffold 1020 may be inserted into a double-layer mesh 1035 having an inner layer 1035i and an outer layer 1035o. By simultaneously pulling the inner layer 1035i and an outer layer 1035o, the double-layer mesh 1035 can be pulled into a loading funnel 1030, compressing the scaffold 1020 that is pulled into the loading funnel 1030 along with the double-layer mesh 1035. Once the scaffold is properly positioned in the lumen of a delivery sheath 1012, one can continue to pull either the outer layer 1035o alone, with the result being that the mesh 1035 is pulled off the scaffold 1020 and ultimately removed from the delivery sheath 1012. Subsequently, a pusher member may be inserted into delivery sheath 1012 to complete delivery of the scaffold 1020, among other methods.

Figure 11A:
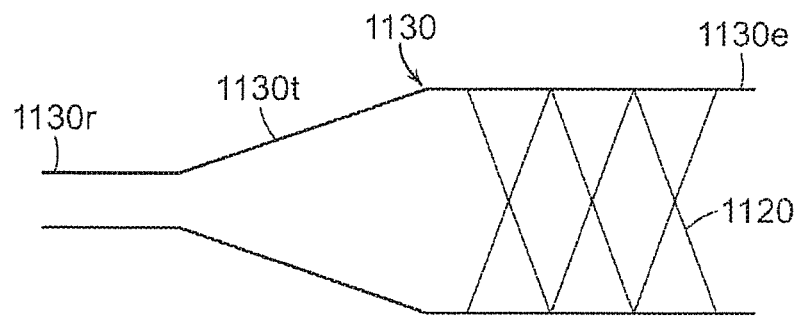
FIG. 11A is a schematic partial cross-sectional side view of a scaffold within a loading funnel, in accordance with an embodiment of the present disclosure.
Figures 11B, 11C:
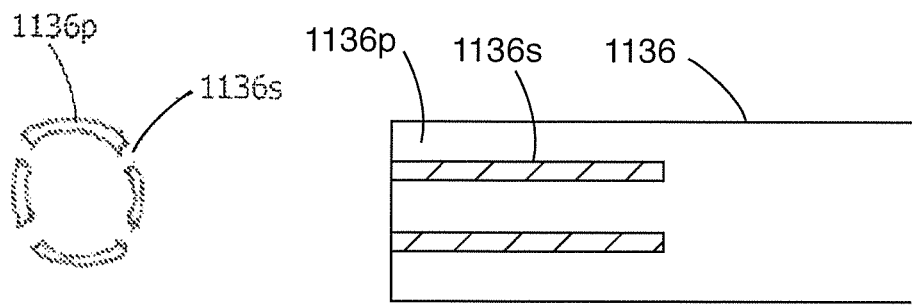
FIGS. 11B and 11C are schematic side and end views, respectively, of a collapsible loading member, in accordance with an embodiment of the present disclosure.
Figures 11D, 11E:
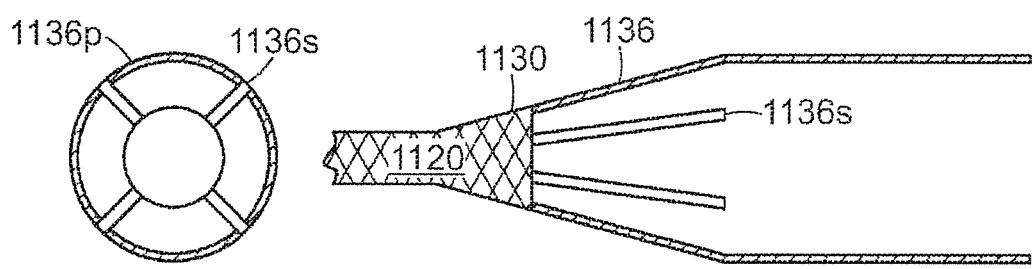
FIG. 11D is a schematic partial cross-sectional side view of scaffold partially compressed by a loading system in accordance with an embodiment of the present disclosure.
FIG. 11E is a schematic end view of the collapsible loading member shown in FIG. 11D.

In still another variation and with reference to FIGS. 11A-11E, the scaffold 1120 may be initially inserted into a loading funnel 1130 having an enlarged diameter end 1130e and a reduced diameter end 1130r as shown in FIG. 11A. The enlarged diameter end 1130e of the loading funnel 1130 may, for example, approximately match the uncompressed diameter of the scaffold 1120. The reduced diameter end 1130r of the loading funnel 1130 may be configured to interface with a distal end of a delivery device (not shown), for example, by attachment to a distal end of a delivery device adjacent to a delivery lumen or by insertion into a delivery lumen at a distal end of a delivery device. During loading, the scaffold 1120 is advanced along the tapered portion 1130t between the enlarged diameter end 1130e of the loading funnel 1130 and the reduced diameter end 1130r of the loading funnel 1130, thereby compressing the scaffold 1120 to a diameter suitable for introduction into a lumen of the delivery device. In the embodiment shown, a pusher member 1136 having slots 1136s forming protrusions 1136p is used to push the scaffold 1120 from the enlarged diameter end 1130e to the reduced diameter end 1130r of the loading funnel 1130. As the pusher member 1136 is advanced through the tapered portion 1130t of the loading funnel 1130, contact with the walls of the loading funnel 1130 move the protrusions 1130f of the loading funnel inward (thus reducing the width of the slots), thereby allowing the pusher member 1136 to continue to advance into the tapered portion of the funnel 1130 and thus continue to push the scaffold 1120 through the funnel 1130 and into the delivery device.

In certain embodiments, the slots 1136s may be tapered, for example, being larger at the tip of the member 1136, and decreasing in width as one moves along the length of the device.

In certain embodiments, rather than having slots that extend longitudinally along the member 1136 (i.e., parallel to the axis of the member 1136), the slot(s) may include one or more spiral cuts of varying thickness in order to allow for the diametric compression at the tip of the member 1136.

Figure 30A:
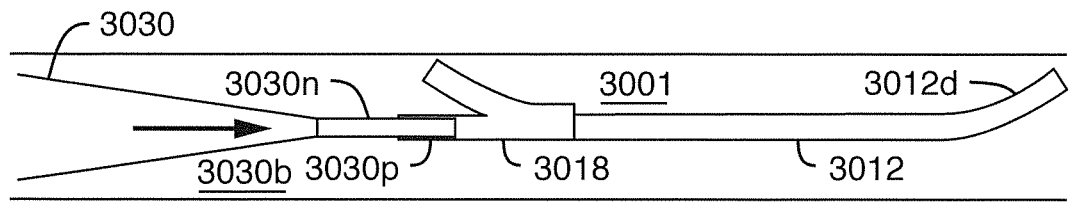
FIG. 30A is a schematic side view of a first assembly and FIG. 30B is a schematic side view of a loading assembly, which when combined form a scaffold delivery system, in accordance with an embodiment of the present disclosure.
Figure 30B:
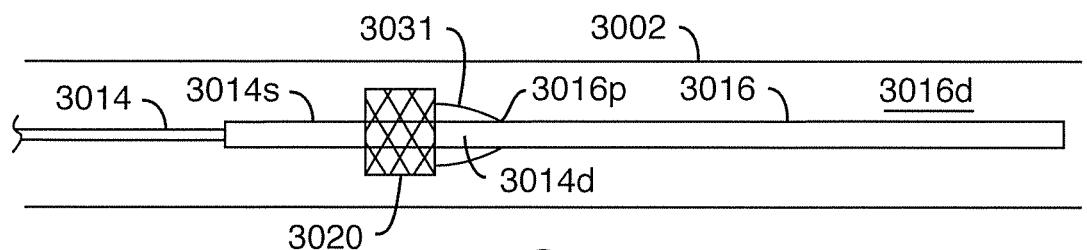

In another embodiment illustrated in FIGS. 30A and 30B, a delivery system is shown which includes a first assembly 3001 and a second assembly 3002. The first assembly 3001, shown in FIG. 30A, comprises a detachable loading funnel 3030 having a funnel neck 3030n, and a delivery catheter comprising a handle 3018 (in particular, a Y-connector hub 3018) and a delivery sheath 3012. The loading funnel 3030 is inserted into the handle 3018, in particular, into one of the legs of the Y-connector hub, such that a portion 3030p of the loading funnel 3030 is positioned in the Y-connector hub 3018. The loading funnel 3030 is detachable from the handle 3018 by means of a readily breakable connection point 3030b the funnel neck 3030n in the embodiment shown, although the loading funnel 3030 may be detached from the handle 3018 any other suitable mechanism that allows coupled components to be decoupled (e.g., male and female threaded portions, etc.).

The second assembly 3002, shown in FIG. 30B, comprising an elongate inner member 3014 having a distal end 3014d and a proximal end (not shown) and comprising an inner support segment 3014s, an elongate pulling member 3016 having a distal end 3106d and a proximal end 3016p, and a scaffold 3020 that is secured to the pulling member 3016 by one or more connecting members, for example, one more filaments 3031 (e.g., sutures, strings, threads, wires, etc.). For example, a filament 3031 in the form of a loop that is strung through the scaffold 3020 may be employed to secure the scaffold 3020 to the pulling member 3016, whereby each of the ends (i.e., first and second ends) of the filament 3031 is secured to the pulling member 3016. When it is desired to disengage the scaffold 3020 from the pulling member 3016, a first end of the filament 3031 may be severed from the pulling member 3016, and the filament 3031 may be removed from the scaffold 3020 by pulling the second end of the filament 3031 (e.g., by pulling the filament 3031 or by pulling the pulling member 3016 to which the second end of the filament 3031 is attached). Where desired, the proximal end 3016p of the elongate pulling member 3016 may be detachably secured to the distal end 3014d of the elongate inner member 3014, for instance, any suitable mechanism that allows coupled components to be decoupled (e.g., by a readily breakable connection, for instance, one more filaments that may be severed, by male and female threaded portions, etc.). For example, analogous to the scheme described above in conjunction with the scaffold 3020, in one embodiment, a filament 3031 in the form of a loop that is strung through the elongate inner member 3014 (e.g., a aperture in the distal end 3014 of the elongate inner member 3014) may be employed to secure the elongate inner member 3014 to the pulling member 3016, whereby each of the ends of the filament 3031 is secured to the pulling member 3016.

During loading, wherein the second assembly 3002 of FIG. 30B is pushed and/or pulled through the first assembly 3001 of FIG. 30, the second assembly 3002 may be inserted into the first assembly 3001, for example, by first inserting the pulling member 3016 of the second assembly 3002 into the funnel 3030 of the first assembly 3001. Where the pulling member 3016 is of sufficient length, the second assembly 3002 may be advanced through the first assembly 3001 exclusively by manipulation of the pulling tube 3016, first from the funnel end of the first assembly 3001 until the distal end 3016d or the pulling member 3016 emerges from a distal end 3012d of the outer delivery sheath 3012, at which point the pulling member 3016 can be used to pull the second assembly 3002 until the scaffold 3020 is positioned at a desired position in the delivery sheath 3012. In other embodiments, the second assembly 3002 may be advanced at least a portion of the way through the first assembly 3001 by pushing the inner member 3014. In any case, advancement of the second assembly 3002 into the first assembly 3001, and more specifically, advancement of the scaffold 3020 and inner support segment 3014s through the funnel 3030 causes the scaffold 3020 to be compressed to diameter suitable for advancement though the second assembly 3002. The scaffold 3020 may also be compressed onto the inner support segment 3014s, in which case the scaffold 3020 may have a higher force of friction when in contact with material provided on an outer surface of the inner support segment 3014s than it does when in contact with the material provided on an inner surface of the outer delivery sheath 3012, allowing the support segment 3014s to pull the scaffold 3020 along with the support segment 3014s as the support segment 3014s is moved in either a proximal or a distal direction relative to the outer delivery sheath 3012, such that advancement and retraction of the inner support segment 3014s causes advancement and retraction, respectively, of the scaffold 3020. In some embodiments, movement of the scaffold 3020 may be coordinated with movement of the elongate inner member 3014, for example, by providing one or more retention features on an inner support segment 3014s, allowing the support segment 3014s to pull the scaffold 3020 along with the support segment 3014s as the support segment 3014s is moved in either a proximal or a distal direction relative to the outer delivery sheath 3012. Such retention features may include, for example, steps, bumps, hooks, barbs, or rings that engage at least a portion of the scaffold 3020, among other possibilities.

Once the scaffold 3020 is advanced to a desired position in the outer delivery sheath 3012 (e.g., proximal the distal end 3012d of the outer delivery sheath 3012), the one more filaments 3031 may be removed from the scaffold 3020 to free the scaffold 3020 from the pulling member 3016. For example, where the filament 3031 is in the form of a loop that is strung through the scaffold 3020 as described above, a first end of the filament 3031 may be severed from the pulling member 3016, after which distal movement of the second end of the filament 3031 (e.g., brought about by pulling the filament 3031 itself or the pulling member 3016 to which the second end of the filament 3031 is attached), causes the first end of the filament 3031 to be pulled through the scaffold 3020 and out of the distal end 3012d of the outer delivery sheath 3012. If attached, the pulling member 3016 may be detached from the inner member 3014 as well. In the embodiment illustrated, the loading funnel 3030 may be removed from the handle 3018 by snapping the readily breakable region 3030b of the funnel neck 3030n, among other suitable methods.

In certain embodiments, where an inner member has sufficient column strength, the inner member and any associated components of a second assembly (e.g., scaffold, inner support segment, etc.) may be advanced at least a portion of the way through a lumen of a first assembly (which may include, for example, a funnel, handle, outer delivery sheath, etc.) by pushing a proximal end the inner member. In these embodiments, advancement of the inner member may be facilitated by providing a press member at a proximal end of the inner member.

Figure 31:
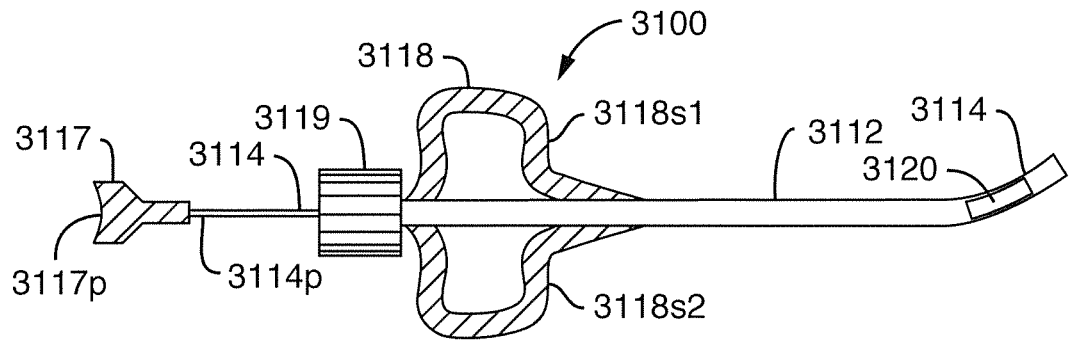
FIG. 31 is a schematic side view of a scaffold delivery system, in accordance with an embodiment of the present disclosure.

For example, in one system 3100 illustrated in FIG. 31, a second assembly is provided that includes an inner member 3114, a press member 3117 provided at a proximal end 3114p of the inner member 3114, and a scaffold 3120 provided around a support segment (not separately numbered) positioned at a distal end 3114d of the inner member 3114. The system 3100 also includes a first assembly that includes an ergonomic handle 3118, an outer delivery sheath 3112 attached to and/or integrated with the handle 3118, and an adaptor 3119 (e.g., check valve or a valve that can be opened and closed, for instance, Touhy Borst valve, etc.) attached to and/or integrated with an ergonomic handle 3118. As illustrated, the inner member 3114 extends through the valve 3119, handle 3118, and through a majority of the length of the outer delivery sheath 3112. At a subsequent point, the scaffold 3120 may be delivered from the outer delivery sheath 3112 by distally advancing the second assembly relative to the first assembly, for example, by applying pressure to a proximal surface 3117p of the press member 3117 such that the second assembly moves distally relative to the first assembly. For example, as previously noted, one or more retention features may be provided on the support segment, or the scaffold 3120 may have a higher force of friction when in contact with the material provided on the support segment of the inner member 3114 than it does when in contact with the material provided on the inner surface of the outer delivery sheath 3112, allowing the support segment to pull the scaffold 3120 along with the support segment as the support segment moves in either a proximal or a distal direction relative to the delivery sheath 3112. For instance, a proximal surface 3117p of the press member 3117 may be pressed with an operator's thumb while distal surfaces 3118s1 and 3118s2 are engaged by the operator's index and middle fingers (e.g., much like the plunger of a syringe is pressed by the thumb while the flange on the syringe barrel is held with the index and middle fingers) in order to apply pressure at a proximal end 3114p of the inner member 3114. Since the second assembly can be advanced relative to the first assembly by applying pressure at a proximal end 3114p of the inner member 3114, it is possible to load and advance the scaffold 3120 in the outer sheath 3112 without a pulling member, although in other embodiments, a pulling member 3117 may be employed to assist scaffold 3120 loading.

Figure 31A:
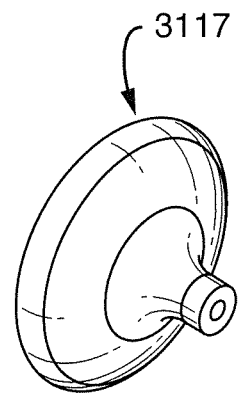
FIGS. 31A-31C are schematic perspective views of three press members, in accordance with embodiments of the present disclosure.
Figure 31B:
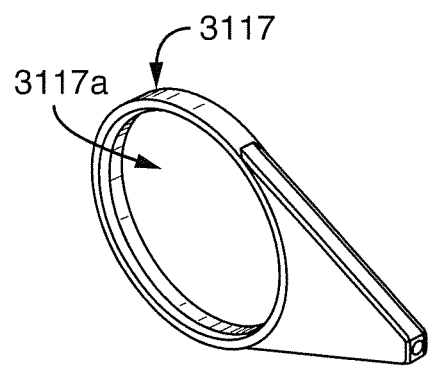
Figure 31C:
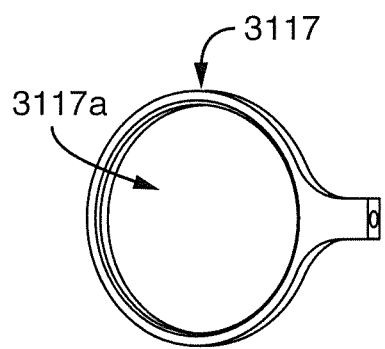

An embodiment of a press member 3117 that is similar to that of FIG. 31 is shown in FIG. 31A. Additional press members 3117 shown in FIGS. 31B and 31C may be engaged by placing an operator's thumb through an aperture 3117a (e.g., a loop) that is provided in the press member 3117.

Figure 32:
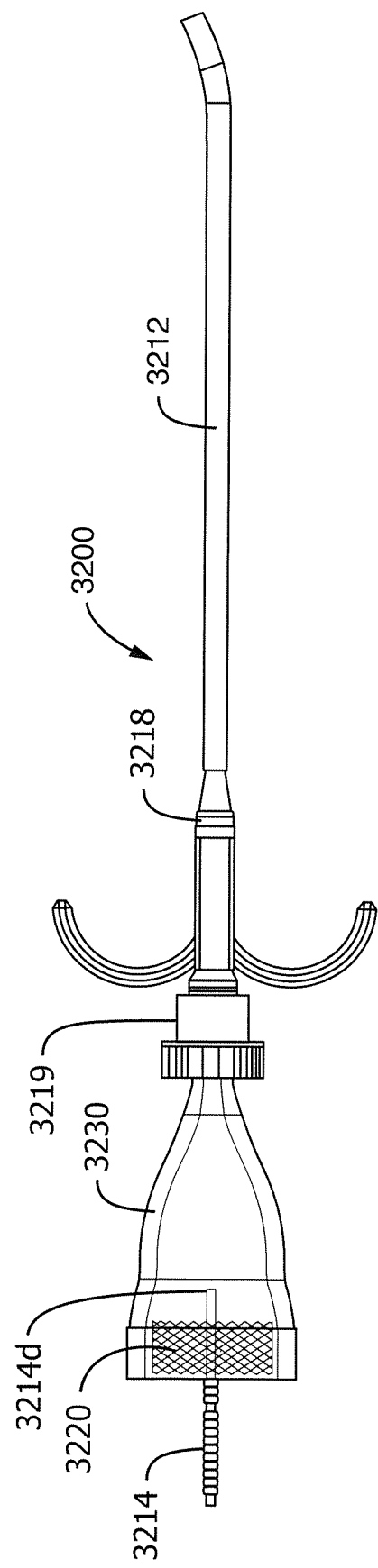
FIG. 32 is a schematic side view of a scaffold loading and delivery system, in accordance with an embodiment of the present disclosure.
Figure 32B:
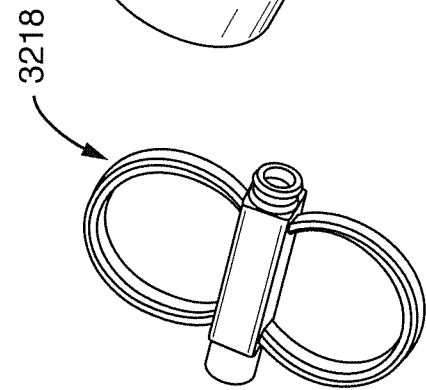
FIG. 32B is a schematic perspective view of an ergonomic handle, in accordance with an embodiment of the present disclosure.
Figure 32A:
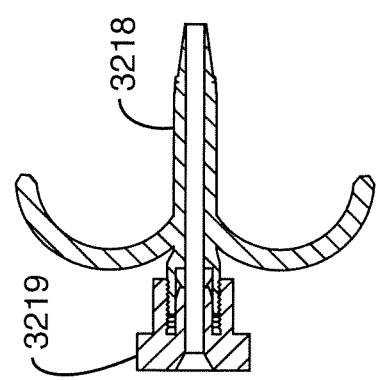
FIG. 32A is a schematic cross-sectional view of the ergonomic handle and valve of shown in FIG. 32.

In an embodiment of a system 3200 illustrated in FIG. 32, a distal end of a second assembly is shown, which includes an inner member 3214 and a scaffold 3220 provided around a support segment (not shown) near a distal end 3214d of the inner member 3214. The scaffold 3220 may be attached to the inner member, for example, one or more filaments (not shown). For example, a plurality of filaments may be looped through an aperture in the scaffold wall (e.g., a diamond-shaped aperture of a braided scaffold) and an aperture that is drilled or formed in a distal tip 3214d of the inner member 3214. The system 3200 also includes a first assembly that includes a funnel 3230, an ergonomic handle 3218, an outer delivery sheath 3212 and an adaptor 3219 (e.g., a Touhy Borst valve with thumb screw closure). The scaffold 3220 may subsequently be pulled by the one or more filaments through the funnel 3220, valve 3219 and handle 3218 and through a majority of the length of the outer delivery sheath 3212, until the distal end 3214d of the inner member 3214 emerges from a distal end of the outer delivery sheath 3212, allowing each of the filament loops to be cut and removed from the scaffold 3220 and inner member 3214. As previously indicated, one or more retention features may be provided on the support segment, or the scaffold 3220 may have a higher force of friction when in contact with the material provided on the support segment of the inner member 3214 than it does when in contact with the material provided on the inner surface of the outer delivery sheath 3212, allowing the support segment to pull the scaffold 3220 along with the support segment as the support segment moves in either a proximal or a distal direction relative to the delivery sheath 3212. In certain embodiments, a portion of the inner member 3214 that is located distal to the scaffold 3220 may be detachably secured to a remainder the elongate inner member 3014, for example, by any suitable mechanism that allows coupled components to be decoupled (e.g., providing a readily breakable linkage between the coupled components, male and female threaded portions, etc.). In some embodiments, the second assembly may be distally advanced relative to the first assembly by applying pressure to a proximal surface of a press member (not shown) as described above. A cross-sectional view of the ergonomic handle 3218 and valve 3219 is shown in FIG. 32A. An alternative design for an ergonomic handle 3218 is shown in FIG. 32B.

Figure 33B:
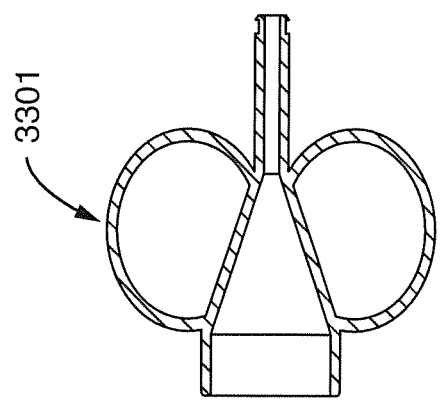
FIG. 33B is a schematic cross-sectional view of the combined funnel and handle shown in FIG. 33A.
Figure 33A:
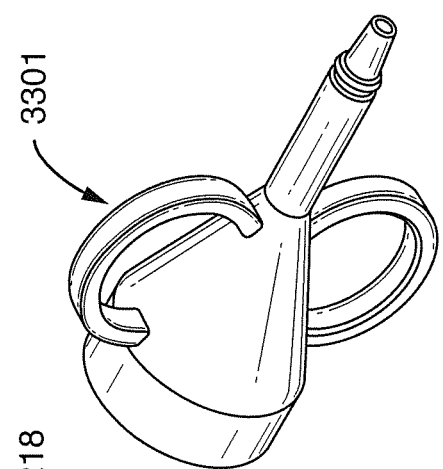
FIG. 33A is a schematic perspective view of a combined funnel and handle, in accordance with an embodiment of the present disclosure.
Figure 34B:
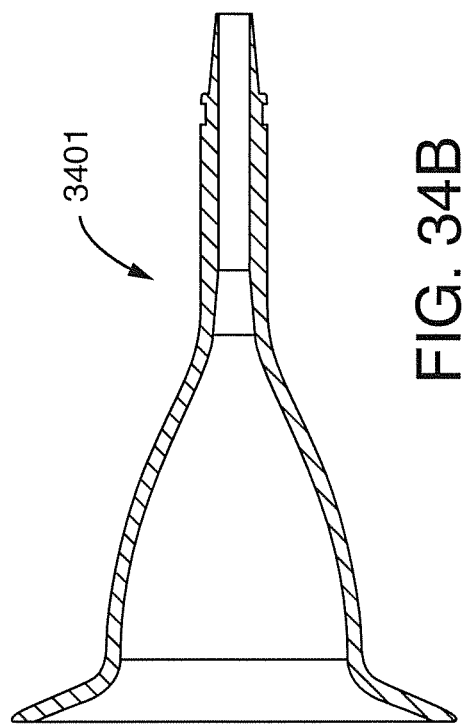
FIG. 34B is a schematic cross-sectional view of the combined funnel and handle shown in FIG. 34A.
Figure 34A:
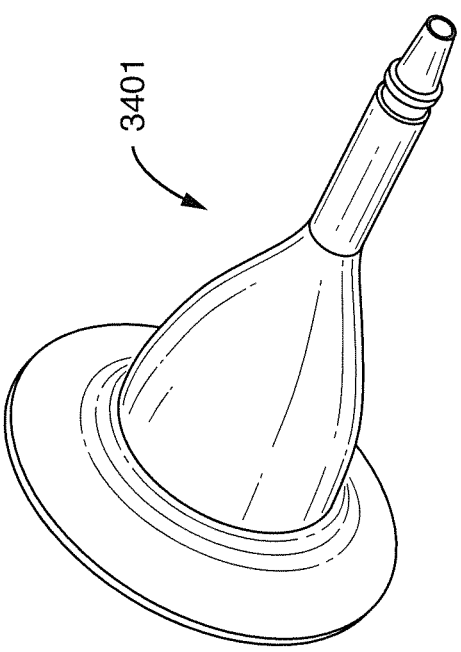
FIG. 34A is a schematic perspective view of a combined funnel and handle, in accordance with an embodiment of the present disclosure.

In certain embodiments, funnel and handle may be combined into a single integrated component. One example of such an integrated component 3301 is shown in perspective view in FIG. 33A and cross-sectional view in FIG. 33B. Another example of such an integrated component 3401 is shown in perspective view in FIG. 34A and cross-sectional view in FIG. 34B.

Figure 38:
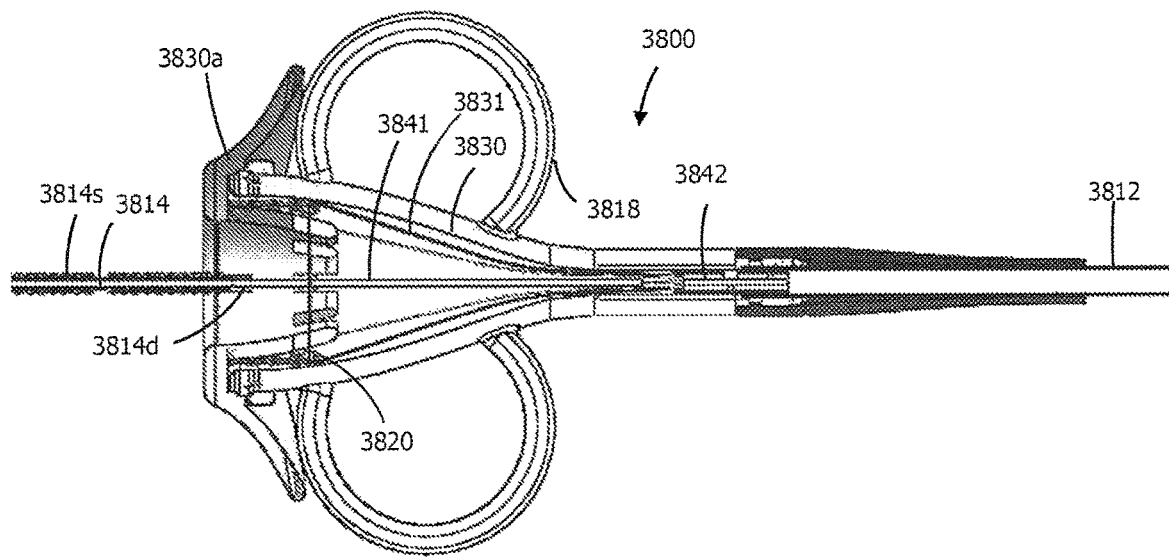
FIG. 38 is a schematic partial cross-sectional view of a scaffold loading and delivery system, in accordance with an embodiment of the present disclosure.

In an embodiment of a system 3800 illustrated in FIG. 38, a proximal end of a first assembly is shown, which includes a funnel 3830 and an ergonomic handle 3818 (which are integrated into a combined funnel and handle, analogous to those previously described, e.g., in FIGS. 33A, 33B, 34A and 34B), as well as an outer delivery sheath 3812 extending from a distal end of the same. Provided at the proximal end of the funnel 3830 is a funnel cap 3830a, which acts to ensure that scaffold 3820 is secured in place during shipping and storage, so scaffold 3820 is properly positioned within the system 3800 when it is desired to load scaffold 3820.

Also shown is a distal end of a second assembly, which includes a hollow inner member 3814 having support segment 3814s near a distal end 3814d of the inner member 3814. A stylet 3841 extends from a proximal end (not shown) of the hollow inner member 3414, through the hollow inner member 3414, out of the distal end 3414d of the hollow inner member 3414, and into a capsule 3842, which is described in more detail below. A scaffold 3820 is linked to the capsule 3842 via one or more filaments 3831 (one numbered). For example, one end of each of one or more filaments 3831 may be attached to the capsule 3842, and the other end of each of one or more filaments 3831 may be looped from the capsule 3842, through the scaffold 3820, back to the capsule 3842, and attached to the capsule.

By advancing the second assembly relative to the first assembly, and more particularly, by advancing the inner member 3814, stylet 3841 and capsule 3842 relative to the first assembly, the scaffold 3820 may be pulled via the capsule 3842 and one or more filaments 3831 through the funnel 3820 and handle 3818 and through a majority of the length of the outer delivery sheath 3812, until the capsule 3842 passes through the distal end of the outer delivery sheath 3812. At this point, one end of each of the one or more filaments 3831 may be freed from the capsule and the other end of each of the one or more filaments 3831 may be pulled away from the distal end of the outer delivery sheath 3812, allowing each of the one or more filaments 3831 to be removed from the scaffold 3820 and outer delivery sheath 3812.

Figure 39A:
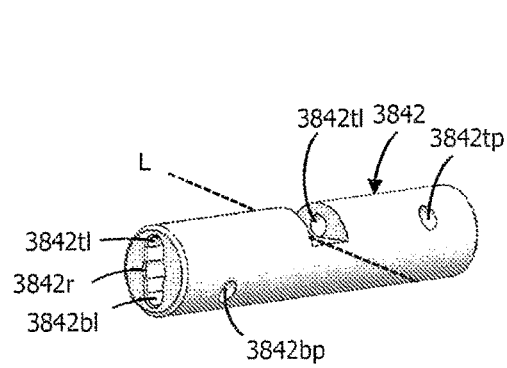
FIG. 39A is a schematic perspective view of a loading capsule, in accordance with an embodiment of the present disclosure.

Capsule 3842 is shown in more detail in FIG. 39A and includes a top filament lumen 3842tl that connects with a top glue port 3842tp, a bottom filament lumen 3842bl that connects with a bottom glue port 3842bp, and a stylet receptacle 3842r, into which the stylet is 384l is inserted in FIG. 38. One end of each of one or more filaments (not shown) is threaded through top filament lumen 3842tl and glued through top glue port 3842tp. The other end of each of one or more filaments is looped through the scaffold 3820 (e.g., as shown in FIG. 38), threaded through bottom filament lumen 3842bl and glued through bottom glue port 3842bp. As noted above, during loading, the capsule 3842 passes through the distal end of the outer delivery sheath 3812. At this point, the one or more top filament ends may be cut through the top slot along line L (the capsule 3842 may or may not be cut as well). This will free the top filament end(s) from the capsule 3842. The portion of the capsule 3842 to which the bottom filament end(s) is(are) attached can then be pulled away from the distal end of the outer delivery sheath 3812, allowing each of the one or more filament to be removed from the scaffold 3820 and outer delivery sheath 3812.

Figure 39B:
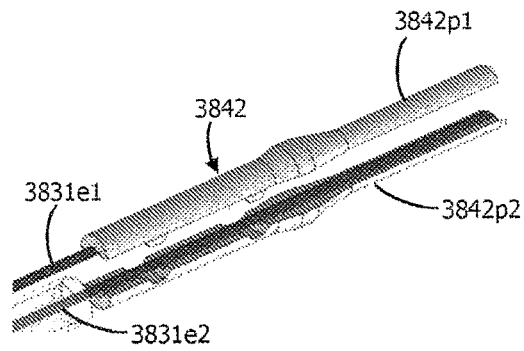
FIG. 39B is a schematic perspective view of a loading capsule, in accordance with another embodiment of the present disclosure.

In an alternative design shown in FIG. 39B, a capsule 3842 is provided which can be manually split into a first portion 3842p1 and a second portion 3842p2. One end 3831e1 of one or more filaments is attached (e.g., using a suitable adhesive) to the first portion 3842p1. After being looped through the scaffold, the other free end 3831e2 of the one or more filaments may be physically clamped between the first and second portions 3842p1, 3842p2. After the capsule 3842 is pulled from the distal end of the outer delivery sheath 3812, the first and second portions 3842p1, 3842p2 may be separated (e.g., split apart), releasing the free end 3831e2 of the one or more filaments. The first portion 3842p1 to which the end 3831e1 of the one or more filaments is attached can then be pulled away from the distal end of the outer delivery sheath 3812, allowing each of the one or more filaments to be removed from the scaffold 3820 and outer delivery sheath 3812.

In another alternative embodiment, one end 3831e1 of one or more filaments is attached (e.g., using a suitable adhesive) to the first portion 3842p1. After being looped through the scaffold, the other end 3831e2 of the one or more filaments is attached (e.g., using a suitable adhesive) to the second portion 3842p2. During advancement of the capsule 3842, the first portion 3842p1 and second portion 3842p2 of the capsule 3842 are joined together. After the capsule 3842 is pulled from the distal end of the outer delivery sheath 3812, the first and second portions 3842p1, 3842p2 may be separated, and the filament cut from one of the portions (e.g., 3842p1). The other of the portions (e.g., 3842p2) can then be pulled away from the distal end of the outer delivery sheath 3812, allowing each of the one or more filaments to be removed from the scaffold 3820 and outer delivery sheath 3812.

Once the stylet 3841, capsule 3842 and one or more filaments 3831 are removed, the system 3800 will be ready for delivery of the scaffold 3820, with the scaffold 3820 overlying the support segment 3814s in a distal section of the delivery sheath 3812. As in other embodiments described herein, one or more retention features may be provided on the support segment 3814s and/or the scaffold 3820 may have a higher force of friction when in contact with the material provided on the support segment 3814s of the inner member 3814 than the scaffold 3820 does when in contact with the material provided on an inner surface of the outer delivery sheath 3812, allowing the support segment 3814s to pull the scaffold 3820 along with the support segment 3814s as the support segment 3814s moves in either a proximal or a distal direction relative to the delivery sheath 3812.

In this way, the scaffold 3820 can be delivered from a distal end of the outer delivery sheath 3812.

For example, in some embodiments, the scaffold 3820 may delivered from a distal end of the outer delivery sheath 3812 directly into an implant location (e.g., a sinus) in a patient.

Figure 40:
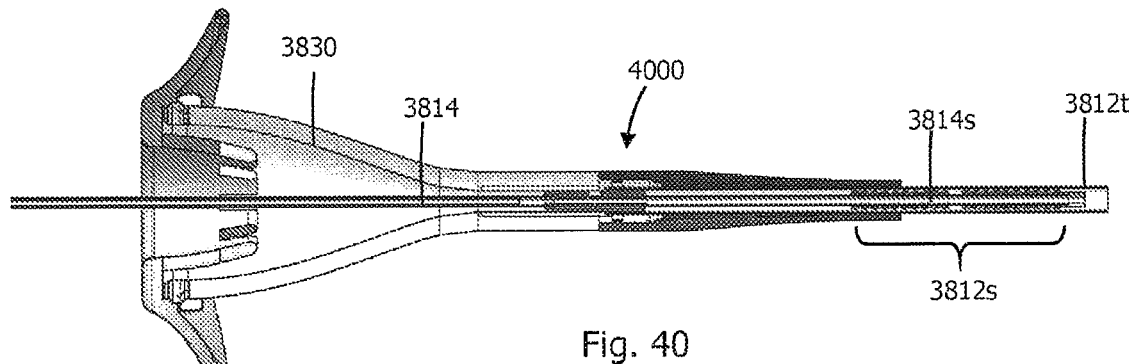
FIG. 40 is a schematic cross-sectional view of a scaffold loading system, in accordance with an embodiment of the present disclosure.
Figure 41:
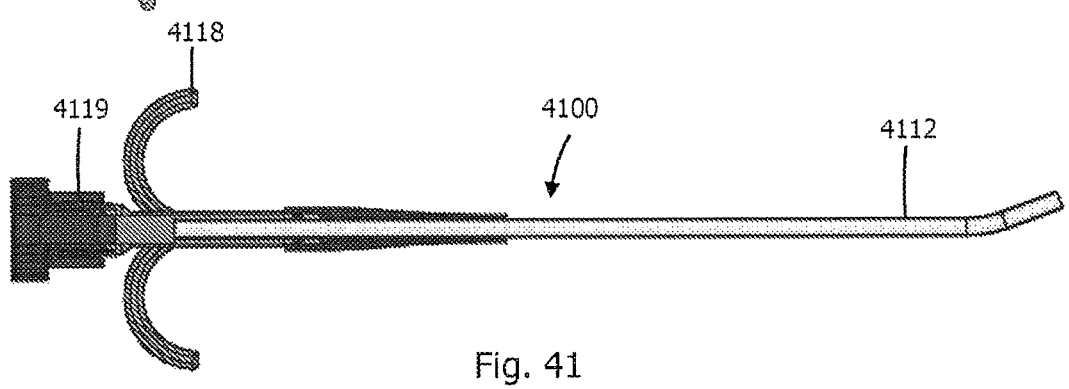
FIG. 41 is a schematic cross-sectional view of an applicator, in accordance with an embodiment of the present disclosure.
Figure 42:
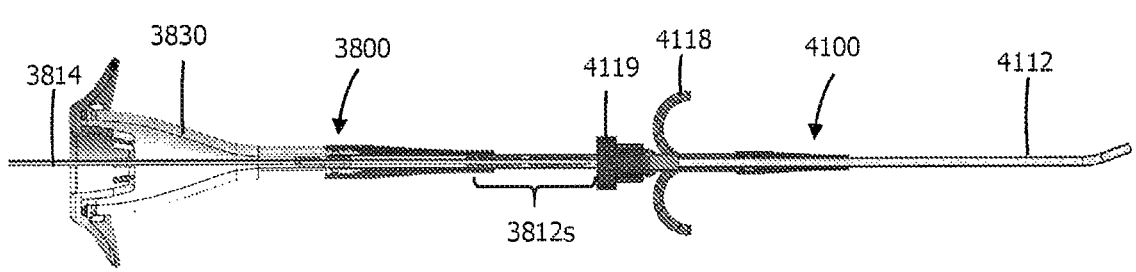
FIG. 42 is a schematic cross-sectional view of the scaffold loading system of FIG. 40 linked to the applicator of FIG. 41, in accordance with an embodiment of the present disclosure.
Figure 43:
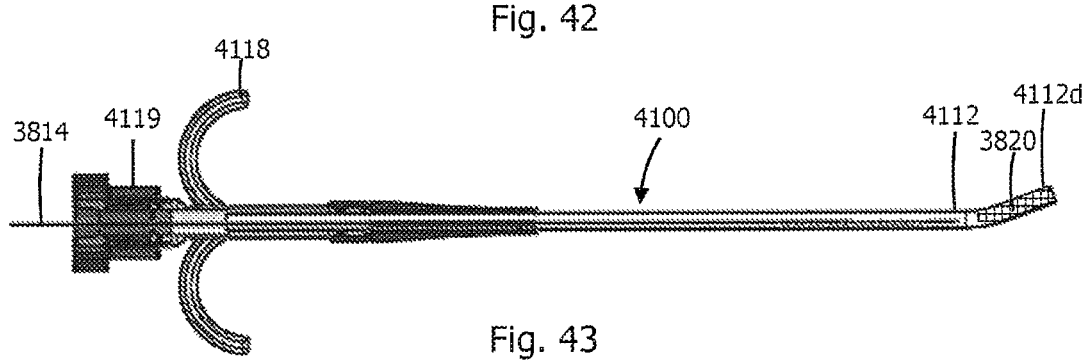
FIG. 43 is a schematic cross-sectional view of an applicator with a loaded scaffold, in accordance with an embodiment of the present disclosure.

As another example, the scaffold 3820 may be delivered into an applicator 4100 (i.e., delivery catheter) like that shown in FIG. 41, which includes an ergonomic handle 4118, a delivery sheath 4112 and an adaptor 4119 (e.g., a Touhy Borst valve with thumb screw closure). For this purpose, a delivery sheath 3812 of a system 3800 like that illustrated in FIG. 38 may be truncated (shortened) to form a truncated loading sheath 3812t of a scaffold loading system 4000 such as that shown in FIG. 40, and a distal end of the truncated loading sheath 3812t may be inserted into valve 4119 or other suitable adaptor at the proximal end of the applicator 4100 of FIG. 41 as shown in FIG. 42. The scaffold (not shown) may be loaded, either before or after the loading system 4000 and applicator 4100 are linked, such that the scaffold overlies a support segment 2814s of an inner member 3814 in a distal section 3812s of the truncated loading sheath 3812t as shown in FIG. 40. Once the loading system 4000 is linked to the applicator 4100, the inner member 3814 can be advanced in order to pull the scaffold through the valve 4119 and into the applicator 4100. For example, the scaffold 3820 may be advanced to a distal end 4112d of the outer delivery sheath 4112 as shown in FIG. 43. In addition, once the scaffold 3820 is transferred from the truncated loading sheath 3812t of system 4000 and into the applicator 4100, if desired, all components of system 4000 may be removed except for inner member 3814, as shown in FIG. 43, which can be used to deliver the scaffold 3820 distally from the applicator 4100 into an implant site within a patient. In some embodiments, the inner member 3814 may be configured such that a portion of the inner member 3814 lying proximal to the support segment 3814s may be disengaged and separated from the support segment 3814s, and an additional elongate member may subsequently be used to advance the support segment 2814s through the outer delivery sheath 4112.

Other loading systems described elsewhere herein, including those shown and described below in FIGS. 36A-36B and in FIGS. 37A-37D, among others, may also be used in an analogous fashion with applicator 4100.

Figure 35:
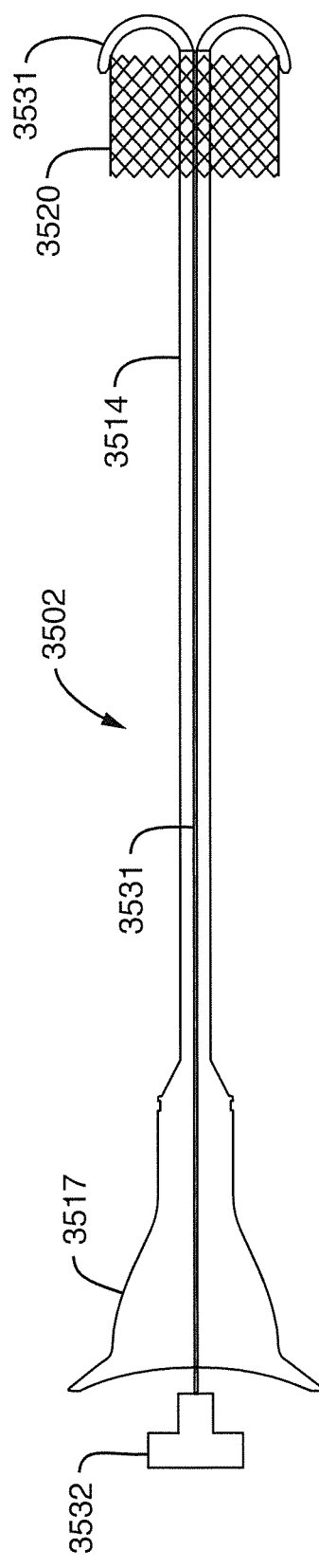
FIG. 35 is a schematic partial cross-sectional side view an assembly for use in a scaffold loading and delivery system, in accordance with an embodiment of the present disclosure.

In another embodiment illustrated in FIG. 35, a second assembly 3502 is shown that includes a hollow inner member 3514 having a lumen (e.g., in the form of a stainless steel hypotube), a press member 3517 (e.g., a molded member) disposed at a proximal end of the hollow inner member 3514 and having a lumen that provides access to the lumen of the hollow inner member 3514, and a scaffold 3520 provided around a support segment (not shown) at a distal end of the inner member 3514. The scaffold 3520 is held in position at the distal end of the inner member 3514 by a plurality of filaments 3531 such that the second assembly can be pushed through a first assembly that comprises a funnel, handle, and delivery sheath as described above (not shown). The plurality of filaments 3531 may be looped from a filament holder 3532 that is positioned at a proximal end of the first assembly 3501, through a lumen in the press member 3517 lumen, through the hollow inner member 3514 lumen, through the scaffold 3420, and back through the hollow inner member 3514 lumen and press member 3517 lumen to the filament holder 3532. Whenever it is desired to remove the one or more filaments 3531 from the scaffold 3520, one can simply sever one end of each filament where it attaches to the filament holder 3532 and subsequently pull the filament holder 3532 proximally to withdrawn the filaments 3531 from the scaffold 3520, hollow inner member 3514 and press member 3517. In certain embodiments, the filament holder 3532 may comprise first and second portions that are separable from one another, and one end of each filament 3531 may be connected to the first portion, while the other end of each filament 3531 may be connected to the second portion. Whenever it is desired to release the scaffold 3520 first assembly 3501, one can simply sever an end of each filament where it attaches to the first portion of the filament holder 3532 and subsequently pull the second portion of the filament holder 3532 proximally to withdrawn the filaments 3531. In certain embodiments, the filament holder 3532 may be provided threaded with threads, such that it can be screwed into a threaded aperture in the pusher member.

In other embodiments, a scaffold may be crimped and loaded into a delivery lumen of a delivery device using a delivery system that includes an engagement device that comprises a plurality of radially expandable and contractible members, each comprising a hook at its distal end.

Figure 12:
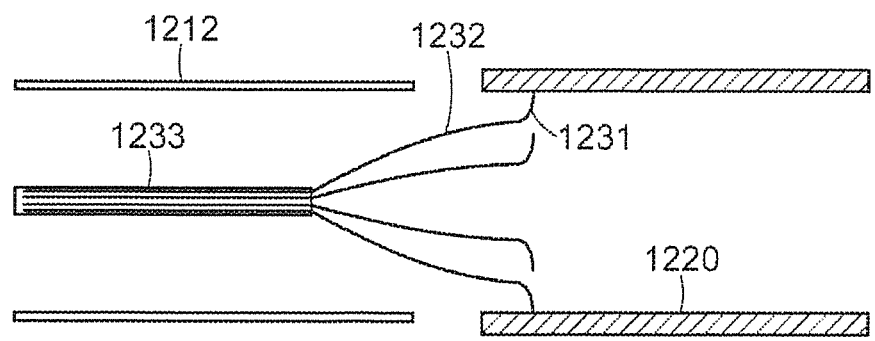
FIG. 12 is a schematic partial cross-sectional side view of a delivery sheath in a process of being loaded with a scaffold, in accordance with an embodiment of the present disclosure.

One example of such a delivery system is found in FIG. 12, which shows a delivery system comprising an engagement device comprising a plurality of radially expandable and contractible members 1232, each comprising a hook 1231 at its distal end. The contractible members 1232 taper radially outward and have a shape memory that allows them to self-expand upon removal of radial compression. The contractible members 1232 and associated hooks 1231 can be routed from the proximal end of the delivery system (not shown) through the distal tip of the delivery sheath 1220. A funnel may be used to assist with the insertion of the hooks 1231 into the delivery system in some embodiments. The contractible members 1232 are associated with an elongate member 1233 by which the contractible members 1232 and hooks 1231 can be pulled proximally into a lumen of a delivery sheath 1212. The hooks 1231 project radially outward and are configured to engage a proximal end of a scaffold 1220. As the contractible members 1232 (which taper radially outward) are drawn into the delivery sheath 1212 (or funnel), the delivery sheath 1212 (or funnel) engages and radially compresses the contractible members 1232, reducing an outer diameter of the scaffold 1220 at its proximal end such that the scaffold 1220 can be drawn into the delivery sheath 1212 (or funnel). The hooks 1231 may ultimately be disengaged from the scaffold 1230 by distally advancing a member with a suitably small diameter lumen over the contractible members 1232, drawing the contractible members 1232 and associated hooks radially inward or, in the case where the hooks reverse direction (e.g., where the hooks are in the shape of a "U" or a "V"), by reversing the direction of the hooks 1231 (e.g., by pushing the elongate member 1233 distally, after which the engagement device may be removed from the distal end of the delivery sheath), among other methods.

Figure 36A:
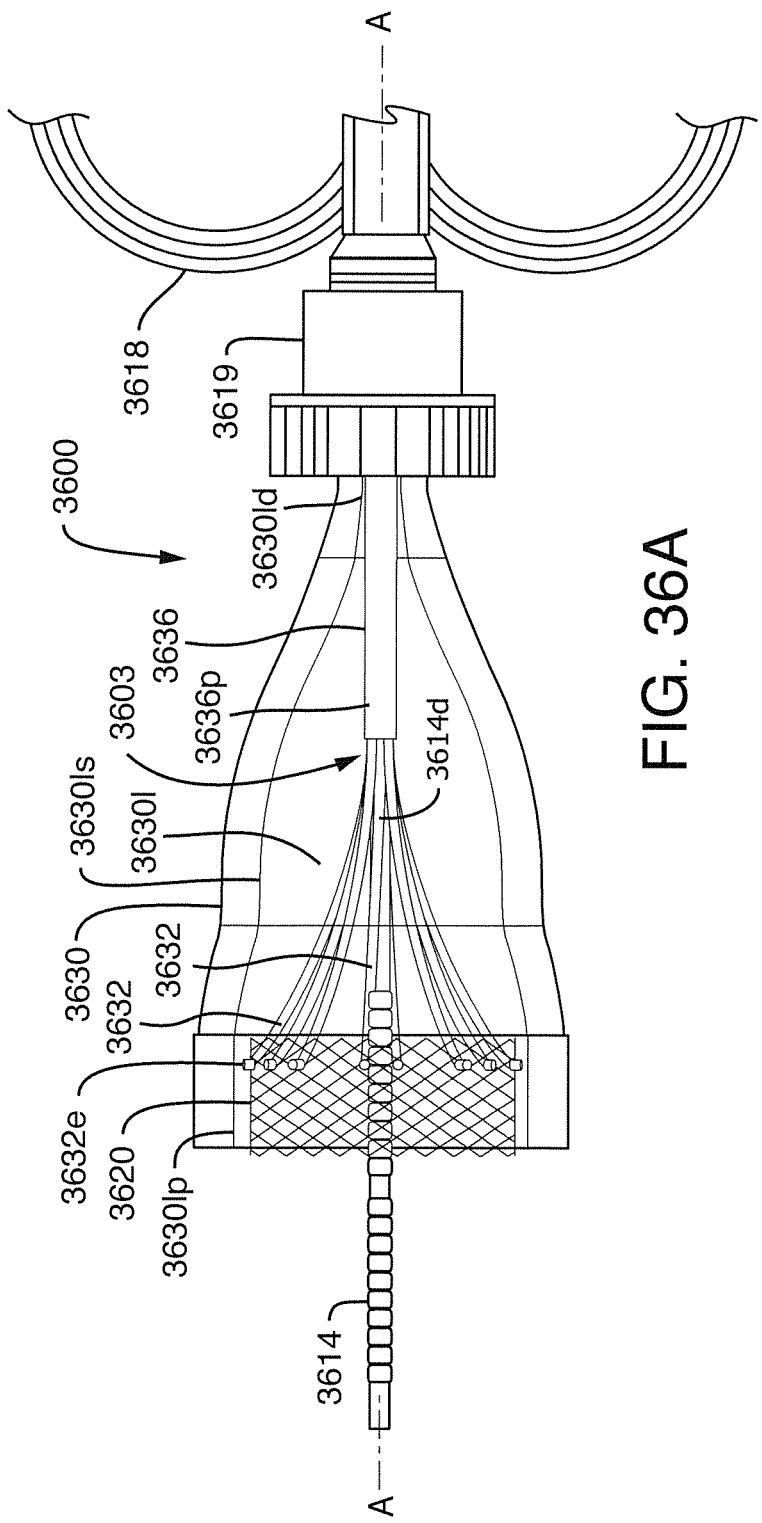
FIG. 36A is a schematic partial side view and FIG. 36B is a schematic partial perspective view of a scaffold loading system, in accordance with an embodiment of the present disclosure.
Figure 36B:
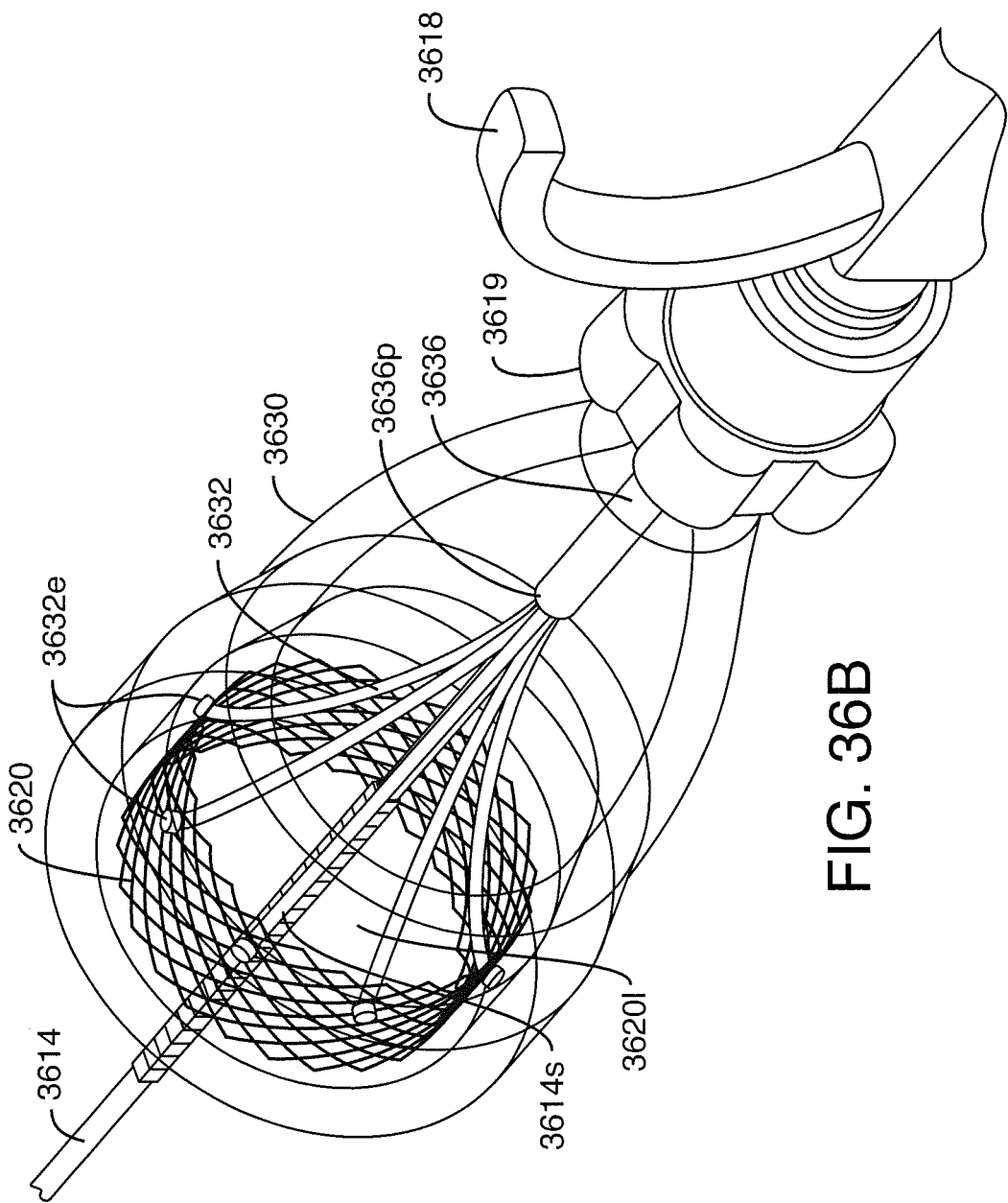

Another embodiment of a delivery system 3600 illustrated in FIGS. 36A and 36B includes a loading member 3630 (e.g., a funnel), an ergonomic handle 3618, an adaptor 3619 (e.g., a Touhy Borst valve with thumb screw closure), and an outer delivery sheath (not shown). The loading member 3630 comprises a loading lumen 3630*l* having a lumen axis, A, a luminal surface 3630*ls*, and a plurality of longitudinal pathways, for instance, keyways (e.g., grooves, slots, etc.), not shown), which are formed in the luminal surface 3630*ls* of the loading member 3630 and which extend longitudinally along a length of the loading member 3630. The loading lumen 3630*l* comprises a tapered lumen region having a proximal tapered lumen end 3630*lp* with a first diameter and a distal tapered lumen end 3630*ld* with a second diameter that is smaller than the first diameter. This and other tapered lumens described herein may be provided with a variety of tapers, including linear tapers, curved tapers (e.g., bell-shaped tapers) and combinations of linear and curved tapers, for example as shown in FIGS. 36A and 36B, where an initial linear taper is followed by a curved (i.e., bell-shaped). While FIGS. 36A-36B illustrate a separate loading member 3630 and ergonomic handle 3618 connected by a valve 3691, it will be appreciated that in other embodiments, these components can be integrated into a combined funnel and handle, for example, like that shown in FIG. 38, if desired.

Also shown is (a) a self-expanding scaffold 3620 having a scaffold lumen 3620*l* that is disposed in the loading lumen 3630*l*, (b) an inner member 3614 having an inner support segment 3614*s*, and (c) an engagement device 3603 having an engagement device axis, A, and a plurality of elongate members 3632, which taper radially outward from the engagement device axis, A, and which have a shape memory that allows the elongate members 3632 to be radially compressed and to subsequently self-expand after upon removal of radial compression. Each of the elongate members 3632 terminates in an engagement feature 3632*e* (e.g., a hook), and the engagement device 3603 is at least partially positioned within the scaffold lumen 3620*l* and loading lumen 3630*l* such that each engagement feature 3632*e* extends through a wall of the scaffold 3620 and into one of the longitudinal pathways in the luminal surface 3630*ls* of the loading member 3630. When so arranged, longitudinal movement of the engagement device 3603, and more specifically, distal longitudinal movement of the engagement device 3603, is accompanied by distal longitudinal movement of the scaffold 3620 within the loading lumen, leading to compression of the scaffold 3620. While the engagement features 3632*e* (e.g., hooks) engage the scaffold 3620 from an interior (luminal) side in the embodiment shown, in other embodiments, the engagement features may be provided which engage the scaffold 3620 from an exterior (abluminal) side.

Figure 36C:
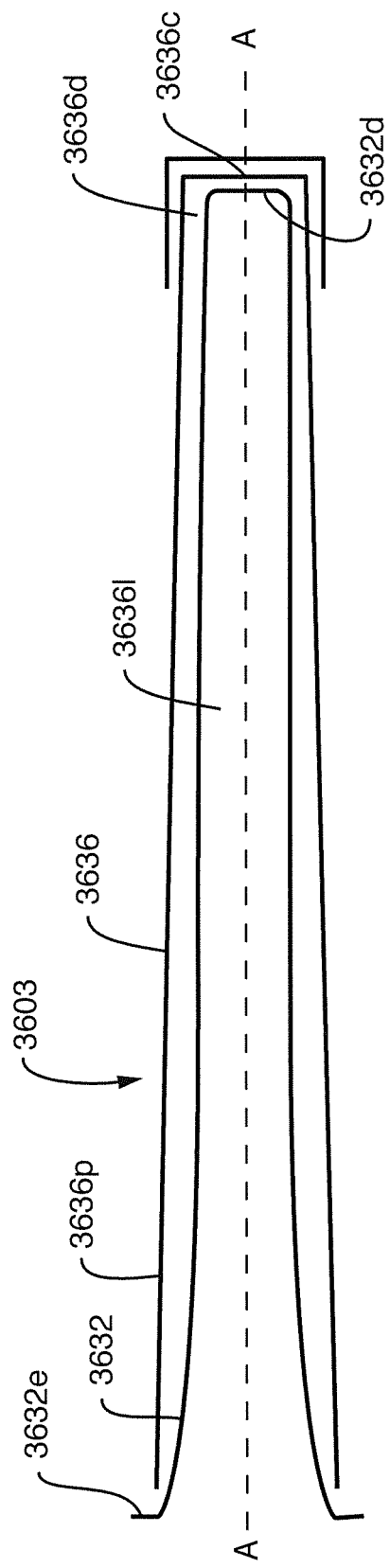
FIG. 36C is a schematic cross-sectional view of an engagement device, in accordance with an embodiment of the present disclosure.

One specific embodiment of an engagement device 3603, shown in FIG. 36C, includes a tubular shaft 3636 having a lumen 3636*l*, an axis, A, a proximal end 3636*p*, and a distal end 3336*d*. The tubular shaft 3636 serves as a detachment sleeve, which will be discussed in more detail below. A plurality of elongate members 3632, each terminating at an engagement features 3632*e*, specifically, a hook tab, extend through the lumen of the tubular shaft 3636 and extend proximally from the proximal end 3636*p* of the tubular shaft 3636, tapering radially outward from the longitudinal axis, A, of the tubular shaft 3636. A removable cap 3636*c* is disposed over the distal end 3636*d* of the tubular shaft 3636, and a distal end 3932*d* of each elongate member 3632 is attached to the cap 3636*c* by a suitable technique (e.g., adhesive, welding, etc.), such that disengaging the cap 3636*c* and pulling the cap 3636*c* from the tubular shaft 3636 allows the elongate members 3632, and associated hook tabs 3632*h*, to be pulled through the tubular shaft 3636 and removed from the delivery system.

Turning again to FIGS. 36A and 36B, it can be seen that by pushing a distal end 3614*d* of the inner member 3614 against proximal end 3636*p*, the engagement device 3603 may be advanced through the loading member 3630 (with the keyways in the funnel acting as guides for the engagement feature 3632*e* (e.g., hook tabs), valve 3619, handle 3618, and through at least a portion of the length of the outer delivery sheath (not shown).

In an alternative embodiment, a hollow inner member 3814 may be employed and a stylet may extend from a proximal end (not shown) of the hollow inner member 3614, through the hollow inner member 3614, out of a distal end 3614*d* of the hollow inner member 3614 and into contact with the engagement device 3603, thereby maintaining a longitudinal spacing between the distal end of the hollow inner member 3614 and the engagement device 3603. A stylet interface (e.g., a receptacle) analogous to that used with capsule 3842 in FIG. 39A described above may be provided in the engagement device 3603 to ensure proper engagement between the stylet and the engagement device 3603.

As the engagement device 3603 is advanced, the engagement features 3632e engage and pull the scaffold through the loading member 3620, valve 3619, handle 3618, and a portion of the length of the outer delivery sheath (not shown). Advancement of the scaffold 3620 and inner support segment 3614s through the funnel 3630 causes the scaffold 3620 to be compressed onto the inner support segment 3614s to a diameter suitable for advancement into the valve 3619, handle 3618, and outer delivery sheath. As previously discussed, the scaffold 3620 may have a higher force of friction when in contact with the material provided on an outer surface of the inner support segment 3614s than it does when in contact with the material provided on an inner surface of the outer delivery sheath, allowing the support segment 3614s to pull the scaffold 3620 along with the support segment 3614s when the support segment 3614s is moved in either a proximal or a distal direction relative to the outer delivery sheath, such that advancement/retraction of the inner support segment 3614s causes advancement/retraction of the scaffold 3620. Alternatively or in addition, movement of the scaffold 3620 may be coordinated with movement of the elongate inner member 3614, for example, by providing one or more retention features on the inner support segment 3614s (e.g., steps, bumps, hooks, barbs, rings, etc.) that engage at least a portion of the scaffold 3620. In some embodiments, the plurality of longitudinal pathways formed in the luminal surface 3630ls of the loading member 3630 are in the form of grooves which have a depth that gradually diminishes as one approaches the distal end of the loading member 3630, causing the engagement features to draw radially inwards, thereby facilitating distal movement of the engagement features 3632e from the loading member 3630.

Once the distal end 3636d of the tubular shaft 3636 emerges from a distal end of the outer delivery sheath (not shown), the cap 3636c can be removed from the distal end 3636d of the tubular shaft 3636. Because each elongate member 3632 is attached to the cap 3636c, the elongate members 3632 can be pulled from the tubular shaft 3636 by means of the cap 3636c, while at the same time maintaining the position of the tubular shaft 3636 within the outer delivery sheath as the cap 3636c and elongate members 3632 are removed. After removal of the cap 3636c and elongate members 3632, the tubular shaft 3636 can be removed from the outer delivery sheath as well.

Figure 13A:
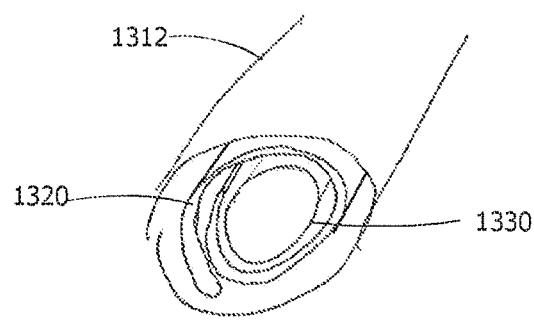
FIG. 13A is a schematic end view of a scaffold, loading member and delivery sheath, in accordance with an embodiment of the present disclosure.

In other embodiments, a scaffold may be selected which can be wrapped around a loading member and inserted into a delivery lumen of a delivery device, after which the loading member is disengaged from the scaffold. Referring to FIG. 13A, a scaffold 1320 may be flattened and rolled around a loading member in the form of a solid or tubular elongate member 1330 in an overlapping folded manner, after which the scaffold 1320 and loading member 1330 are loaded into a delivery lumen in an delivery sheath 1312. After the loading member 1330 and scaffold 1320 are loaded into the delivery sheath 1312 (from either the proximal or the distal end of the delivery system), the loading member 1330 may be removed. Upon deployment (e.g., using a suitable pusher member), the scaffold 1320 will unfurl, allowing controlled expansion at a targeted deployment location.

Figure 13B:
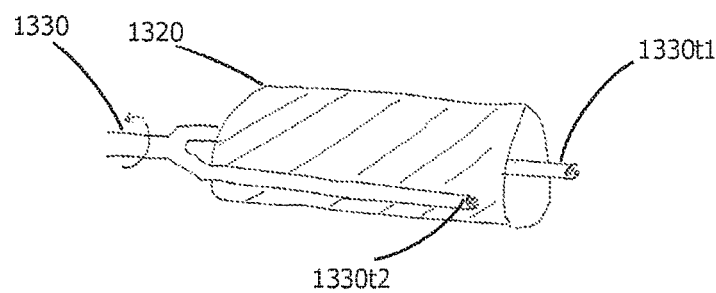
FIG. 13B and FIG. 13C are schematic perspective views showing a scaffold and a two-tined loading member, before and after winding of the scaffold on the loading member, in accordance with an embodiment of the present disclosure.
Figure 13C:
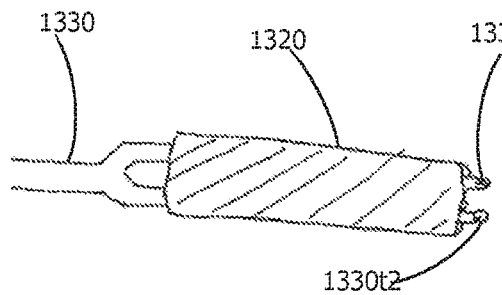
Figure 13D:
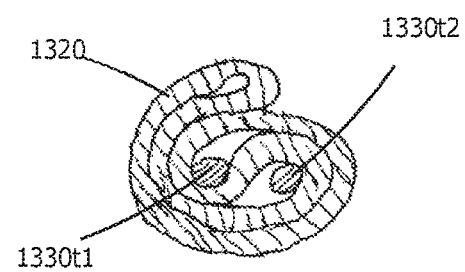
FIG. 13D is a schematic cross-sectional view showing the scaffold and two-tined loading member after winding of the scaffold on the loading member.

In a related embodiment, and with reference to the cross-section shown in FIG. 13B, a scaffold 1320 may be loaded onto a loading member comprising a pair of tines 1330t1, 1330t2 such that one tine 1330t1 is placed in the lumen of the scaffold 1320 and the other tine 1330t2 placed on the outside of the scaffold 1320. The scaffold 1320 may then be flattened and wrapped around the tines 1330t1, 1330t2 of the loading member, or the tines 1330t1, 1330t2 of the loading member may be rotated to wind up the scaffold 320, such that the scaffold 1320 is wrapped around the tines 1330t1, 1330t2 in an overlapping manner as shown in FIG. 13B. The scaffold may be subsequently loaded into a delivery lumen of a delivery catheter 1312, after which the loading member may be removed from the scaffold.

Other aspects of the disclosure pertain to catheters and delivery systems that are useful in the deployment of scaffolds in a sinus cavity of a patient.

In various embodiments, an external guide catheter is employed for navigation and positioning of the scaffold. In these embodiments, the delivery system may include a) a guide catheter comprising a guide catheter lumen, (b) a delivery catheter comprising a sheath with a delivery lumen (e.g., associated with an outer sheath), where the delivery catheter is dimensioned to be inserted through the guide catheter, and (c) a scaffold that is adapted to be placed into and delivered from the delivery lumen. An external guide catheter may be useful, for example, in accessing the sinus space and providing cannulation and access to smaller or more difficult to reach regions of the sinus. In certain embodiments, the external guide catheter may be provided with increased stiffness to allow for manipulation of surrounding tissue and to provide an unimpeded channel for sinus access. A delivery catheter containing a scaffold may then be routed through this guide catheter lumen for direct access to the treatment area within the sinus. Such a system may enable access to occur with minimal tissue removal.

In various embodiments, catheters are provided which comprise a sheath having a section with a shape memory (referred to herein as a "shape-memorized section") such that the section has a curvature when the sheath is in an unconstrained state. The shape-memorized section may have a curvature that ranges, for example, from 0 to 135 degrees, among other values. The curvature of the shape-memorized section may correspond to an arc having a length that ranges, for example, from 1 to 50 mm, among other possible values.

In certain embodiments, the catheter is a guide catheter and the sheath is a guide sheath that comprises a guide lumen through which a delivery catheter may be advanced. The guide sheath may be pre-formed to a specific curved geometry to allow access to challenging locations within the sinus.

In certain embodiments, the catheter is a delivery catheter and the sheath is a delivery sheath that comprises a delivery lumen from which a scaffold may be delivered. The delivery sheath may be pre-formed to specific curved geometries to allow access to sinus ostia. In this way, each ostium may have a dedicated form to support access. The delivery sheath may be provided with sufficient stiffness to allow for tissue manipulation and allow access without removing tissue.

One catheter of this type is shown in FIG. 5D (previously described), which illustrates a delivery catheter 510 having a delivery sheath 512. The delivery sheath 512 has a shape-memorized section 512s that has a curvature when the sheath is in an unconstrained state. The curved shape-memorized section 512s in the embodiment shown is approximately 80 degrees.

In certain embodiments, delivery systems are provided that include a linear elongate member (e.g., a wire or rod) that is configured for insertion into and removal from a lumen of the sheath having a curved shape-memorized section. The linear elongate member is of sufficient stiffness such that, when inserted into a lumen (e.g., delivery lumen, guide lumen, etc.) of the sheath the curvature of the shape-memorized section is substantially eliminated. The elongate member may also be pulled proximally, thereby allowing the shape-memorized section to bend and provide access accordingly.

Figure 14:
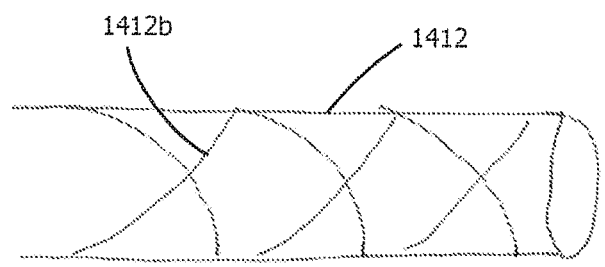
FIG. 14 is a schematic view of a braided sheath, or braid embedded within a polymer sheath, in accordance with an embodiment of the present disclosure.

In various embodiments, catheters (e.g., guide catheters, delivery catheters, etc.) are provided which comprise a sheath that is configured to be custom bent to a curvature that is dependent upon user preference. For example, with reference to FIG. 14, a stiff, malleable metal braid 1412b, such as a braid formed from nitinol, may be incorporated onto and/or into a catheter sheath 1412. The use of such a sheath 1412 allows the catheter to be bent and manipulated on demand by a health care provider. The metal braid 1412b may also act to resist kinking in the sheath 1412.

In various embodiments, the above-described catheters may be provided with an additional lumen in addition to the lumen previously described (e.g., delivery lumen, guide lumen, etc.).

The additional lumen may be configured to receive, for example, a stiff elongate member (e.g., a wire or rod) such that insertion of the elongate member into the lumen changes the shape of the catheter. For example, insertion of the elongate member may straighten a non-linear/curved delivery catheter or guide catheter. Conversely, insertion of an elongate member comprising a curved section may be used to provide a custom bend in an otherwise substantially linear delivery catheter or guide catheter. In some embodiments, the elongate member may be configured to be custom bent, depending on user preference.

The additional lumen may be configured to receive, for example, an illumination fiber or a scope for direct visualization (e.g., a fiber-optic-based fiberscope, which may further comprise a suitable illumination system).

In various embodiments, each of the preceding catheters may be provided with a stiffness gradient. For example, the catheter may have a stiffness gradient wherein stiffness decreases in a proximal-to-distal direction. This may, for example, allow for atraumatic navigation of the delivery system to more challenging sinus locations, by allowing the end of lower stiffness to be advanced while reducing risk of tissue damage or perforation. As another example, the catheter may have a stiffness gradient wherein stiffness increases in a proximal-to-distal direction. For example, the catheter may include a malleable metal (e.g., in the form of a metal braid) to allow the user to bend and manipulate the distal tip geometry for customized access.

A stiffness gradient may be provided through multitude of means, including braid variation, variable extrusion, variable diameters, varying wall thicknesses, or by adhering varying stiffness materials (e.g., by heat bonding or using a suitable adhesive) along the length of the catheter, among other techniques.

Figure 15A:
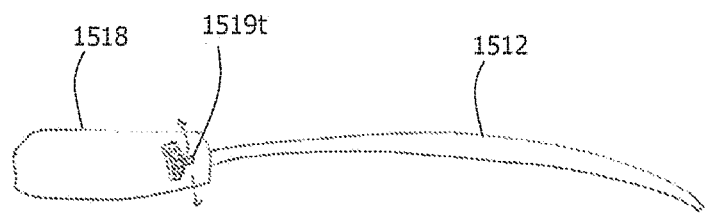
FIG. 15A is a schematic view of a catheter and handle, in accordance with an embodiment of the present disclosure.
Figure 15B:
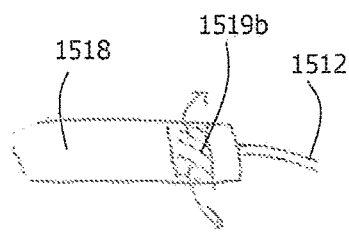
FIG. 15B is a schematic view of a catheter (partial) and handle, in accordance with an embodiment of the present disclosure.

In various embodiments, the above-described catheters may be provided with a mechanism whereby an outer catheter sheath (e.g., guide sheath, delivery sheath, etc.) may be rotated relative to a handle. For example, with reference to FIGS. 15A and 15B, the outer sheath 1512 of a delivery catheter may be anchored to a handle 1518 in a way such that thumb manipulation can be used to steer the tip of the delivery system. Examples of thumb control mechanisms include a left/right toggle switch 1519t (FIG. 15A) or a rotating band 1519b (FIG. 15B) each of which can transmit rotational force to the outer sheath 1512. In other embodiments, the thumb manipulation may be used to advance or retract inner support members or any layer of sheaths within the system. Systems of this type may be used, for example, in conjunction with catheters having a pre-formed curvature or an adjustable curvature to allow for navigational flexibility.

Other aspects of the disclosure pertain to catheters and delivery systems in which a distal end of an outer sheath of the delivery system is folded back over itself.

Figure 16:
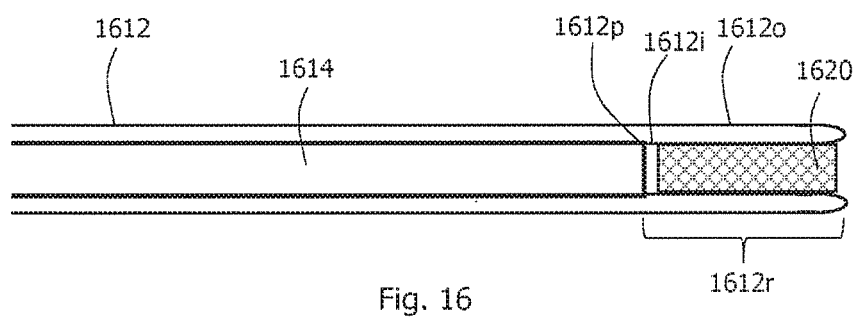
FIG. 16 is a schematic partial cross-sectional view of a loaded delivery catheter in accordance with an embodiment of the present disclosure.

Referring to FIG. 16, a delivery system may be provided comprising an elongate inner member 1614 and a flexible outer sheath 1612, a distal end of which is folded into itself forming a region of double outer sheath thickness 1612r at a distal end of the delivery system. The region of double outer sheath thickness 1612r comprises an inner layer 1612i and an outer layer 1612o and forms a delivery lumen that is dimensioned to receive a radially self-expandable scaffold 1620. The inner layer 1612i of the outer sheath 1612 is anchored at point 1612p to a distal end of the elongate inner member 1614, which can provide a mechanical stop for the expandable scaffold 1620. By proximately pulling back the outer layer 1612o relative to the elongate inner member 1614, or by distally advancing the elongate inner member 1614 distally relative to the outer layer 1612o, or both, the sheath 1612 is rolled back such that the region of double thickness 1612r gradually shortens and the scaffold 1620 that is radially constrained within the region of double thickness 1612r is gradually released. In some embodiments, the outer sheath 1612 may not continue for the entire length of the delivery system. In this case, the outer sheath 1612 may be, for example, pulled back to release the scaffold by attachment to a member such as a collar which is then proximately pulled back by a wire or wires, an outer braid or other suitable means. Suitable materials for the sheath include flexible materials with a relatively low coefficient of friction, for example, a fluoropolymer such as polytetrafluoroethylene, among other potential materials.

Other aspects of the disclosure pertain to delivery systems in which at least one filament (e.g., a string, suture, thread, wire, tape, ribbon, strip, etc.) is used to deploy a self-expanding scaffold.

Figure 18A:
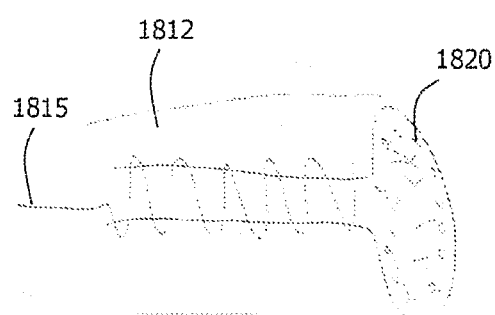
FIG. 18A is a schematic view of a scaffold, sheath and filament, in accordance with an embodiment of the present disclosure.

In some embodiments, and with reference to FIG. 18A, a filament 1815 may be used to secure a rolled outer sheath 1812 at a distal end of the delivery device. The rolled outer sheath 1812 contains the scaffold 1820 to be delivered. Pulling on the filament 1815 in a proximal direction releases the portion of the outer sheath 1812 secured by the filament 1815, allowing the scaffold 1820 to expand into the deployment space without pushing or pulling of either an inner member (not shown) or the sheath 1812 itself.

Figure 18B:
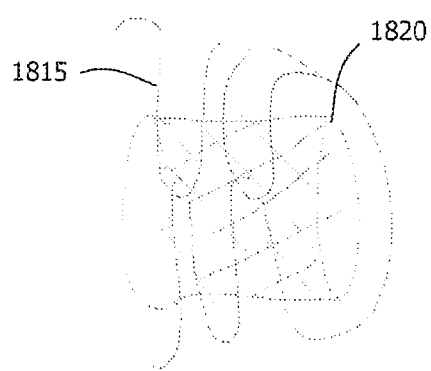
FIG. 18B is a schematic view of a scaffold and filament, in accordance with an embodiment of the present disclosure.

In other embodiments, the filament itself may be used to secure the scaffold in a radially contracted state. For example, and with reference to FIG. 18B, a filament 1815 in the form of a knit may be used to secure and maintain the scaffold 1820 in a compressed state at the distal end of the delivery system. The ends of the knitted filament 1815 may be routed to the user, for example, along the outside of the delivery system, down a dedicated lumen within the delivery system, or inside an outer sheath of the delivery system, among other options. Pulling the filament(s) in the proximal direction releases the scaffold to the target space.

Figure 19A:
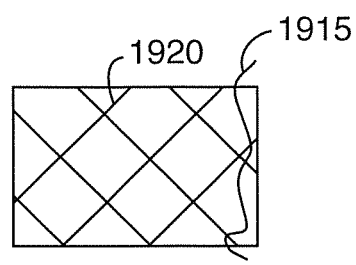
FIG. 19A is a schematic side view of a scaffold and filament, in accordance with an embodiment of the present disclosure.
Figure 19B:
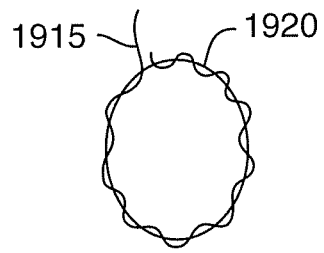
FIG. 19B is a schematic end view of the scaffold and filament of FIG. 19A.
Figure 19C:
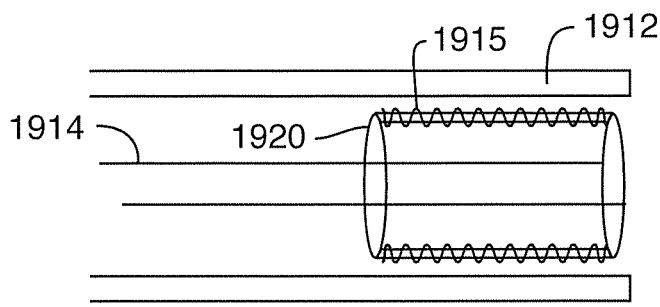
FIG. 19C is a schematic partial cross-sectional view of a loaded delivery catheter, in accordance with an embodiment of the present disclosure.

As another example, the filament may be used to decrease and/or crimp the diameter of a scaffold for loading in a delivery system and for eventual deployment in a subject. With reference to FIGS. 19A-19B (a schematic side view is shown in FIG. 19A and a schematic end view is shown in FIG. 19B), one or more filaments 1915 may be woven through the distal end and/or proximal end of a scaffold 1920 allowing the scaffold 1920 to be collapsed uniformly. As shown in FIG. 19C, the scaffold 1920 may be crimped onto an elongate inner member 1914 and the inner member 1914 and scaffold 1920 disposed within an outer sheath 1912. At the time of deployment, the outer sheath 1912 is pulled back. The one or more filaments 2115 may, for example, be cut by a feature provided on the outer sheath 1912 as it is pulled back, or the filament(s) 1915 may be routed back through the delivery system such that an operator can pull on the filament(s) 1915 to release the scaffold 1920 from the inner member 1914 in a fashion analogous to that previously discussed.

Figure 19D:
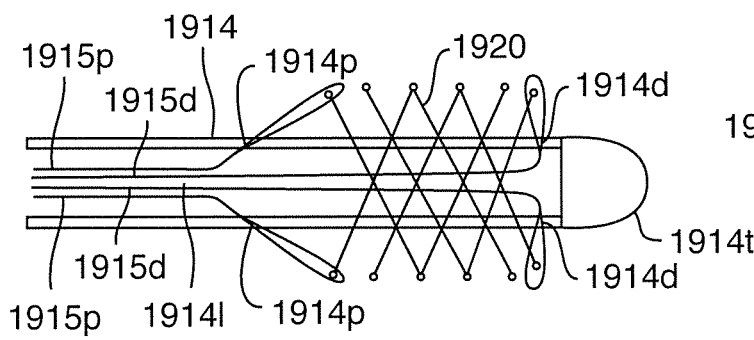
FIGS. 19D and 19E are schematic partial cross-sectional side views of a distal end of a delivery system during scaffold loading, in accordance with an embodiment of the present disclosure.
Figure 19F:
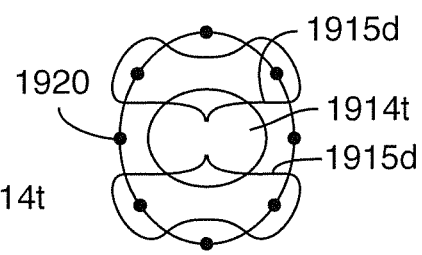
FIG. 19F is a schematic end view of the scaffold and filament of FIG. 19D.
Figure 19E:
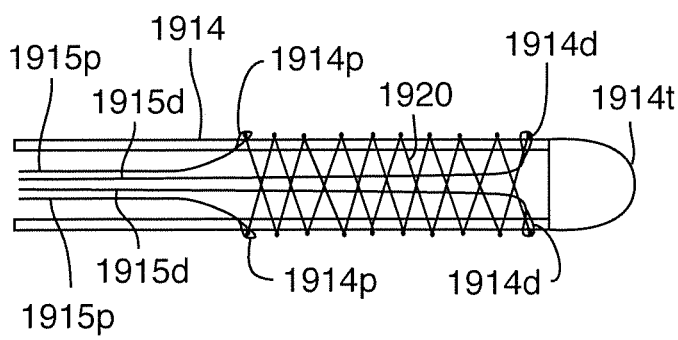

Turning now to FIG. 19D, a schematic partial cross-sectional side view of a distal end of a delivery system is shown during a process of scaffold loading. As seen from this FIG. 19D, the system includes a scaffold 1920 disposed around an elongate inner member 1914 having a lumen 1914*l*. Two proximal filaments 1915*p* are woven through the proximal end of scaffold 1920 and two distal filaments 1915*d* are woven through the distal end of scaffold 1920. Proximal filaments 1915*p* are routed through proximal apertures 1914*p* formed in the elongate inner member 1914 wall, into the elongate inner member lumen 1914*l*, and back through the delivery system. Similarly, distal filaments 1915*d* are routed through distal apertures 1914*d* formed in the elongate inner member 1914 wall, into the elongate inner member lumen 1914*l*, and back through the delivery system. FIG. 19F is a schematic end view illustrating the elongate inner member tip 1914*t*, scaffold 1920 and distal filaments 1915*d* of FIG. 19D, and showing the distal filaments 1915*d* woven around nodes of scaffold 1920. This allows for even tensioning of distal filaments 1915*d* while reducing the number of distal filaments 1915*d* employed. Turning now to FIG. 19E, a schematic partial cross-sectional side view of the distal end of the delivery system of FIG. 19D is shown, after pulling the filaments 1915*p*, 1915*d* proximally and placing the filaments 1915*p*, 1915*d* in tension, which acts to elongate the scaffold 1920 and compress the scaffold 1920 onto the elongate inner member 1914, thereby placing the scaffold into a configuration suitable for delivery. After being positioned at a target site in a subject, the scaffold may be allowed to self-expand by removing the tension placed on the filaments 1915*p*, 1915*d* and delivery may be completed by releasing the filaments 1915*p*, 1915*d* from the scaffold (e.g., as previously discussed) and withdrawing the delivery system from the subject.

Figure 19G:
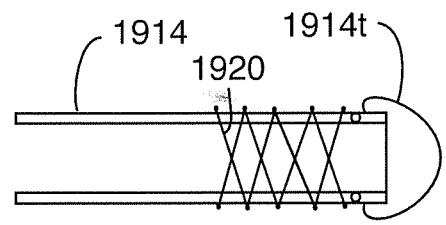
FIG. 19G is a schematic partial cross-sectional view of an alternate embodiment of the distal tip in FIG. 19E (filaments not shown).

FIG. 19G is a schematic partial cross-sectional view of an alternate embodiment of the distal tip 1914*t* for the elongate inner member 1914 in FIG. 19E (filaments 1915*p*, 1915*d* not shown).

Figure 17A:
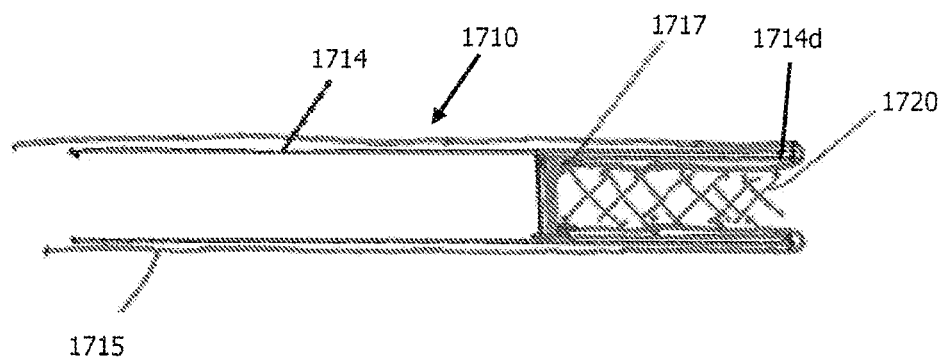
FIGS. 17A and 17B are schematic partial cross-sectional side views of a distal end of a scaffold delivery system, before and during deployment of a scaffold, in accordance with an embodiment of the present disclosure.
Figure 17B:
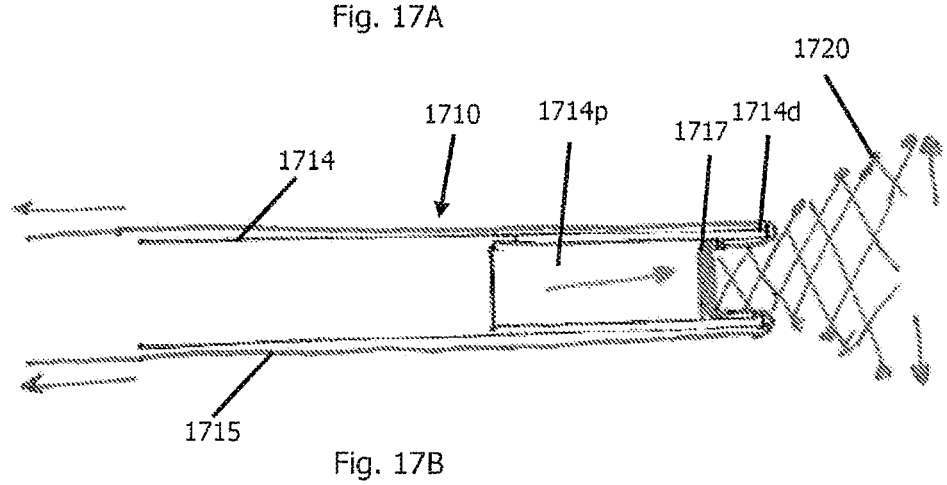

In some embodiments, one or more filaments may be employed to pull the scaffold out of a pocket formed at the distal end of the delivery catheter. In one specific example illustrated in FIGS. 17A and 17B a delivery device 1710 is provided having an elongate delivery member 1714 with a pocket 1714*p* formed in a distal end thereof. The scaffold 1720 is disposed in the pocket 1714*p* during delivery. An expulsion member 1717 (e.g., a movable component in the form of a disc, ring, etc.) is disposed proximal to the scaffold 1720 in the pocket 1714*p*, and attached to the expulsion member 1717 are one or more filaments 1715 (e.g., strings, sutures, threads, wires, lengths of tape, ribbons, strips, etc.), which are routed out of the distal end 1714*d* of the delivery member 1714 where they reverse direction. In various embodiments, the filaments 1715 (or extensions thereof) extend to the proximal end (not shown) of the delivery member 1714, allowing the filaments 1715 to be actuated (i.e., pulled) by a user. In the embodiment shown, by pulling the filaments 1715 in a proximal direction as shown by the arrows in FIG. 17B, the expulsion member 1717 advances distally and delivers the scaffold 1720 from the pocket 1720*p* and into a targeted delivery area. The delivery catheter 1710 may be used independently, as shown, or may be used in conjunction with a guide catheter as previously described herein. The filaments 1715 extend along an outside surface of the delivery member 1714 in the embodiment shown. However, in other embodiments, the elongate flexible members 1715 may be routed through one or more channels or grooves that are formed in the surface of the delivery member 1714 or through one or more internal lumens that are formed within the delivery member 1714 (not shown). Although the one or more filaments 1715 are attached to an expulsion member 1717 in the embodiment shown, in other embodiments, the one or more filaments 1715 may be temporarily attached to a proximal end of the scaffold 1720 to affect delivery.

In another embodiment, a tubular membrane is substituted for all or part of the length of the filaments 1715. The tubular membrane may be closed or open at the distal-most end. In one particular embodiment, the distal-most portion of the tubular membrane may be closed and may be folded back into the pocket 1720*p* and around the scaffold 1720. The proximal end of the tubular membrane may be connected to one or more filaments extended to the proximal end of the delivery member. The user may deliver the scaffold 1720 by pulling on the filaments which in turn pulls the membrane out of the pocket 1720*p*, thereby delivering the scaffold 1720.

Figure 20A:
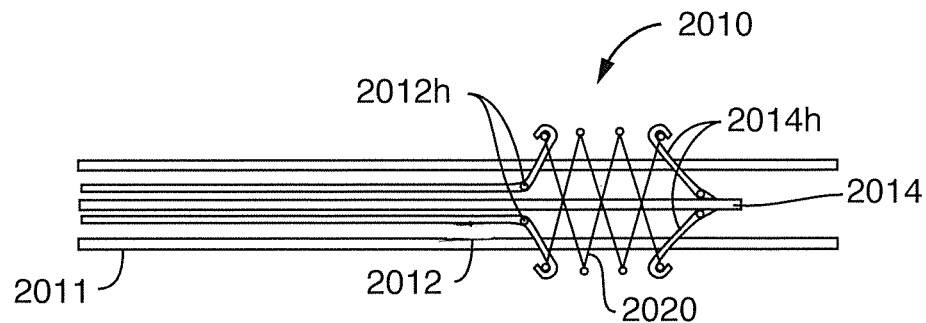
FIG. 20A and FIG. 20B are schematic partial cross-sectional side views of a distal end of a delivery system during scaffold loading, in accordance with an embodiment of the present disclosure.
Figure 20B:
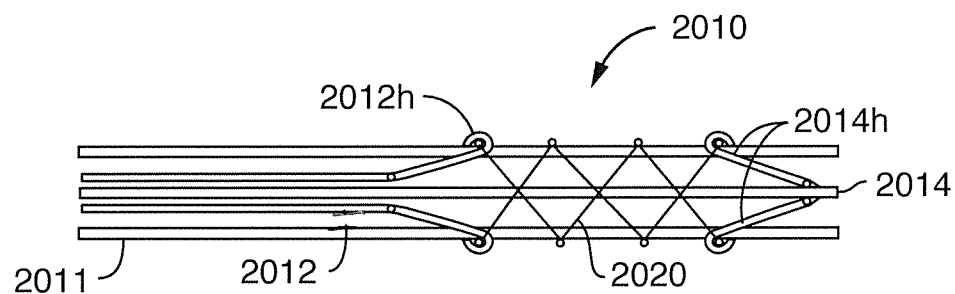

In other aspects of the present disclosure, elongate inner and outer members are employed to longitudinally lengthen, and thus radially contract a self-expanding braided scaffold. In one specific example illustrated in FIGS. 20A and 20B, a delivery device 2010 is shown disposed within a guide catheter or other access sheath 2011. The delivery device 2010 includes (a) an elongate outer sheath 2012 having an attachment feature (e.g., attached hooks 2012*h*) and (b) an elongate inner member 2014 having an attachment feature as well (e.g., attached hooks 2014*h*), the elongate inner member 2014 being at least partially disposed within the elongate outer sheath 2012. An expanded scaffold 2020 is shown in FIG. 20A, with hooks 2012*h* and 2014*h* reversibly attached to opposing ends of the scaffold 2020. Hooks 2012*h* and 2014*h* are hinged or are flexible such that when the elongate inner member 2014 is advanced while maintaining the position of the outer sheath 2012 and/or when the elongate outer sheath 2012 is retracted while maintaining the position of the elongate inner member 2014, the scaffold 2020 increases in length and decreases in diameter, such that the scaffold 2020 collapses onto the elongate outer sheath 2012 as shown in FIG. 20B. The scaffold 2020 may be released by reversing the process (i.e., by retracting the elongate inner member 2014 while maintaining the position of the elongate outer sheath 2012 and/or by advancing the elongate outer sheath 2012 while maintaining the position of the elongate inner member 2014). Although the catheter 2010 is configured such that the scaffold 2020 collapses onto the elongate outer sheath 2012 in the embodiment shown in FIGS. 20A and 20B, in other embodiments, the outer sheath 2012 does not extend distally beyond hooks 2012*h*, such that the scaffold 2010 collapses onto the elongate inner member 2014.

Figure 21:
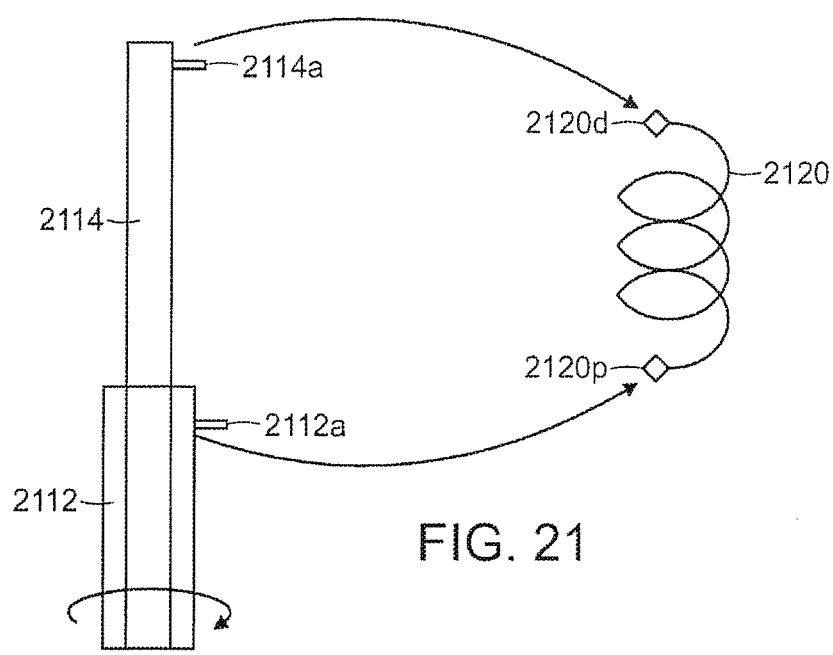
FIG. 21 is a schematic view of a distal end of a delivery catheter and a spiral scaffold, in accordance with an embodiment of the present disclosure.

Other aspects of the disclosure pertain to delivery systems in which a spiral (e.g., helical) scaffold is delivered. In some embodiments, and with reference to FIG. 21, the delivery system may comprise (a) a spiral scaffold 2120 having a distal end 2120*d* and a proximal end 2120*p* and (b) delivery catheter comprising (i) an outer member 2112 having a distal end and an outer member attachment feature 2112*a* proximate the outer member 2112 distal end and (ii) an inner member 2114 having a distal end and an inner member attachment feature 2114*a* proximate the inner member 2114 distal end, wherein the inner member attachment feature 2114*a* is adapted to become attached to the scaffold distal end 2120*d* and the outer member attachment feature 2112*a* is adapted to become attached to the scaffold proximal end 2120*p*. Once the inner member attachment feature 2114*a* is attached to the scaffold distal end 2120*d* and the outer member attachment feature 2112*a* is attached to the scaffold proximal end 2120*p*, rotation of the outer member 2112 relative to the inner member 2114 in the direction shown results in contraction of the spiral scaffold 2120 and rotation of the outer member 2112 relative to the inner member 2114 in the opposing direction results in expansion of the spiral scaffold 2120.

Thus, the delivery system shown provides a means for anchoring and delivering a spiral scaffold 2120 design. In the design shown in FIG. 21, the inner member is in the form of an inner sheath 2124 and the inner member attachment feature is in the form of an anchoring hook 2114*a* which hooks a loop formed at the distal end 2120*d* of the scaffold 2120. The outer member, on the other hand, is in the form of an outer sheath 2112 and the outer member attachment feature is in the form of an anchoring hook 2112*a* which hooks a loop formed at the proximal end 2120*p* of the scaffold 2120. By turning the outer sheath 2112 in the same direction as the spiral wrap of the scaffold 2120, the scaffold 2120 can be tightened around the outer diameter of the inner member 2114. For deployment, rotating the outer sheath 2112 against the direction of the spiral will allow the scaffold 2120 to release in the target implant location. The hooks 2112*a*, 2114*a* disengage after the outer member has been rotated to the point where surrounding tissue is contacted and expansion of the scaffold 2120 ceases.

Figure 22:
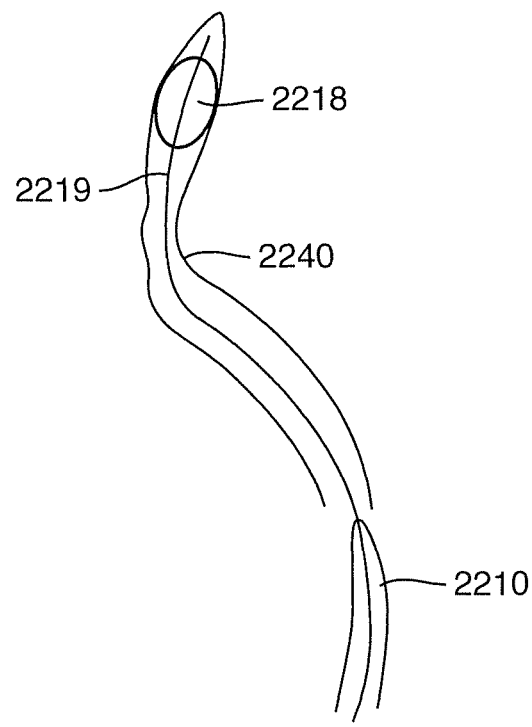
FIG. 22 is a schematic view of a delivery system including an anchoring balloon, in accordance with an embodiment of the present disclosure.

Still other aspects of the disclosure pertain to delivery systems in which a distal anchoring device is used to assist with scaffold delivery. In these aspects, and with reference to FIG. 22 a balloon 2218 may be inflated in a sinus 2240 on a distal side of a desired implantation site (e.g., distal to a sinus ostium). The balloon provides an anchor and a tracking point for implant delivery, and a flexible tracking member 2219 is routed to the exterior section of the nasal cavity. A loaded delivery system 2210 may then be routed over the tracking member 2219 for delivery of the implant near or at the ostia. A loaded delivery system 2210 may comprise a soft trackable distal section in some embodiments. After scaffold delivery, the unloaded delivery system may be removed, followed by deflation of the balloon and withdrawal of the anchoring device.

Other aspects of the present disclosure pertain to systems in which a scaffold is released, followed by balloon expansion within the scaffold. Balloons for use in conjunction with this aspect of the present disclosure may have an inflated diameter ranging, for example, from 4 mm to 25 mm, for example, ranging from 4 mm to 7 mm for smaller sinus spaces and ranging from 18 mm to 22 mm for larger sinus spaces (e.g., the ethmoid post-surgical space), among other sizes. In certain embodiments, (e.g., a scaffold is deployed in a post-surgical spaces of irregular geometry, for instance, the ethmoid post-surgical space), it may be desirable to employ a compliant balloon such that the balloon can better conform to the irregular geometry of the space. In other embodiments, it may be desirable to employ a non-compliant balloon, thereby allowing higher pressures to be employed.

Figure 23:
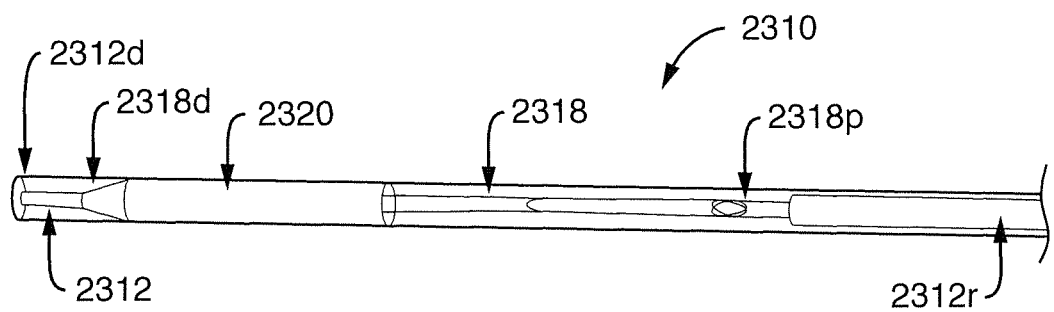
FIG. 23 is a photograph illustrating a scaffold delivery system, in accordance with an embodiment of the present disclosure.
Figure 23A:
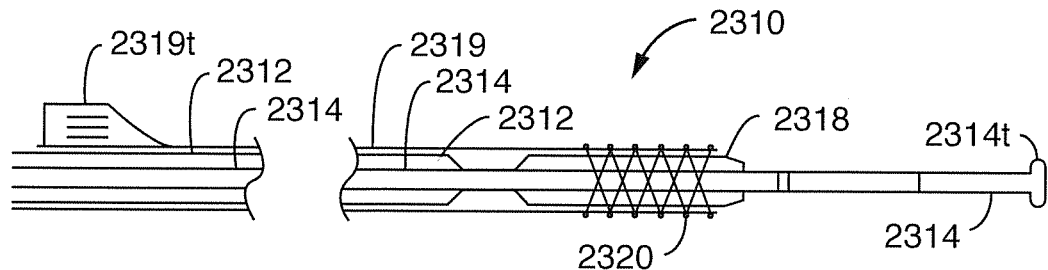
FIGS. 23A, 23B and 23C are schematic partial cross-sectional side views of a distal end of a scaffold delivery system, shown at three stages of deployment of a scaffold, in accordance with an embodiment of the present disclosure.

In one specific example illustrated in FIG. 23, a delivery assembly 2310 is shown which includes an outer sheath 2312 having a distal end 2312*d*, and a balloon catheter comprising a balloon 2318 having a proximal end 2318*p* and a distal end 2318*d* disposed within an outer delivery sheath 2312. A scaffold 2320 is disposed on an outer surface of the balloon 2318 within the outer delivery sheath 2312. While the length of the balloon 2318 is significantly greater than that of the scaffold 2320 in the embodiment shown, in other embodiments the length of the scaffold 2320 and balloon 2318 may be more closely matched. Also included in the embodiment shown is a stiff support tube 2312*r* which is provided within the outer delivery sheath 2312 and which provides stiffness support for the outer delivery sheath 2312 over a proximal portion of its length. In this embodiment, the scaffold 2320 has a higher force of friction when in contact with the material provided on the outer surface of the balloon 2318 than it does when in contact with the material provided on the inner surface of the outer delivery sheath 2312, allowing the balloon 2318 to advance the scaffold 2320 out of a distal end 2312*d* of the outer sheath 2312, followed by inflation of the balloon 2318. In this regard, it is noted that the excess length of the balloon 2318 in the embodiment shown increases the tolerance of the system to any slippage that may occur between the balloon 2318 and stent 2310.

In another specific example illustrated in FIGS. 23A-23D, a delivery assembly 2310 is shown which includes (a) a balloon catheter comprising a balloon 2318 and an outer sheath 2312, (b) an elongate inner member 2314 disposed within the balloon 2318 and the outer sheath 2312 of the balloon catheter, the elongate inner member 2314 having an enlarged tip 2314*t* and being used to provide access to the delivery site, and (c) a containment sheath 2319 disposed at least partially around a scaffold 2320 and maintaining the scaffold 2320 in a compressed state, when the scaffold 2320 is positioned on the balloon 2318 as shown. In order to assist with its removal, the containment sheath 2319 may be provided with a removal tab 2319*t* and may snap onto and extend only partially around the outer sheath 2312, as shown in a side view in FIGS. 23A and 23B and in an end view in FIG. 23D.

Figure 23B:
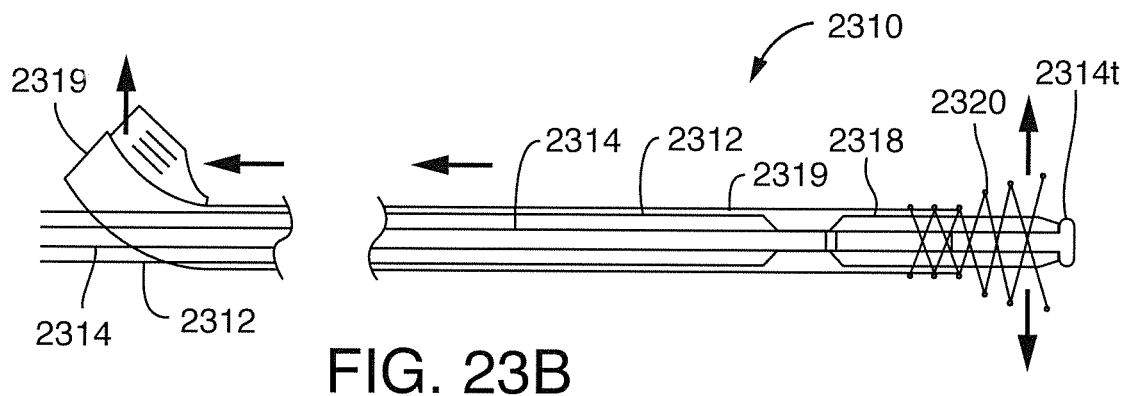
Figure 23C:
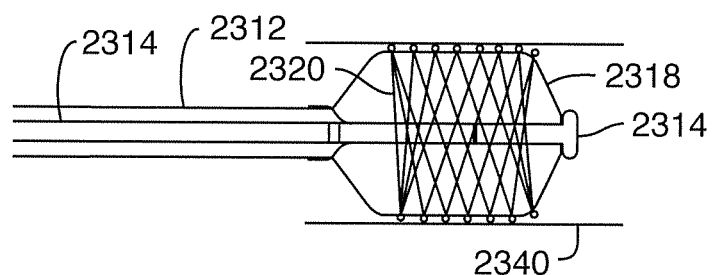
Figure 23D:
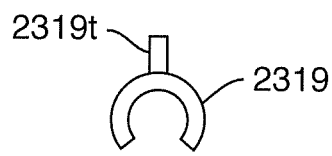
FIG. 23D is a schematic end view of a containment sheath shown in FIGS. 23A and 23B.

During a delivery procedure, once the tip 2314*t* of the elongate inner member 2314 is positioned at a desired target location, the outer sheath 2312, balloon 2318, scaffold 2320 and containment sheath 2319 may be advanced over the elongate inner member 2314, at which point the containment sheath 2319 may be removed from the assembly 2310, for example, by gripping removal tab 2319*t* and pulling the containment sheath 2319 proximally as shown in FIG. 23B. By pulling the containment sheath 2319 upward, the containment sheath 2319 may be removed from the outer sheath 2312 if desired. Once the containment sheath 2319 is pulled from the scaffold 2320, the scaffold self-expands (the scaffold 2320 is shown in a partially expanded state in FIG. 23B). After the containment sheath 2319 is pulled from the scaffold 2320, the balloon 2318 may be inflated to maximize conformance between the scaffold 2320 and surrounding tissue 2340, as shown in FIG. 23C. Although the containment sheath 2319 in FIGS. 23A-23D does not completely surround the outer sheath 2312, in other embodiments, the containment sheath 2319 may be configured to completely surround the outer sheath 2312, in which case the containment sheath 2319 is pulled proximally to allow self-expansion of the scaffold 2320 and inflation of the balloon 2318.

In simplified embodiment, a delivery assembly 2010 like that illustrated in FIGS. 23A-23D is provided, except that there is no elongate inner member 2314, in which case the balloon catheter serves as the innermost member.

In a further simplified embodiment, a delivery assembly 2010 like that illustrated in FIGS. 23A-23D is provided, except that there is no elongate inner member 2314 and containment sheath 2319. In such an embodiment, the scaffold 2310 may be crimped on the balloon 2318, holding it in place.

Other aspects pertain to systems in which a balloon is initially used for dilation followed by scaffold release.

Figure 24A:
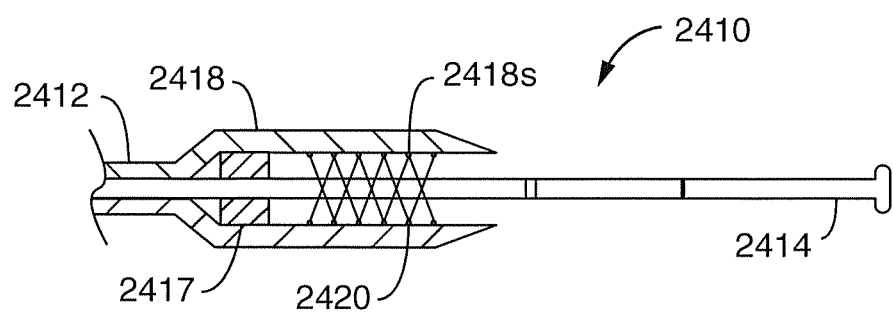
FIGS. 24A, 24B and 24C are schematic partial cross-sectional side views of a distal end of a scaffold delivery system, shown at three stages of deployment of a scaffold, in accordance with an embodiment of the present disclosure.
Figure 24B:
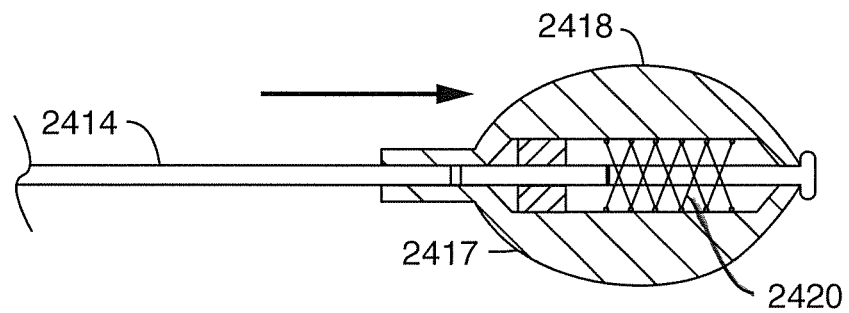
Figure 24C:
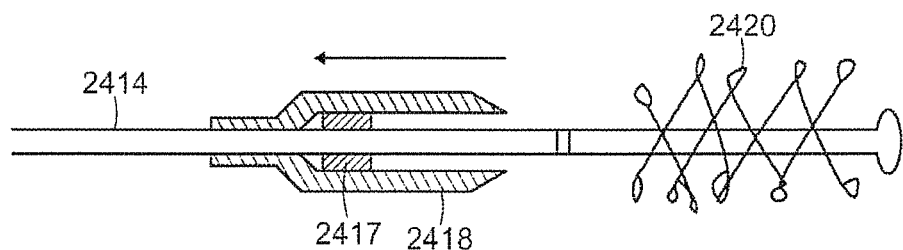

In one specific example illustrated in FIGS. 24A-24C, a delivery system 2410 is shown which includes (a) a balloon catheter comprising a catheter shaft 2412 (distal-most portion shown only) having a central lumen and an annular inflation lumen, a balloon 2418 having an inner balloon surface 2418s, and an inner ring 2417, (b) a scaffold 2420, which is expanded against the inner balloon surface 2418s and is disposed distal to the inner ring 2417, and (c) an elongate inner member 2414 positioned within the catheter shaft 2412, balloon 2418, inner ring 2417 and scaffold 2420. During a delivery procedure, once the tip of the elongate inner member 2414 is positioned at a desired target location, the catheter shaft 2412, balloon 2418, inner ring 2417 and scaffold 2420 may be advanced over the elongate inner member 2414, with the inner ring 2417 ensuring that the scaffold 2420 advances with the balloon 2418, at which point the balloon may be expanded as shown in FIG. 24B. The balloon 2418 is then deflated and the balloon catheter, including the outer sheath 2412, balloon 2418 and inner ring 2417, is withdrawn distally, resulting in deployment and expansion of the scaffold 2420 at the desired target location. The scaffold 2420 may be maintained at the delivery location while the balloon catheter is withdrawn, for example, by one or more retention features on the elongate inner member 2414. Such retention features may include steps, bumps, hooks, barbs, or rings that engage the at least a portion of the scaffold 2420 (e.g., a distal end of the scaffold 2420) to maintain positioning during retraction of the balloon 2418, among other possibilities.

In another specific example illustrated in FIGS. 25A-25D, a delivery assembly 2510 is shown which includes (a) a balloon catheter comprising a balloon 2518 and catheter shaft 2512 (distal-most portion shown only) having a central lumen and an annular inflation lumen, (b) an elongate inner member 2514 disposed within the balloon 2518 and central lumen of the catheter shaft 2512, and (c) a containment sheath 2519 disposed at least partially around the scaffold 2520, which scaffold 2520 is positioned adjacent the balloon 2518 as shown. As best seen from the perspective view shown in FIG. 25D, the containment sheath 2519 comprises a first portion 2519s that corresponds to the position of the scaffold 2520 and maintains the scaffold 2520 in a compressed state, a second portion 2519b that corresponds to the position of the balloon 2518 and a third portion 25190 that corresponds to the position of the outer sheath 2512. As with the embodiment of FIGS. 23A-23C, in order to assist with its removal the containment sheath 2519 may be provided with a removal tab 2519t and may snap onto and extend only partially around the outer sheath 2512.

Figure 25A:
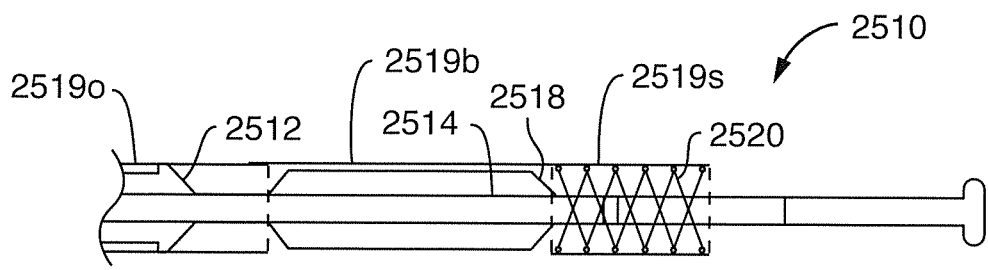
FIGS. 25A, 25B and 25C are schematic partial cross-sectional side views of a distal end of a scaffold delivery system, shown at various stages of deployment of a scaffold, in accordance with an embodiment of the present disclosure.
Figure 25B:
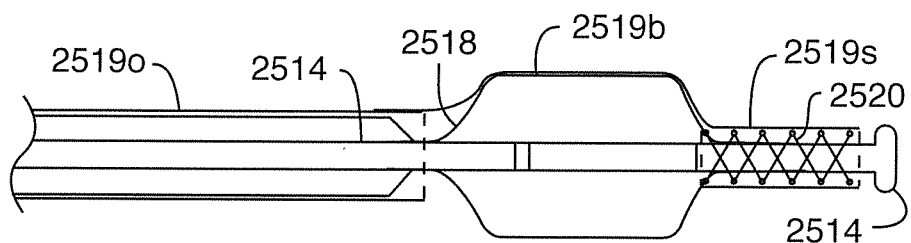
Figure 25C:
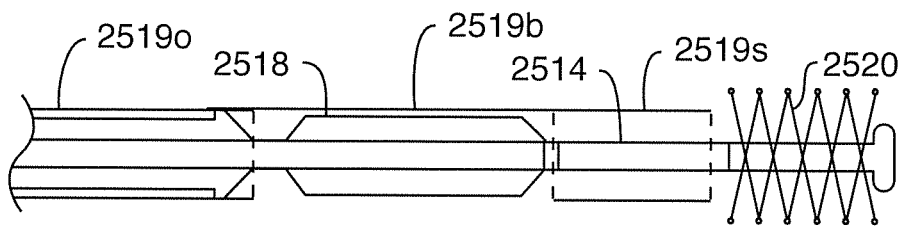
Figure 25D:
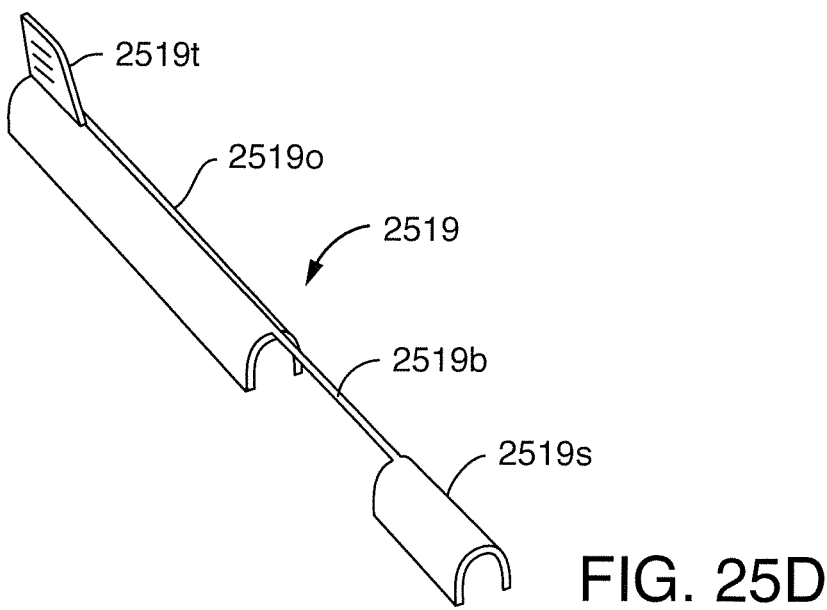
FIG. 25D is a schematic perspective view of the containment sheath shown in FIGS. 25A-25C.

During a delivery procedure, once the tip of the elongate inner member 2514 is positioned at a desired target location, catheter shaft 2512, balloon 2508, scaffold 2520 and containment sheath 2519 may be advanced over the elongate inner member 2514 to the target location, at which point the balloon 2518 may be expanded as shown in FIG. 25B. Due to the fact that the second portion 2519b that corresponds to the location of the balloon 2518 is of small cross-section, the balloon 2518 may be expanded in the presence of the containment sheath 2519 without disrupting the ability of the containment sheath 2519 to maintain the scaffold 2520 in a compressed state. Upon deflation of the balloon 2518, catheter shaft 2512, balloon 2508, scaffold 2510 and containment sheath 2519 may be retracted by a length approximately equal to the length of the balloon 2518, thereby aligning the scaffold 2820 with the sinus tissue previously expanded by the balloon 2518. At this point, the containment sheath 2519 may be removed from the assembly 2510, for example, by gripping removal tab 2519t and pulling the containment sheath 2519 proximally. As the containment sheath 2519 is removed from the scaffold 2520, the scaffold self-expands as shown in FIG. 25C and is released, at which point all remaining components of the delivery system 2510 may be withdrawn from the subject. Alternatively, upon deflation of the balloon 2518, catheter shaft 2512, balloon 2508, and containment sheath 2519 may be retracted, leaving scaffold 2520 in place for placement distal to the balloon dilation 2518.

Figure 26A:
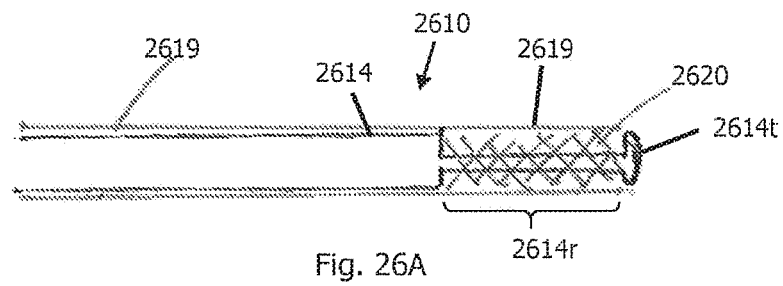
FIGS. 26A and 26B are schematic partial cross-sectional side views of a distal end of a scaffold delivery system, shown at two stages of deployment of a scaffold, in accordance with an embodiment of the present disclosure.
Figure 26B:
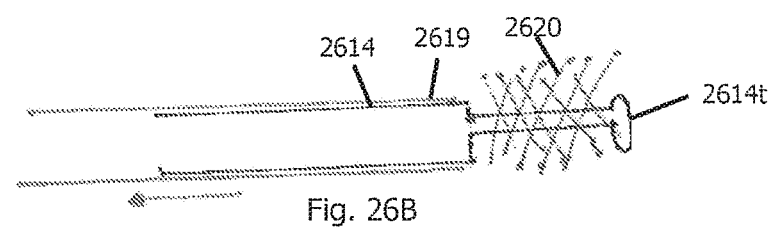

In still other embodiments, a containment sheath may be employed for delivery without an accompanying balloon catheter. For example, in one specific example illustrated in FIGS. 26A-26B, a delivery system 2610 is shown which includes (a) an elongate inner member 2614 having reduced diameter region 2614r and an enlarged tip 2614t that may be used to provide access to a delivery site and (b) a containment sheath 2619 disposed at least partially around a scaffold 2610, which is positioned in a recess formed by the reduced diameter region 2614r in the embodiment shown. In order to assist with its removal, the containment sheath 2619 may be provided with a removal tab and may snap onto and extend only partially around the elongate inner member 2614 (e.g., as discussed previously in conjunction with FIGS. 23A-23D). During a delivery procedure, once the tip 2614t of the elongate inner member 2614 is positioned at a desired target location, containment sheath 2619 may be withdrawn, for example, by gripping and pulling the containment sheath 2619 proximally. Once the containment sheath 2619 is pulled away from the scaffold 2620, the scaffold 2620 self-expands as shown in FIG. 26B. Although the containment sheath 2619 in FIGS. 26A-26B completely surrounds the elongate inner member 2614 in the particular embodiment shown, in other embodiments, the containment sheath 2619 may be configured to only partially surround the elongate inner member 2614. Additionally, the elongate inner member 2614 may be flexible or rigid, and may be pre-shaped, for example, having a curve suitable for providing access to sphenoid, frontal, and/or maxillary sinuses. This embodiment may also be used in conjunction with an access sheath or guide catheter, among other possibilities.

Figure 27A:
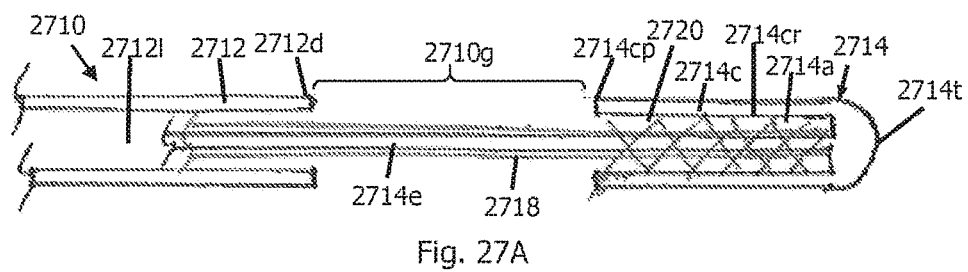
FIGS. 27A and 27B are schematic partial cross-sectional side views of a distal end of a scaffold delivery system, shown at two stages of deployment of a scaffold, in accordance with an embodiment of the present disclosure.
Figure 27B:
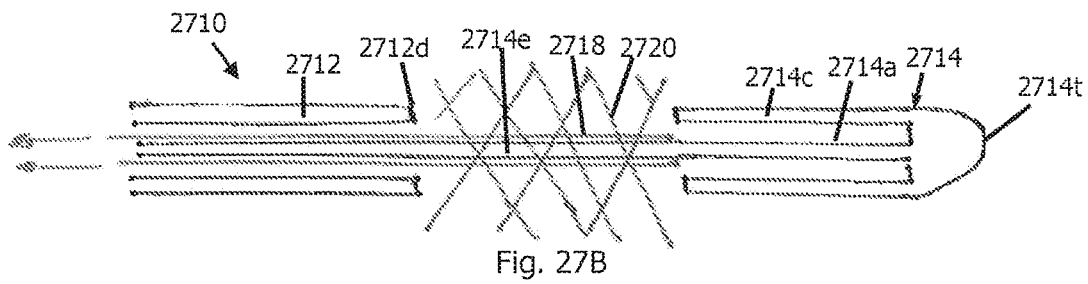

In another embodiment illustrated in FIGS. 27A and 27B, a distal end of a delivery system 2710 is shown, which contains a delivery member 2714 that includes an elongate inner member 2714e, a surrounding portion, for example, a hollow cylindrical portion 2714c, and a distal tip 2714t, wherein the elongate inner member 2714e and cylindrical portion 2714c together form an annular cavity 2714a. The elongate inner member 2714e is positioned within a lumen of an intermediate elongate member 2718, and a scaffold 2720 is compressed within the annular cavity 2714a, with an inner (luminal) surface of the scaffold in contact with an outer surface of the a distal section of the intermediate elongate member 2718 and an outer (abluminal) surface of the scaffold in contact with a radially-inward-facing surface 2714*cr* of the cylindrical portion 2714*c* of the delivery member 2714. The system 2710 further includes a delivery sheath 2712 having a distal end 2712*d*. The elongate inner member 2714*e* of the delivery member 2714 and the intermediate elongate member 2718 together extend proximally into a lumen 2712*l* of the delivery sheath 2712.

As illustrated in FIG. 27A, a proximal end 2714*cp* of the cylindrical portion 2714*c* is spaced from the distal end of the sheath 2712*d* thereby creating a gap 2710*g*, in order to facilitate delivery of the scaffold 2720 as described below in conjunction with FIG. 27B. During delivery, however, the delivery member 2714 and the intermediate elongate member 2718 may be retracted relative to the delivery sheath 2712 (or vice versa) to a point where the proximal end 2714*cp* of the cylindrical portion 2714*c* abuts the distal end 2712*d* of the sheath 2712, if desired. Once the delivery system is positioned at a target site, the delivery sheath 2712 may be retracted relative to the delivery member 2714 and intermediate elongate member 2718 to provide a gap 2710*g* between the proximal end 2714*cp* of the cylindrical portion 2714*c* and the distal end 2712*d* of the sheath 2712*d* as shown in FIG. 27A. Subsequently, and with reference to FIG. 27B, the elongate intermediate member 2718 may be retracted relative to the delivery sheath 2712 and delivery member 2714, thereby pulling the scaffold 2720 from the annular cavity 2714*a* and allowing it to expand in the gap 2710 between the proximal end 2714*cp* of the cylindrical portion 2714*c* and the distal end of the sheath 2712*d*.

The scaffold 2720 may be pulled from the annular cavity 2714*a* by various mechanisms. For example, the scaffold 2720 may be pulled from the annular cavity 2714*a* by providing one or more temporary attachment features on the elongate intermediate member 2718. Such attachment features may include, for example, steps, bumps, hooks, barbs, or rings that engage the at least a portion of the scaffold 2720 (e.g., a distal end of the scaffold 2720), among other possibilities. As another example, the scaffold 2720 may be pulled from the annular cavity 2714*a* as a result of friction forces. For instance, the scaffold 2720 may have a higher force of friction when in contact with the material provided on the outer surface of the distal end of the elongate intermediate member 2718 than it does when in contact with the material provided on the radially-inward-facing surface 2714*cr* of the cylindrical portion 2714*c* of the delivery member 2714. Examples of suitable materials for the outer surface of the distal end of the elongate intermediate member 2718 and examples of materials suitable for the radially-inward-facing surface 2714*cr* of the cylindrical portion 2714*c* are set forth above in conjunction with FIGS. 8A and 8B.

Figure 27C:
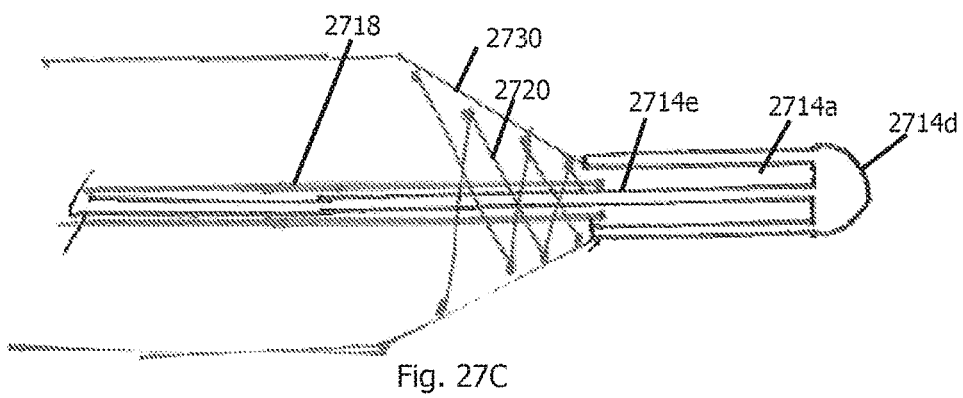
FIG. 27C is a schematic partial cross-sectional side view illustrating the loading of the scaffold delivery system of FIGS. 27A-27B, in accordance with an embodiment of the present disclosure.

An example of a method for a loading delivery member 2714 like that of FIG. 27A is illustrated in FIG. 27C, in which a scaffold 2720 is advanced distally through a funnel 2730 thereby reducing the diameter of the scaffold 2720 to that of the annular cavity 2714*a* of the delivery member 2714. In some instances, the scaffold 2720 may be pushed from its proximal end 2720*p* through the funnel 2730 and into the annular cavity 2714*a*, for example, using a pusher member 1136 like that described in conjunction with FIGS. 11A-11E, among other possibilities.

Figure 28A:
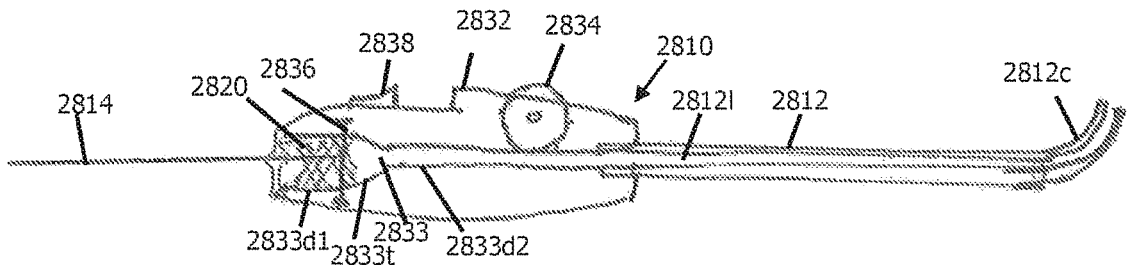
FIG. 28A is a schematic partial cross-sectional side view of a scaffold delivery system, in accordance with an embodiment of the present disclosure.

In another embodiment illustrated in FIG. 28A, a delivery system 2810 is shown, which includes a handle 2832 that comprises a thumb slide 2838 and a thumb wheel 2834, as well as an delivery sheath 2812 (e.g., a guide catheter) extending from a distal end of the handle 2832 and having a curved section 2812*c*, which may be used to enhance access to a particular target site. The handle 2832 further comprises a loading lumen 2833 with a first region 2833*d*1 having a first diameter, a second region 2833*d*2 having a second diameter, and a tapered region 2833*t* (e.g., in the shape of a frustum) between the first region 2833*d*1 and the second region 2833*d*2 in which the diameter of the lumen 2833 is gradually reduced from the first diameter at a proximal end of the tapered region 2833*t* to the diameter of the second region 2833*d*2 at a distal end of the tapered region 2833*t*. The first diameter may be approximately the same as or greater than an uncompressed diameter of a scaffold 2820 to be delivered. The second diameter may approximately the same as or less than an inside diameter of a lumen 2812*l* of the outer sheath 2812. In this embodiment, a plurality of loading pins 2836 are employed to advance the scaffold 2820.

In some embodiments, the loading pins 2836 are inserted through openings in the wall of the scaffold 2820 (e.g., between scaffold braids) such that distal advancement of the loading pins 2836 results in distal advancement of the scaffold 2820. The loading pins 2836 may be advanced, for example, using a suitable mechanism such as a thumb slide 2838 like that shown in FIG. 28A through a suitable interface (e.g., a ring) which engages the loading pins and moves them in tandem. One example of such a ring 2837 is shown in dashed lines in the end view of FIG. 28F. In one alternative embodiment, the thumb slide may correspond to a portion of a sliding ring. To the extent that the loading pins 2836 do not engage with the elongate inner member 2814, the elongate inner member 2814 may be advanced independently of the loading pins 2836, for example, by a thumb wheel 2834 as shown in FIG. 28A.

In some embodiments, the loading pins 2836 are inserted through openings in the wall of the scaffold 2820 and further into the inner member 2814 at a distal end of the inner member 2814 such that distal advancement of the elongate inner member 2814 results in advancement of the loading pins 2836 and scaffold 2820.

Figure 28B:
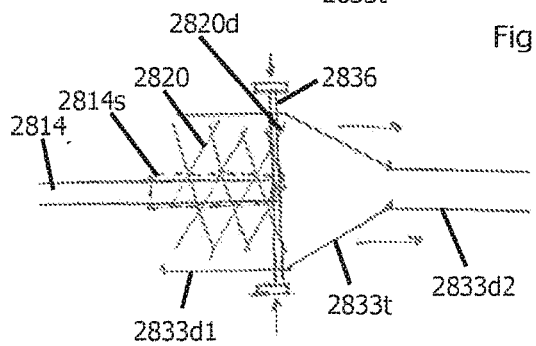
FIGS. 28B and 28C are schematic partial cross-sectional side view of select components within a portion of a scaffold delivery system, shown at two stages of deployment of a scaffold, in accordance with an embodiment of the present disclosure.
Figure 28C:
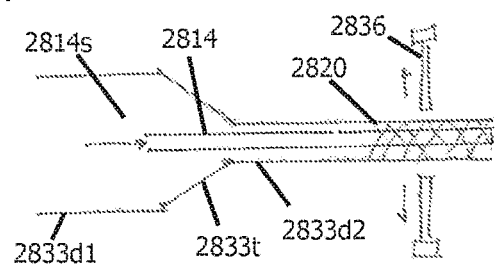
Figure 28D:
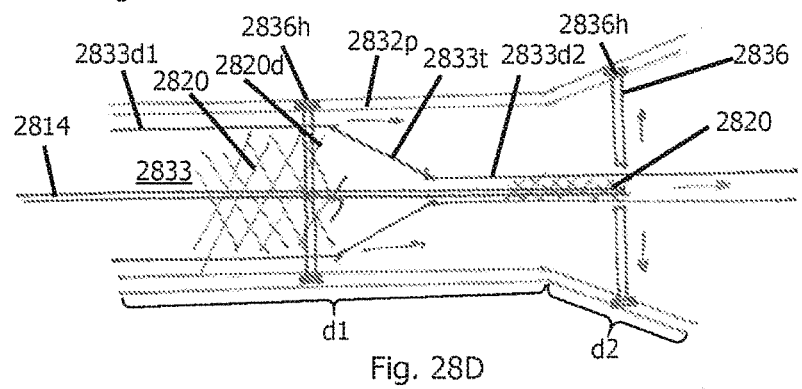
FIG. 28D is a schematic partial cross-sectional side view of select components within a portion of a scaffold delivery system, in accordance with an embodiment of the present disclosure.

In either case, and as seen from the partial side views of FIG. 28B and FIG. 28C (which simultaneously show the system at two different points in time) and the partial side view of FIG. 28D, distal advancement of the loading pins 2834 (i.e., in the direction of the arrows in FIG. 28B) results in distal advancement of the scaffold 2820, including distal advancement of the distal end 2820*d* of the scaffold 2820 from the first region 2833*d*1, through the tapered region 2833*t*, and into the second region 2833*d*2, thereby compressing the scaffold 2820 onto a support segment 2814*s* that is disposed at the distal end 2814*d* of the elongate inner member 2814.

It is noted that the pins 2836 may travel distally through a variety of longitudinal pathways provided in the handle 2832. Examples of longitudinal pathways include pathways that comprise longitudinal slots, including simple slots and longitudinal pathways having a T-shaped cross section, among others.

Figure 28E:
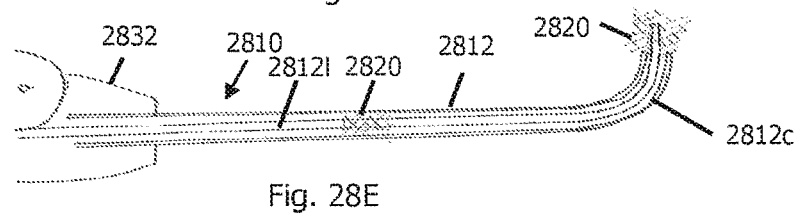
FIG. 28E is a schematic partial cross-sectional side view of a distal end of a scaffold delivery system, in accordance with an embodiment of the present disclosure.
Figure 28F:
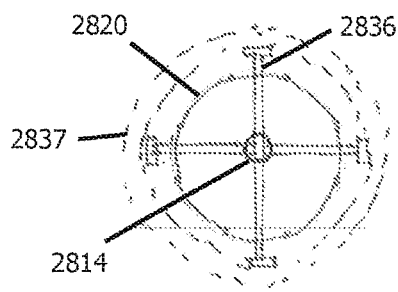
FIG. 28F is a schematic cross-sectional end view of select components of a scaffold delivery system, in accordance with an embodiment of the present disclosure.

After the scaffold 2820 is loaded onto the support segment 2814*s* of the elongate inner member 2814, the pins 2836 can be removed from the scaffold 2820 and the elongate inner member 2814 by a suitable method. For example, the pins 2836 may be removed manually or mechanically. For instance, with reference to FIG. 28D, the heads of the pins 2836 may slide through longitudinal pathways in the handle 2832 (the position 2832*p* of the heads of the pins 2836 as they pass through the pathways is shown), wherein the longitudinal pathways allow the heads of the pins 2836 to maintain a constant radial distance from the center of the lumen as the pins 2836 move distally over a first distance d1 and wherein the longitudinal pathways cause the heads of the pins 2836 to radially diverge from the center of the lumen as the pins 2836 move distally over a second distance d2. The result of this divergence is that the pins 2836 become disengaged from the elongate inner member 2814 and scaffold 2820, which can subsequently be advanced down the lumen 2812*l* of the outer member 2812, for example, as shown in FIG. 28E.

Advancement of the scaffold 2820 along with elongate inner member 2814 may be brought about, for example, by providing one or more retention features on the distal end of the elongate inner member 2814. Such retention features may include, for example, steps, bumps, hooks, barbs, or rings that engage at least a portion of the scaffold 2820, among other possibilities. Advancement of the scaffold 2820 along with elongate inner member 2814 may also be brought about, for example, by as a result of friction forces. For instance, the scaffold 2820 surface may have a higher force of friction when in contact with the material provided on the outer surface of the distal end of the elongate inner member 2814 (e.g., the material on the outer surface of the support segment 2814*s*) than it does when in contact with the material provided on the surface of the lumen 2812*l* of the outer member 2812, allowing the support segment 2814*s* to pull the scaffold 2820 along with the support segment 2814*s* when the support segment 2814*s* is moved in either a proximal or a distal direction relative to the outer member 2812 as previously discussed. Alternatively or in addition, movement of the scaffold 2820 may be coordinated with movement of the elongate inner member 2814, for example, by providing one or more retention features on the inner support segment 2814*s* (e.g., steps, bumps, hooks, barbs, rings, etc.) that engage at least a portion of the scaffold 2820.

Figure 29A:
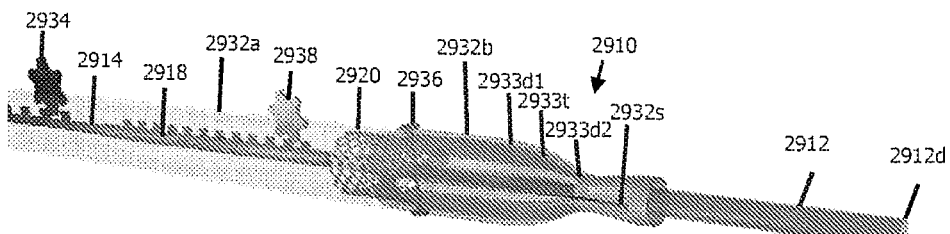
FIGS. 29A-29F are schematic, partially transparent, perspective views of a portion of a scaffold delivery system, shown at six sequential stages of deployment of a scaffold, in accordance with an embodiment of the present disclosure.
Figure 29B:
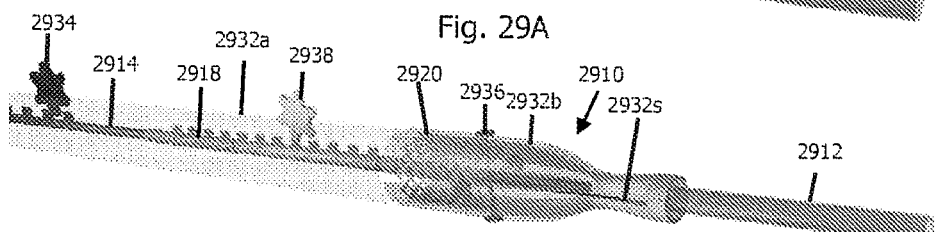
Figure 29C:
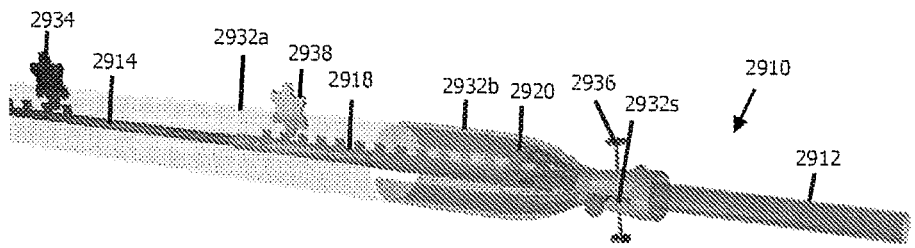
Figure 29D:
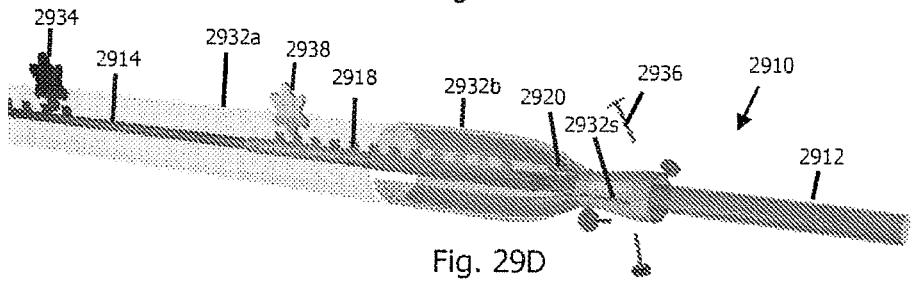

A particular embodiment of the disclosure will now be described in conjunction with FIGS. 29A-29J. Turning to FIG. 29A, a delivery system 2910 is shown, which includes a loading member shown in two sections, 2932*a* and 2932*b*, which can be used as a handle. Section 2932*a* includes a wheel 2934 whose teeth engage teeth on an elongate inner member 2914 and is used to advance the elongate inner member 2914. Section 2932*a* also includes a wheel 2938 whose teeth engage teeth on an engagement member 2918 and is used to advance the engagement member 2918. The engagement member 2918 includes a hollow shaft through which the elongate inner member 2914 extends, and the engagement member 2918 is longitudinally moveable along a portion of the elongate inner member 2914.

Section 2932*b* includes a loading lumen comprising a first region 2933*d*1 having a first diameter, a second region 2933*d*2 having a second diameter, and a tapered region 2933*t* between the first region 2933*d*1 and the second region 2933*d*2 wherein the diameter of the lumen 2933 is gradually reduced from the first diameter at a proximal end of the tapered region 2933*t* to the diameter of the second region 2933*d*2 at a distal end of the tapered region 2933*t*. The distal end of the loading lumen terminates at a lumen of a delivery sheath 2912 (e.g., a guide catheter). Section 2932*b* further includes a plurality of longitudinal pathways in the form slots 2932*s* (better seen in FIG. 29I) that extend into the loading lumen in section 2932*b*. Loading pins 2936 are inserted through the slots 2932*s*, through the scaffold 2920 wall and into support segment 2914*s* that is positioned at a distal end of the inner member 2914 (see, e.g., FIG. 29J).

As seen from FIGS. 29A-29F (which shows the system at six different points in time), distal advancement of the engagement member 2918 using wheel 2938 results in distal advancement of the elongate inner member 2914 (by abutment of the distal end of the engagement member 2918 with the proximal end of the support segment 2914*s* of the elongate inner member 2914), which in turn leads to distal advancement of the scaffold 2920 and loading pins 2936 to the distal end of section 2932*b*. Distal advancement of the scaffold 2920 results in radial compression of the scaffold 2920 as it proceeds through the section 2932*b*. Because the slots 2932*s* radially diverge from the central axis of the device 2910 and because the pins 2936 are configured to engage the slots 2932*s* (e.g., by engagement with grooves formed in the shafts of the pins 2936 or by engagement with heads of the pins), as the pins 2936 approach the distal ends of the slots 2932*s*, the pins 2936 also radially diverge from the central axis of the device 2910, removing the pins 2936 from engagement with the support segment 2914*s* shown in FIG. 29D. In an alternate embodiment, the pins may be removed manually or through a mechanical release mechanism.

Figure 29E:
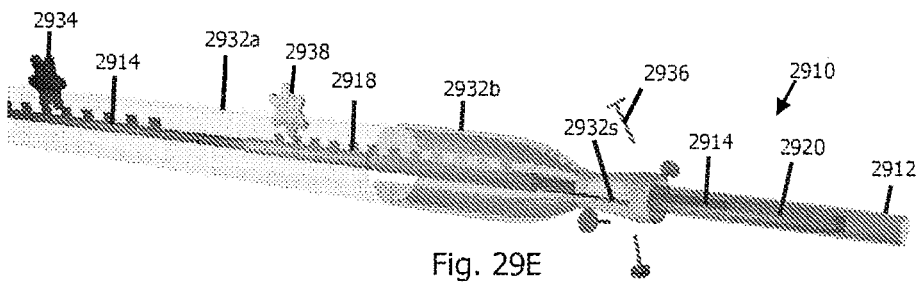
Figure 29F:
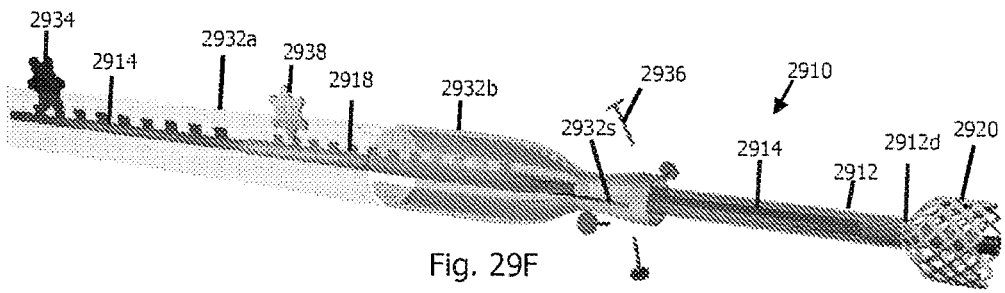
Figure 29G:
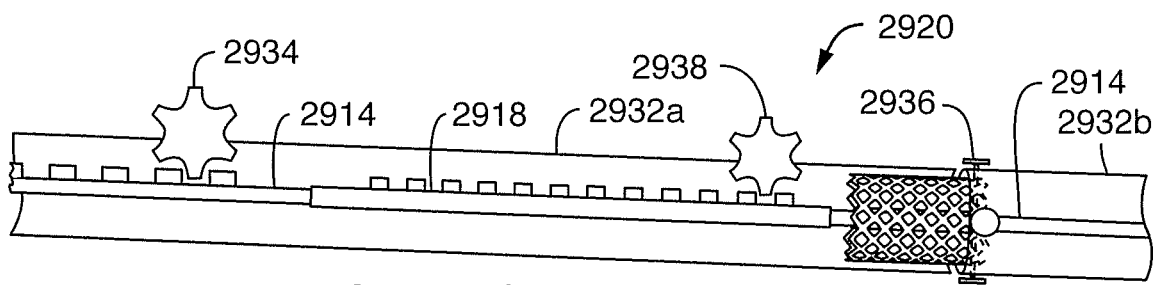
FIG. 29G is a schematic, partially transparent, side view of a portion of a scaffold delivery system, in accordance with an embodiment of the present disclosure.
Figure 29H:
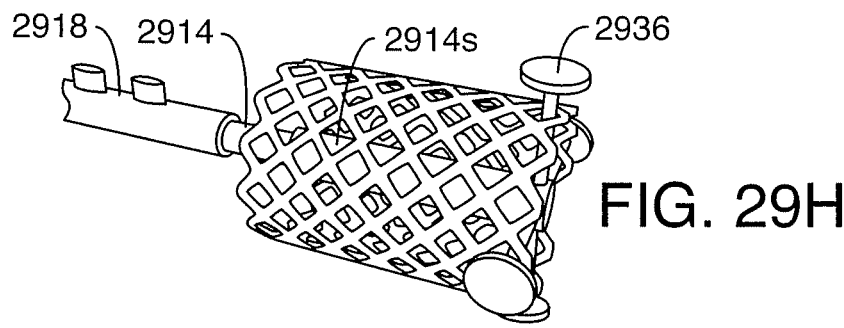
FIG. 29H is a schematic perspective view of select components within a portion of a scaffold delivery system, in accordance with an embodiment of the present disclosure.
Figure 29I:
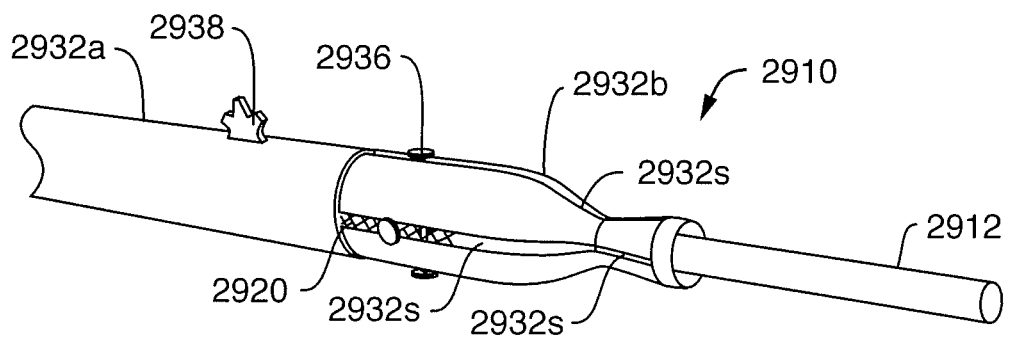
FIG. 29I is a schematic perspective view of a portion of a scaffold delivery system, in accordance with an embodiment of the present disclosure.
Figure 29J:
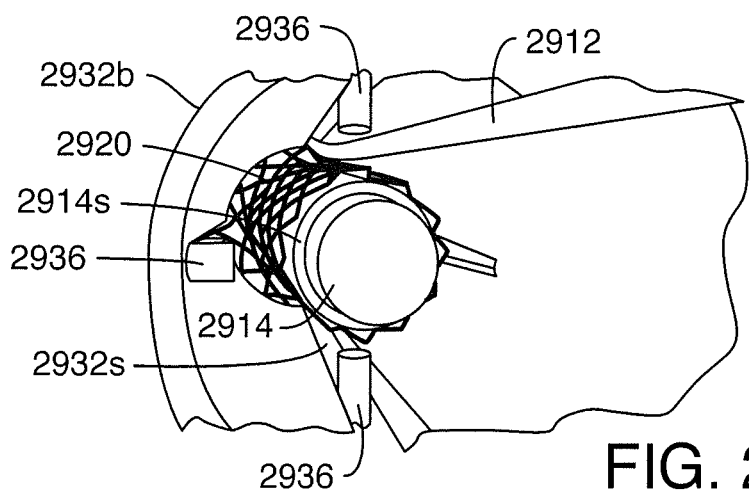
FIG. 29J is a schematic perspective cutaway view of a portion of a scaffold delivery system, in accordance with an embodiment of the present disclosure.

Subsequent distal advancement of the elongate inner member 2914 using wheel 2934 leads to advancement of the scaffold 2920 through the delivery sheath 2912 and out the distal end 2912*d* of the delivery sheath 2912 as shown in FIGS. 29E and 29F. Advancement of the scaffold 2920 along with elongate inner member 2914 may be assured, for example, by providing one or more retention features on the support segment 2914*s* of the elongate inner member 2914, allowing the support segment 2914*s* to pull the scaffold 2920 along with the support segment 2914*s* as the support segment 2914*s* moves in either a proximal or a distal direction relative to the delivery sheath 2912. Such retention features may include, for example, steps, bumps, hooks, barbs, or rings that engage at least a portion of the scaffold 2920, among other possibilities. Advancement of the scaffold 2920 along with support segment 2914*s* may also be assured, for example, by as a result of friction forces. For instance, the scaffold 2920 surface may have a higher force of friction when in contact with the material provided on the outer surface of the support segment 2914*s* than it does when in contact with the material provided on the inner surface of the lumen of the delivery sheath 2912, allowing the support segment 2914*s* to pull the scaffold 2920 along with the support segment 2914*s* as the support segment 2914*s* moves in either a proximal or a distal direction relative to the delivery sheath 2912, as previously discussed. Alternatively or in addition, movement of the scaffold 2920 may be coordinated with movement of the elongate inner member 2914, for example, by providing one or more retention features on the inner support segment 2914*s* (e.g., steps, bumps, hooks, barbs, rings, etc.) that engage at least a portion of the scaffold 2920.

Yet another embodiment of the disclosure will now be described in conjunction with FIGS. 37A-37D. Turning to FIGS. 37A-37D, a portion of a scaffold loading system 3700 is shown which includes a handle 3718, an outer delivery sheath 3212 provided at a distal end of the handle 3718 and an adaptor 3719 (e.g., a Touhy Borst valve with thumb screw closure) provided at a proximal end of the handle 3718. The assembly 3700 further includes a loading member 3730 having a distal end 2730*d* that is configured to be inserted into the adaptor 3719 such that it is attached to the handle 3718. The loading member 3730 has a tapered loading lumen 3733 (e.g., a funnel) wherein a diameter of the loading lumen 3733 gradually decreases as one proceeds from the proximal end 3730*p* of the loading member 3730 to the distal end 3730*d* of the loading member 3730.

Figure 37A:
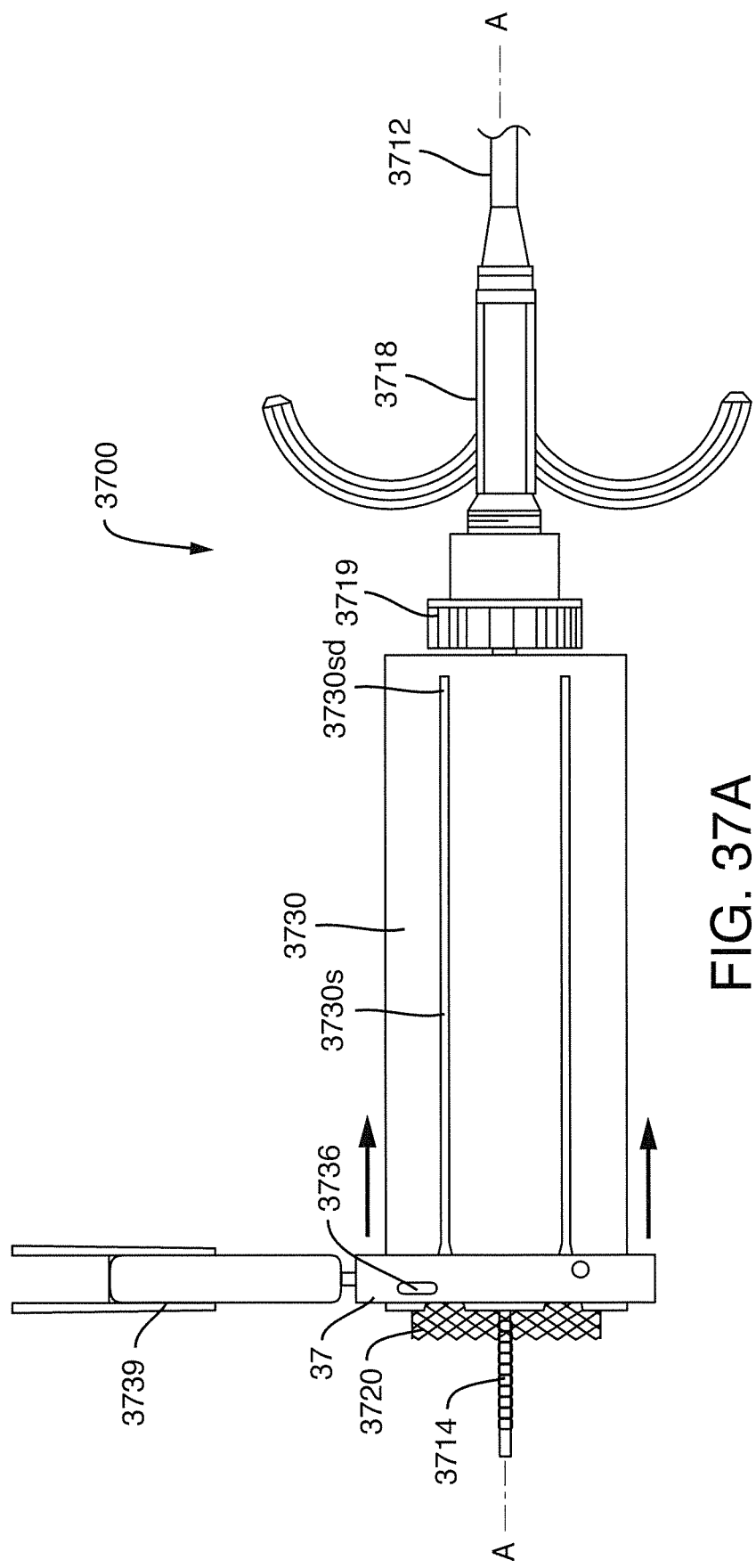
FIG. 37A is a schematic partial side view of a scaffold loading system, in accordance with an embodiment of the present disclosure.
Figure 37D:
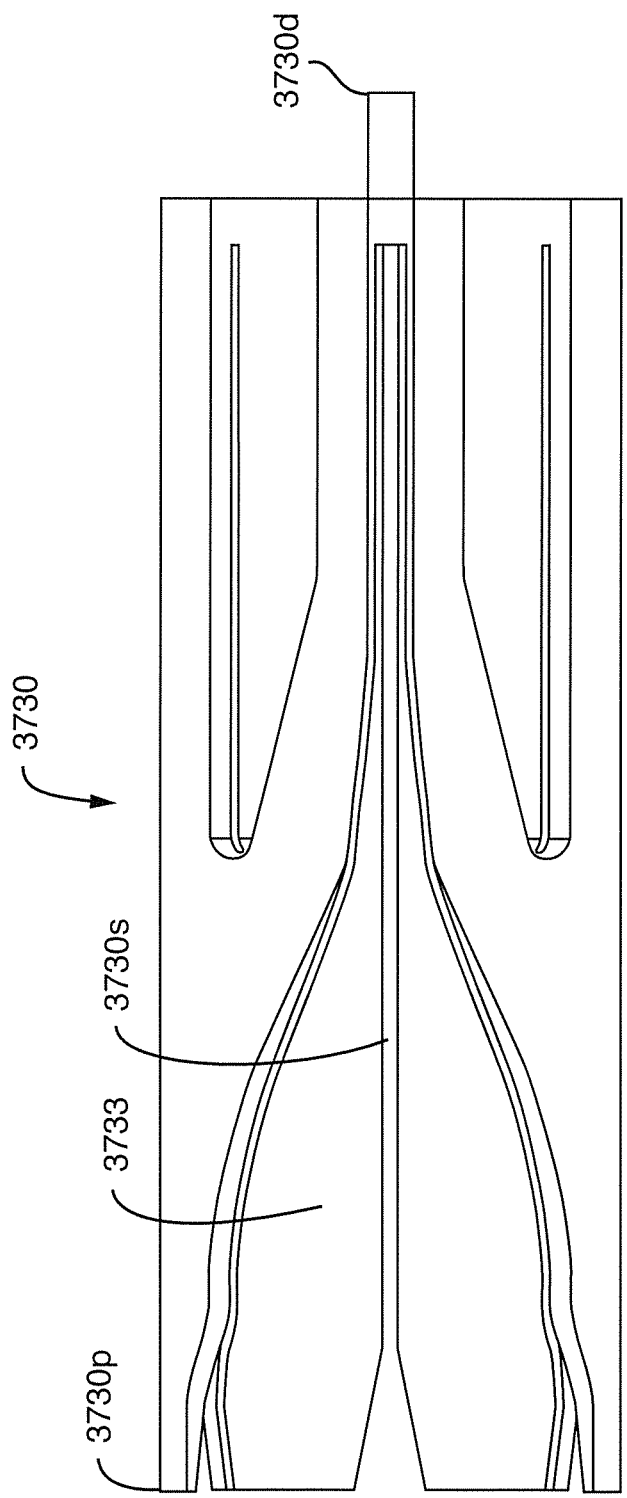
FIG. 37D is a schematic cross-section view of a component of FIG. 37A.

Loading member 3730 further includes a plurality of longitudinal pathways in the form of slots 3730s that extend from an exterior of the loading member 3730 into the loading lumen 3733. While FIG. 37A illustrates a separate loading member 3730 and ergonomic handle 3718 connected by an adaptor 3719, it will be appreciated that in other embodiments, these components can be integrated into a combined funnel and handle, for example, like that shown in FIG. 38, if desired.

Each loading pin 3736 (three pins 3736 are provided in the embodiment shown) is inserted through a first slot 3732s, through a first aperture in the scaffold 3720 wall, around the inner member 3714 or through the inner member 3714 (e.g through an aperture formed in the support segment 3714s of the inner member 3714, through a sleeve disposed around the inner member, etc.), through a second aperture in the scaffold 3720 wall opposite the first aperture, and through a second slot 3732s opposite the first slot 3732s. The loading pins are typically formed from a relatively strong material such as a metal or a polymer of suitable tensile strength. The pins may be, for example, in the form of relatively stiff rod-like members or filaments, such as a sutures, strings, threads or wires. Where it is desired to employ a plurality of loading pins 3736, in certain embodiments, each loading pin 3736 may pass through the same aperture formed in the support segment 3714s, whereas in certain other embodiments, each loading pin 3736 may pass through a different aperture formed in the support segment 3714s, in which case it may be desirable to stagger the loading pins 3736 and apertures at different longitudinal positions along a longitudinal axis, A, of the scaffold loading system 3700. Also shown is a packaging feature 3739 which may be used to hold the loading pins 3736 in place in the loading member 3730.

The loading pins 3736 may be advanced using any suitable mechanism that engages the loading pins 3736 and moves them in tandem, for instance, a movable ring 3738 in the embodiment shown. Although the loading pins 3736 pass through the ring 3738 at the same longitudinal position in the embodiment shown, in other embodiments, it may be desirable to stagger the loading pins 3736 such that they pass through the ring 3738 at the differing longitudinal positions as noted above.

When it is desired to load the scaffold 3720, the ring 3738 is distally advanced along a length of the loading member 3730 (i.e., in the direction of the arrows in FIG. 37A), which in turn leads to distal advancement of loading pins 3736, scaffold 3720 and inner member 3714 relative to the loading member 3730, valve 3712, handle 3718, and outer delivery sheath 3712. The ring 3738 is distally advanced along a length of the loading member 3730, resulting in radial compression of the scaffold 3720 as it proceeds through the tapered loading lumen 3733, until the loading pins 3637 reach distal ends 3732sd of the slots 3732s, at which point the scaffold 3720 has been compressed onto the support segment 3714s of the inner member 3714. At this point, the pins may be removed manually or through a suitable mechanical release mechanism.

Subsequent distal advancement of the elongate inner member 3714 leads to distal advancement of the scaffold 3720 as previously described. Advancement of the scaffold 3720 along with elongate inner member 3714 may be assured, for example, by providing one or more retention features on the support segment 3714s of the elongate inner member 3714, allowing the support segment 3714s to pull the scaffold 3720 along with the support segment 3714s as the support segment 3714s moves in either a proximal or a distal direction relative to the delivery sheath 3712. Such retention features may include, for example, steps, bumps, hooks, barbs, or rings that engage at least a portion of the scaffold 3720, among other possibilities. Advancement of the scaffold 3720 along with support segment 3714s may also be assured, for example, by as a result of friction forces. For instance, the scaffold 3720 surface may have a higher force of friction when in contact with the material provided on the outer surface of the support segment 3714s than it does when in contact with the material provided on the inner surface of the lumen of the delivery sheath 3712, allowing the support segment 3714s to pull the scaffold 3720 along with the support segment 3714s as the support segment 3714s moves in either a proximal or a distal direction relative to the delivery sheath 3712, as previously discussed. Alternatively or in addition, movement of the scaffold 3720 may be coordinated with movement of the elongate inner member 3714, for example, by providing one or more retention features on the inner support segment 3714s (e.g., steps, bumps, hooks, barbs, rings, etc.) that engage at least a portion of the scaffold 3720.

Still other aspects of the disclosure pertain to systems that incorporate a flexible fiberscope, for example, for primary navigation when the location cannot be directly visualized with a traditional scope and approach. In some embodiments, a small fiberscope (e.g., having a diameter of less than 0.30") may be provided alongside the scaffold delivery system or in a lumen of the delivery system. In some embodiments, a fiberscope is inserted through a centrally located cannula, which provides for delivery of the scaffold around the scope system. This allows for direct visual confirmation and scaffold placement into the tight locations within the sinus and decreases the amount of instrumentation that must be inserted to complete the procedure.

Other aspects of the disclosure pertain to systems that incorporate fiber illumination systems, for example, through a center cannula (e.g., ~0.020") or other lumen of the delivery system, or along the side of the delivery system. The illumination can provide additional positional feedback to assist with navigation and confirmation of scaffold delivery without significantly impacting trackability.

Other aspects of the disclosure pertain to navigation and access that may be utilized during device use, including by not limited to, direct visualization, endoscopic imaging, fluoroscopic imaging, tactile feedback sensors, pressure sensing, or electro-magnetic sensing.

Still other aspects of the disclosure pertain to access to the nasal cavity via a short, large diameter introducer, minimizing the impact of anatomical variability that may interfere with ideal access conditions. The introducer may be, for example, in the form of a partial conic section, for example, one having a diameter ranging from 3 to 20 mm and one end and a diameter ranging from 3 to 9 mm at another end. An introducer can be used in conjunction with other access technologies by allowing an expanded access port for additional manipulation and orientation without causing damage or irritation to surrounding nasal tissue.

Potential benefits of various aspects described herein include one or more of the following, among others: (a) more controlled loading of scaffold through even application of force across the entire diameter of the scaffold, allowing for consistent crimping of a large scaffold in the delivery system, which translates to more consistent expansion upon delivery, (b) more controlled access and delivery location of the scaffold, resulting in superior control and more precise stent placement within the target location, (c) the use of a combination of both pull and push forces to provide flexibility during deployment, enabling a partial deployment to anchor the scaffold position, followed by controlled deployment into the target space.

Example 1

A human cadaver study was conducted to assess the clinical performance of scaffolds and delivery systems in accordance with the present disclosure in the human anatomy. Device prototypes and delivery system prototypes were integrated to test multiple scenarios within the representative anatomy, both before and after functional endoscopic sinus surgery. Endpoints included visual appearance via endoscopy and clinical feedback.

Several small diameter scaffold prototypes are described in Table 1, while two large diameter scaffold prototypes are described in Table 2. These scaffolds are described in detail in "IMPLANTABLE SCAFFOLDS FOR TREATMENT OF SINUSITIS" supra.

TABLE 1

| Entry | Diameter (mm) | Filaments | Filament diameter (in) | Braid angle (deg) |
|---|---|---|---|---|
| 1 | 8 | 32 | 0.006" | 127 |
| 2 | 8 | 16 | 0.006" | 127 |
| 3 | 10 | 32 | 0.006" | 127 |
| 4 | 10 | 16 | 0.0065" | 127 |
| 5 | 10 | 16 | 0.0065" | 110 |

TABLE 2

| Design | Mass (mg) | Diameter (cm) | Length (mm) | Filaments | Filament diameter (in) | Braid angle (deg) |
|---|---|---|---|---|---|---|
| 2 filament braid offset | 60 | ~3.8 | 20 | 2 | 0.0075" twisted | 50 |
| 4 filament braid (monofilament) | 77 | ~3.8 | 20 | 4 | 0.0075" | 70 |

Figure 44:
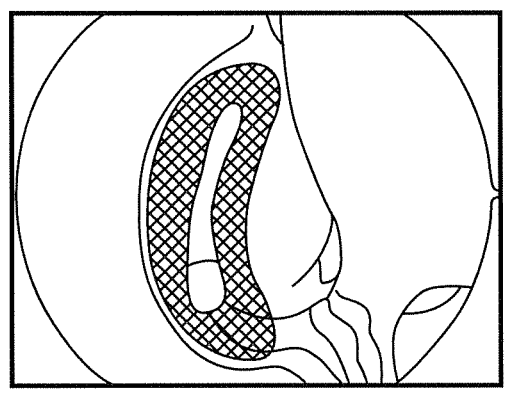
FIG. 44 is a photograph illustrating a 32 filament scaffold having a diameter of 13 mm diameter and a length of 10 mm, in accordance with an embodiment of the present disclosure, following deployment in the native middle meatus of a human cadaver.

Scaffolds were placed in the middle meatus, using delivery systems in accordance with the present disclosure, thereafter providing mechanical force to displace the middle turbinate medially and demonstrating the potential to deliver scaffolds (and any associated drug) to the ethmoid sinuses. Five deployments were conducted: (a) a 16 filament, 8 mm scaffold, (b) a 32 filament, 8 mm scaffold, (c) a 16 filament, 10 mm scaffold, (d) a 32 filament, 10 mm scaffold and (d) a 32 filament, 13 mm scaffold. Although all devices conformed relatively well to the tissues, displacing the middle turbinate medially (MT) and providing outward force on the uncinate process (UP) laterally, the 32 filament, 13 mm scaffold appeared to provide the best fit for the particular space into which it had been implanted. FIG. 44, is a photograph illustrating the 32 filament, 13 mm scaffold (length of 10 mm) following deployment in the middle meatus of a human cadaver. The implant conformed well to the tissues with appropriate medialization of middle turbinate.

Figure 45:
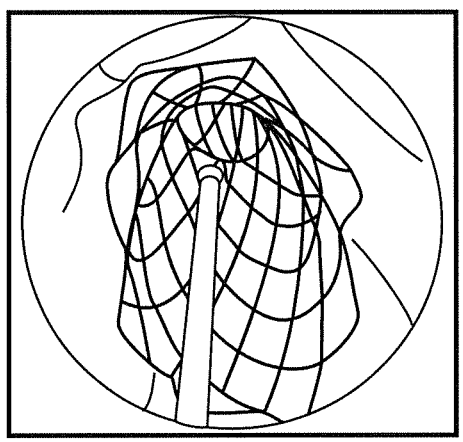
FIG. 45 is a photograph illustrating a 16 filament, 10 mm scaffold in accordance with an embodiment of the present disclosure following deployment in the frontal sinus ostia of a human cadaver.

Scaffolds were also placed in the frontal recesses of human cadavers using a delivery system in accordance with the present disclosure. In a first cadaveric specimen, the frontal recess could not be accessed prior to surgical intervention. The ostia to the frontal sinus was approximately 1 mm in diameter and could not accommodate the delivery device. Functional endoscopic sinus surgery (FESS) was conducted to remove ethmoid cells and expand the passage to the frontal sinus. Following this procedure, 32 filament (Table 1, entry 3) and 16 filament (Table 1, entry 4) devices were deployed into the fontal sinus ostia. Although both devices conformed well to the tissue, 16 filament device appeared to exhibit enhanced conformance for the particular space into which it had been implanted. FIG. 45 is a photograph illustrating a 16 filament, 10 mm scaffold following deployment the frontal sinus ostia.

In a second cadaver, the frontal sinus ostia was accessible prior to surgical intervention. 10 mm, 16 filament devices (n=1 from Table 1, entry 4 and n=1 from Table 1, entry 5) were deployed into the frontal sinus before and after FESS, respectively, using a delivery system in accordance with the present disclosure. These devices were appropriately placed from a delivery standpoint, conformed well to the sinus ostia, and were slightly undersized for the space immediately outside the ostia.

Figure 46:
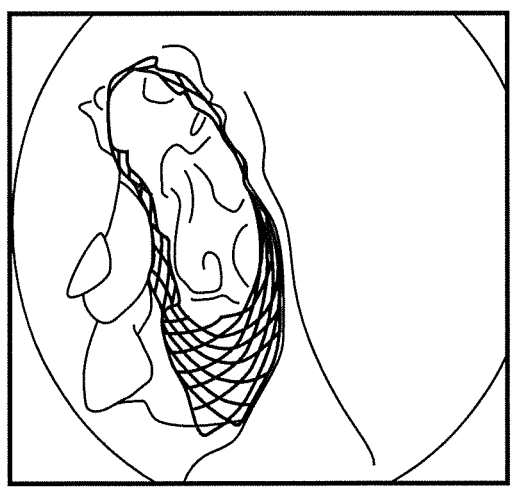
FIG. 46 is a photograph illustrating a 32 filament scaffold having a diameter of 17.5 mm and a length of 10 mm, in accordance with an embodiment of the present disclosure, following deployment in the ethmoid sinus of a human cadaver following FESS.

A 16 filament, 10 mm diameter scaffold, a 4 filament, 38 mm scaffold, a 2 filament, 38 mm scaffold, and a 32 filament, 17.5 mm scaffold were placed the ethmoid sinus of human cadavers following functional endoscopic sinus surgery using a delivery system in accordance with the present disclosure, with the 10 mm diameter scaffold appearing to be undersize for the particular space into which it had been implanted, the 38 mm scaffolds appearing to be oversize for the particular space into which it had been implanted, and with the 17.5 mm scaffold appearing to provide the best fit for the particular space into which it had been implanted. FIG. 46, is a photograph illustrating a 32 filament scaffold having a diameter of 17.5 mm and a length of 10 mm after deployment in the ethmoid sinus following FESS.

This study utilized 7.5 French and 9 French catheter systems. The 7.5F system was used to access all frontal sinuses, while the 9F system was used for device deployments into the ethmoid sinus. Both catheter diameters were acceptable, and devices functioned appropriately during use. A 90-degree bend was appropriate for reaching the frontal sinus.

Although various embodiments are specifically illustrated and described herein, it will be appreciated that modifications and variations of the present disclosure are covered by the above teachings and are within the purview of the appended claims without departing from the spirit and intended scope of the disclosure.

The invention claimed is:

1. A delivery system comprising,
   (a) a first assembly comprising
      (i) a loading member that comprises a tapered loading lumen having a proximal loading lumen end and a distal loading lumen end, wherein the proximal loading lumen end has a first diameter and the distal loading lumen end has a second diameter that is smaller than the first diameter and
      (ii) a delivery sheath having a delivery sheath lumen that is connected to the loading lumen, and
   (b) a second assembly comprising
      (i) a self-expanding scaffold, said scaffold comprising a scaffold wall and having a scaffold lumen, a proximal scaffold end, a distal scaffold end, an inner luminal surface, and an outer abluminal surface,
      (ii) an elongate advancement member having a proximal end and a distal end,
      (iii) at least one filament linking an end of the elongate advancement member to the scaffold, and
      (iv) an elongate inner member having a proximal end and a distal end, wherein the second assembly is configured to be inserted into the proximal loading lumen end of the loading member and advanced at least partially through the first assembly, such that the scaffold is moved through the loading lumen in a proximal-to-distal direction.

2. The delivery system of claim 1, wherein the first assembly further comprises a handle.

3. The delivery system of claim 2, wherein the loading member is in the form of a funnel and wherein either the funnel is detachable from the handle or wherein the funnel and handle are integrated into a single article.

4. The delivery system of claim 1, wherein the elongate inner member and the elongate advancement member are different, wherein the elongate advancement member is positioned distal to the elongate inner member, wherein at least one filament links the scaffold to the elongate advancement member.

5. The delivery system of claim 4, wherein the second assembly is configured to be advanced at least partially through the first assembly by applying force to either end of the elongate advancement member.

6. The delivery system of claim 5, wherein (a) the distal end of the elongate inner member is configured to engage the proximal end of the elongate advancement member.

7. The delivery system of claim 6, wherein a receptacle is provided at the proximal end of the elongate advancement member that is configured to receive the distal end of the elongate inner member.

8. The delivery system of claim 5, wherein said at least one filament is looped from the elongate advancement member, through at least one aperture in the scaffold wall, and back to the elongate advancement member.

9. The delivery system of claim 8, wherein both ends of said at least one filament are attached to the elongate advancement member.

10. The delivery system of claim 9, wherein the elongate advancement member comprises a groove and wherein one end of said at least one filament is positioned in the groove so that the one end can be cut and severed from the elongate advancement member.

11. The delivery system of claim 8, wherein the elongate advancement member comprises two portions that are configured to be reversibly joined.

12. The delivery system of claim 11, wherein the two portions are joined together, wherein one end of the at least one filament is attached to one of the two portions, and wherein an opposite end of the at least one filament is trapped between the two portions.

13. The delivery system of claim 5, wherein the elongate inner member is hollow and has a lumen, and wherein the second assembly further comprises an additional elongate member having a proximal end and a distal end that is configured to extend through the lumen of the inner elongate member and engage the proximal end of the elongate advancement member.

* * * * *